(12) United States Patent
Neitzel et al.

(10) Patent No.: US 7,939,657 B2
(45) Date of Patent: May 10, 2011

(54) N-SUBSTITUTED BENZENE SULFONAMIDES

(75) Inventors: Martin Neitzel, Pacifica, CA (US); Michael S. Dappen, Redwood City, CA (US); Jennifer Marugg, San Jose, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 11/738,863

(22) Filed: Apr. 23, 2007

(65) Prior Publication Data

US 2007/0191341 A1 Aug. 16, 2007

Related U.S. Application Data

(63) Continuation of application No. 10/976,746, filed on Oct. 29, 2004, now Pat. No. 7,208,488.

(60) Provisional application No. 60/515,612, filed on Oct. 29, 2003.

(51) Int. Cl.
*C07D 401/00* (2006.01)
*C07D 405/00* (2006.01)

(52) U.S. Cl. ...................................................... 540/524

(58) Field of Classification Search ............. 514/212.03, 514/212.08, 317, 319, 424; 540/524, 527; 546/216

See application file for complete search history.

(56) References Cited

U.S. PATENT DOCUMENTS

| | | | | |
|---|---|---|---|---|
| 3,419,548 A | * | 12/1968 | Karl Gatzi | 540/527 |
| 6,034,093 A | * | 3/2000 | Ewing et al. | 514/301 |
| 6,281,227 B1 | * | 8/2001 | Choi-Sledeski et al. | 514/307 |
| 6,632,816 B1 | * | 10/2003 | Stranix et al. | 514/237.5 |
| 2002/0151546 A1 | * | 10/2002 | Stranix et al. | 514/231.5 |

FOREIGN PATENT DOCUMENTS

| | | |
|---|---|---|
| JP | S55-020742 | 2/1980 |
| WO | WO00/50391 | 8/2000 |
| WO | WO 2002/062803 * | 8/2002 |
| WO | WO03/013527 | 2/2003 |
| WO | WO03/066592 | 8/2003 |

OTHER PUBLICATIONS

Curragh et al. (Journal of the Chemical Society (1962) 2948-52). Abstract.*
Adamson (Journal of the Chemical Society (1943) 0368-1769). Abstract.*
Sato et al. (JP 55020742). 1980. Abstract.*
Bell et al. (Journal of Medicinal Chemistry (2001), 44(18), 2933-2949).*
Le Diguarher at al. (Bioorganic and Medicinal Chemistry (2003), 11(14), 3193-3204).*
Seiffert, D. et al., "Presenilin-1 and -2 are Molecular Targets for Gamma-Secretase", The Journal of Biological Chemistry, vol. 275, No. 44, 2000, pp. 34086-34091.
International Search Report for PCT/US2004/035951 dated Mar. 30, 2005.

* cited by examiner

*Primary Examiner* — Bruck Kifle
(74) *Attorney, Agent, or Firm* — McDonnell Boehnen Hulbert & Berghoff LLP

(57) ABSTRACT

Disclosed are N-substituted benzenesulfonamides for use in treating or preventing cognitive disorders, such as Alzheimer's Disease.

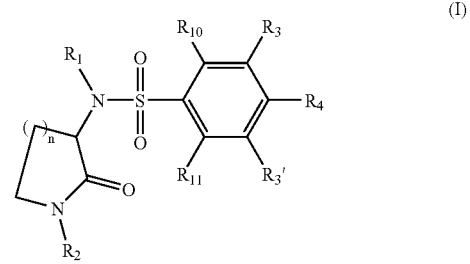

(I)

In Formula (I), $R_1$, $R_2$, $R_3$, $R_4$, $R_{3'}$, $R_{10}$ and $R_{11}$ are as described herein. The invention also encompasses pharmaceutical compositions comprising compounds of Formula (I) as well as methods of treating cognitive disorders using compounds of Formula (I).

6 Claims, No Drawings

US 7,939,657 B2

N-SUBSTITUTED BENZENE SULFONAMIDES

This application claims priority from U.S. provisional patent application No. 60/515,612, filed Oct. 29, 2003.

BACKGROUND OF THE INVENTION

1. Field of the Invention

The invention relates to N-substituted benzene sulfonamides which inhibit β-amyloid peptide release and/or its synthesis and, therefore, are useful in the prevention of cognitive disorders in patients susceptible to cognitive disorders and/or in the treatment of patients with cognitive disorders in order to inhibit further deterioration in their condition.

2. State of the Art

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39-43 amino acids designated the β-amyloid peptide (βAP) or sometimes Aβ, AβP or β/A4. β-Amyloid peptide was first purified and a partial amino acid sequence was provided by Glenner et al., Biochem. Biophys. Res. Commun., 120:885-890 (1984) The isolation procedure and the sequence data for the first 28 amino acids are described in U.S. Pat. No. 4,666,829.

Molecular biological and protein chemical analyses have shown that the β-amyloid peptide is a small fragment of a much larger precursor protein termed the amyloid precursor protein (APP), that is normally produced by cells in many tissues of various animals, including humans. Knowledge of the structure of the gene encoding APP has demonstrated that β-amyloid peptide arises as a peptide fragment that is cleaved from APP by protease enzyme(s). Sequential processing of the precursor protein by the enzymes referred to generically as beta- and gamma-secretases, give rise to the β-amyloid peptide fragment. Both enzymes have now been molecularly cloned, and characterized to differing levels.

Several lines of evidence indicate that progressive cerebral deposition of β-amyloid peptide plays a seminal role in the pathogenesis of AD and can precede cognitive symptoms by years or decades. See, for example, Selkoe, Neuron, 6:487-498 (1991). The most important line of evidence is the discovery that missense DNA mutations at amino acid 717 of the 770-amino acid isoform of APP can be found in affected members but not unaffected members of several families with a genetically determined (familial) form of AD (Goate et al., Nature, 349:704-706 (1990); Chartier Harlan et al., Nature, 353:844-846 (1989); and Murrell et al., Science, 254:97-99 (1991).) Another such mutation, known as the Swedish variant, is comprised of a double mutation changing lysine$^{595}$-methionine$^{596}$ to asparagine$^{595}$-leucine$^{596}$ (with reference to the 695 isoform was found in a Swedish family) was reported in 1992 (Mullan et al., Nature Genet., 1:345-347 (1992). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP metabolism, and subsequent deposition of its β-amyloid peptide fragment, can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs which are capable of inhibiting β-amyloid peptide release and/or its synthesis in vivo.

One approach toward inhibiting amyloid peptide synthesis in vivo is by inhibiting gamma secretase, the enzyme responsible for the carboxy-terminal cleavage resulting in production of β-amyloid peptide fragments of 40 or 42 residues in length. The immediate substrates for gamma secretase are β-cleaved, as well as β-cleaved carboxy-terminal fragments (CTF) of APP. The gamma-secretase cleavage site on β- and α-CTF fragments occurs in the predicted transmembrane domain of APP. Inhibitors of gamma-secretase have been demonstrated to effect amyloid pathology in transgenic mouse models (Dovey, H. F., V. John, J. P. Anderson, L. Z. Chen, P. de Saint Andrieu, L. Y. Fang, S. B. Freedman, B. Folmer, E. Goldbach, E. J. Holsztynska et al. (2001). "Functional gamma-secretase inhibitors reduce beta-amyloid peptide levels in brain." J Neurochem 76 (1): 173-81.)

Gamma secretase is recognized to be a multi-subunit complex comprised of the presenilins (PS1 or PS2), Nicastrin, Aph-1, and Pen 2 (De Strooper, B. (2003). "Aph-1, Pen-2, and Nicastrin with Presenilin generate an active gamma-secretase complex." Neuron 38 (1): 9-12; Edbauer, D., E. Winkler, J. T. Regula, B. Pesold, H. Steiner and C. Haass (2003). "Reconstitution of gamma-secretase activity." Nat Cell Biol 5 (5): 486-8; Kimberly, W. T., M. J. LaVoie, B. L. Ostaszewski, W. Ye, M. S. Wolfe and D. J. Selkoe (2003). "Gamma-secretase is a membrane protein complex comprised of presenilin, nicastrin, Aph-1, and Pen-2." Proc Natl Acad Sci USA 100 (11): 6382-7). Much evidence indicates that PS comprises the catalytic moiety of the complex, while the other identified subunits are necessary for proper maturation and sub-cellular localization of the active enzyme complex (reviewed in De Strooper, B. (2003). "Aph-1, Pen-2, and Nicastrin with Presenilin generate an active gamma-secretase complex." Neuron 38 (1): 9-12.) Consistent with this hypothesis: PS knock-out mice exhibit significant reductions in β-amyloid production (De Strooper, B., P. Saftig, K. Craessaerts, H. Vanderstichele, G. Guhde, W. Annaert, K. Von Figura and F. Van Leuven (1998). "Deficiency of presenilin-1 inhibits the normal cleavage of amyloid precursor protein." Nature 391 (6665): 387-90; Haass, C. and D. J. Selkoe (1998). "Alzheimer's disease. A technical KO of amyloid-beta peptide." Nature 391 (6665): 339-40; Herreman, A., L. Serneels, W. Annaert, D. Collen, L. Schoonjans and B. De Strooper (2000). "Total inactivation of gamma-secretase activity in presenilin-deficient embryonic stem cells." Nat Cell Biol 2 (7): 461-2); point mutations of putative active site aspartate residues in PS trans-membrane domains inhibit β-amyloid production in cells in a dominant negative fashion (Wolfe, M. S., W. Xia, B. L. Ostaszewski, T. S. Diehl, W. T. Kimberly and D. J. Selkoe (1999). "Two transmembrane aspartates in presenilin-1 required for presenilin endoproteolysis and gamma-secretase activity." Nature 398 (6727): 513-7; Kimberly, W. T., W. Xia, T. Rahmati, M. S. Wolfe and D. J. Selkoe (2000). "The transmembrane aspartates in presenilin 1 and 2 are obligatory for gamma-secretase activity and amyloid beta-protein generation." J Biol Chem 275 (5): 3173-8); active site directed substrate-based transition state isosteres designed to inhibit gamma secretase directly conjugate to PS (Esler, W. P., W. T. Kimberly, B. L. Ostaszewski, T. S. Diehl, C. L. Moore, J. Y. Tsai, T. Rahmati, W. Xia, D. J. Selkoe and M. S. Wolfe (2000). "Transition-state analogue inhibitors of gamma-secretase bind directly to presenilin-1." Nat Cell Biol 2 (7): 428-34; Li, Y. M., M. Xu, M. T. Lai, Q. Huang, J. L. Castro, J. DiMuzio-Mower, T. Harrison, C. Lellis, A. Nadin, J. G. Neduvelil et al. (2000). "Photoactivated gamma-secretase inhibitors directed to the active site covalently label presenilin 1." Nature 405 (6787): 689-94); finally, allosteric gamma secretase inhibitors have likewise been demonstrated to bind directly to PS (Seiffert, D., J. D. Bradley, C. M. Rominger, D. H. Rominger, F. Yang, J. E. Meredith, Jr., Q. Wang, A. H. Roach, L. A. Thompson, S. M. Spitz et al. (2000). "Presenilin-1 and -2 are molecular targets for gamma-secretase inhibitors." J Biol Chem 275 (44): 34086-91.)

Current evidence indicates that in addition to APP processing leading to β-amyloid synthesis, gamma-secretase also mediates the intra-membrane cleavage of other type I transmembrane proteins (reviewed in Fortini, M. E. (2002). "Gamma-secretase-mediated proteolysis in cell-surface-receptor signalling." Nat Rev Mol Cell Biol 3 (9): 673-84, see also Struhl, G. and A. Adachi (2000). "Requirements for presenilin-dependent cleavage of notch and other transmembrane proteins." Mol Cell 6 (3): 625-36.) Noteworthy among the known substrates of gamma-secretase is mammalian Notch 1. The Notch 1 protein is important for cell fate determination during development, and tissue homeostasis in the adult. Upon ligand engagement via the Notch ecto-domain, Notch undergoes sequential extra-cellular and intra-membrane processing analogous to APP. The intra-membrane processing of Notch mediated by gamma secretase leads to release of the Notch intracellular domain (NICD). The NICD fragment mediates Notch signaling via translocation to the nucleus, where it regulates expression of genes mediating cellular differentiation in many tissues during development, as well as in the adult.

Disruption of Notch signaling via genetic knock-out (KO) results in embryonic lethal phenotype in mice (Swiatek, P. J., C. E. Lindsell, F. F. del Amo, G. Weinmaster and T. Gridley (1994). "Notch1 is essential for postimplantation development in mice." Genes Dev 8 (6): 707-19; Conlon, R. A., A. G. Reaume and J. Rossant (1995). "Notch1 is required for the coordinate segmentation of somites." Development 121 (5): 1533-45.) The Notch KO phenotype is very similar to the phenotype observed PS1 KO mice, and precisely reproduced by PS1/PS2 double KO mice (De Strooper et al. (1998). "Deficiency of presenilin-1 inhibits the normal cleavage of amyloid precursor protein." Nature 391 (6665): 387-90; Donoviel, D. B., A. K. Hadjantonakis, M. Ikeda, H. Zheng, P. S. Hyslop and A. Bernstein (1999). "Mice lacking both presenilin genes exhibit early embryonic patterning defects." Genes Dev 13 (21): 2801-10; Herreman, A., L. Serneels, W. Annaert, D. Collen, L. Schoonjans and B. De Strooper (2000). "Total inactivation of gamma-secretase activity in presenilin-deficient embryonic stem cells." Nat Cell Biol 2 (7): 461-2.) This convergence of phenotypes observed in knock-out mice of either the substrate (Notch) or the enzyme (PS) suggests that inhibitors of gamma secretase that also inhibit Notch function may be limited as therapeutic agents owing to the importance of Notch function in adult tissues (Fortini, M. E. (2002). "Gamma-secretase-mediated proteolysis in cell-surface-receptor signalling." Nat Rev Mol Cell Biol 3 (9): 673-84.) As APP knock-out mice develop normally and without an overt phenotype Zheng, H., M. Jiang, M. E. Trumbauer, R. Hopkins, D. J. Sirinathsinghji, K. A. Stevens, M. W. Conner, H. H. Slunt, S. S. Sisodia, H. Y. Chen et al. (1996). "Mice deficient for the amyloid precursor protein gene." Ann NY Acad Sci 777: 421-6; Zheng, H., M. Jiang, M. E. Trumbauer, D. J. Sirinathsinghji, R. Hopkins, D. W. Smith, R. P. Heavens, G. R. Dawson, S. Boyce, M. W. Conner et al. (1995). "beta-Amyloid precursor protein-deficient mice show reactive gliosis and decreased locomotor activity." Cell 81 (4): 525-31, the cumulative evidence, therefore, suggests that preferred gamma secretase inhibitors would have selectivity for inhibiting gamma secretase processing of APP over gamma secretase processing of Notch.

SUMMARY OF THE INVENTION

In a broad aspect, the invention provides compounds of Formula I:

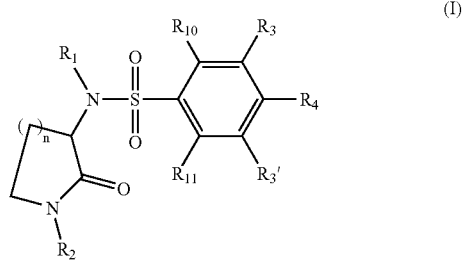

or a pharmaceutically acceptable salt thereof wherein
n is 1, 2, or 3;
$R_1$ is aryl $C_1$-$C_8$ alkyl, aryl $C_2$-$C_6$ alkenyl, or arylalkynyl,
   wherein the aryl group is optionally substituted with 1, 2, 3, 4, or 5 groups that are independently $C_1$-$C_6$ alkyl, $C_1$-$C_6$ alkoxy, halogen, haloalkyl, haloalkoxy, heteroaryl, heteroaryl($C_1$-$C_6$)alkoxy, arylalkoxy, aryloxy, $C_1$-$C_6$ alkoxycarbonyl, —O—CH$_2$CH$_2$—O—, —O—CH$_2$—O—, —C(O)NR$_{30}$R$_{31}$, —NHR', —NR'R", —N(R$_{16}$)C(O)—R$_{17}$, heterocycloalkyl, phenyl, aryl $C_1$-$C_6$ alkanoyl, phenylalkoxy, phenyloxy, CN, —SO$_2$-aryl, —S(O)$_x$—R$_{25}$, —(C$_1$-C$_4$ alkyl)-S(O)$_x$—R$_{25}$, —(C$_1$-C$_4$ alkyl)-SO$_2$-aryl, OH, C$_1$-C$_6$ thioalkoxy, C$_2$-C$_6$ alkenyl, —O—SO$_2$-aryl, CO$_2$H, wherein the heteroaryl portions of the above group are optionally substituted with 1, 2, or 3 groups that are independently C$_1$-C$_6$ alkyl, heteroaryl optionally substituted with 1 or 2 groups that are independently halogen, alkyl, alkoxy, haloalkyl, haloalkoxy, alkoxyalkyl or CN (in one aspect, pyridyl, thienyl, furanyl, imidazolyl, or pyrazolyl), C$_1$-C$_6$ alkoxy, C$_1$-C$_4$ alkoxy C$_1$-C$_4$ alkyl, C$_3$-C$_6$ cycloalkyl, halogen, or phenyl optionally substituted with 1, 2, 3, 4 or 5 groups that are independently halogen, OH, C$_1$-C$_6$ alkyl, C$_1$-C$_4$ alkoxy, CF$_3$, OCF$_3$, CN, or C$_1$-C$_6$ thioalkoxy, wherein the heterocycloalkyl and aryl portions of the above substituents are optionally substituted with 1 or 2 groups that are independently heteroaryl optionally substituted with 1 or 2 groups that are independently halogen, alkyl, alkoxy, haloalkyl, haloalkoxy, alkoxyalkyl or CN, (in one aspect, pyridyl, thienyl, furanyl, imidazolyl, or pyrazolyl), C$_1$-C$_6$ alkyl, C$_1$-C$_6$ alkoxy, C$_1$-C$_4$ alkoxy C$_1$-C$_4$ alkyl, C$_3$-C$_6$ cycloalkyl, halogen, or phenyl optionally substituted with 1, 2, 3, 4 or 5 groups that are independently halogen, OH, C$_1$-C$_6$ alkyl, C$_1$-C$_4$ alkoxy, CF$_3$, OCF$_3$, CN, or C$_1$-C$_6$ thioalkoxy, R$_{16}$ is H or C$_1$-C$_6$ alkyl;

R$_{17}$ is C$_1$-C$_6$ alkyl, aryl, heteroaryl, C$_1$-C$_6$ alkoxy, OH, aryloxy, heteroaryloxy, aryl(C$_1$-C$_6$)alkoxy, —NR$_{18}$R$_{19}$, cycloalkyl, or arylalkyl, wherein the cyclic portions of each of the above are optionally substituted with 1, 2, 3, 4, or 5 groups that are independently alkyl, alkoxy, halo, haloalkyl, haloalkoxy, CN, NH$_2$, NH(alkyl), N(alkyl)(alkyl), CO$_2$H, or C$_1$-C$_6$ alkoxycarbonyl;

R$_{18}$ and R$_{19}$ are independently H, C$_1$-C$_6$ alkyl, aryl, heteroaryl, heterocycloalkyl or aryl(C$_1$-C$_6$)alkyl, wherein the cyclic portions of each are optionally substituted with 1, 2, or 3 groups that are independently alkyl, alkoxy, halogen, hydroxyl, CF$_3$, or OCF$_3$;

wherein R' at each occurrence is independently H, C$_1$-C$_6$ alkyl, aryl, aryl(C$_1$-C$_4$)alkyl, C$_1$-C$_6$ alkanoyl, C$_3$-C$_8$ cycloalkyl, aryl(C$_1$-C$_6$)alkanoyl, heterocycloalkyl, heteroaryl(C$_1$-C$_4$)alkyl, —SO$_2$-alkyl, —SO$_2$-aryl, —SO$_2$-heteroaryl, heterocycloalkyl(C$_1$-C$_6$)alkanoyl, or heteroaryl(C$_1$-C$_6$)alkanoyl, wherein the alkyl portion of the alkyl and alkanoyl groups are optionally substituted with halogen or C$_1$-C$_6$ alkoxy, wherein the aryl, and heteroaryl groups are optionally substituted with alkyl, alkoxy, halogen, haloalkyl, haloalkoxy, wherein R" at each occurrence is independently H, or C$_1$-C$_6$ alkyl, wherein the alkyl group is optionally substituted with halogen, or R$_1$ is C$_3$-C$_7$ cycloalkyl(C$_1$-C$_6$ alkyl) wherein the cyclic portion is optionally substituted with 1, 2, 3, 4, or 5 groups that are independently halogen, C$_1$-C$_6$ alkyl, OH, alkoxycarbonyl, or C$_1$-C$_6$ alkoxy; or R$_1$ is C$_1$-C$_{14}$ alkyl, C$_2$-C$_{16}$ alkenyl, or C$_2$-C$_8$ alkynyl, each of which is optionally substituted with 1 or 2 groups that are independently OH, halogen, C$_1$-C$_6$ alkoxy, aryl, arylalkoxy, aryloxy, heteroaryl, heterocycloalkyl, aryl(C$_1$-C$_6$) alkyl, —CO$_2$—(C$_1$-C$_6$ alkyl), —NR'R", C$_1$-C$_6$ thioalkoxy, —NH—S(O)$_x$—R$_{25}$, —N(C$_1$-C$_6$ alkyl)-S(O)$_x$—R$_{25}$, —S(O)$_x$—R$_{25}$, —C(O)NR$_{30}$R$_{31}$, —N(R$_{16}$)C(O)NR$_{16}$R$_{17}$, or —N(R$_{16}$)C(O)—R$_{17}$;

wherein the above aryl groups are optionally substituted with 1, 2, or 3 groups that are independently OH, C$_1$-C$_6$ alkoxy, C$_1$-C$_6$ alkyl, or halogen;

R$_{30}$ and R$_{31}$ are independently H, C$_1$-C$_6$ alkyl, aryl (preferably phenyl), arylalkyl (preferably benzyl), heteroaryl, heteroarylalkyl, heterocycloalkyl, heterocycloalkylalkyl, arylalkanoyl, alkenyl, cycloalkyl, alkynyl, cycloalkenyl, pyridyl, imidazolyl, thiazolyl, oxazolyl, or indolyl, wherein the alkyl portions of the above are optionally substituted with 1, 2, or 3 groups that are independently NH$_2$, NH(C$_1$-C$_6$ alkyl), N(C$_1$-C$_6$ alkyl)(C$_1$-C$_6$ alkyl), OH, C$_1$-C$_6$ thioalkoxy, heterocycloalkyl, aryl, heteroaryl, CN, halogen, or alkoxy optionally substituted with OH or phenyl, wherein the aryl, heteroaryl and heterocycloalkyl groups are optionally substituted with 1, 2, or 3 groups that are independently C$_1$-C$_4$ alkyl, C$_1$-C$_4$ alkoxy, CF$_3$, OCF$_3$, OH, halogen, thioalkoxy, phenyl or heteroaryl;

or

R$_{30}$, R$_{31}$, and the nitrogen to which they are attached form a heterocycloalkyl ring containing from 3 to 7 ring members, wherein the cyclic portions of R$_{30}$ and R$_{31}$ or the heterocyclic ring formed from R$_{30}$, R$_{31}$, and the nitrogen to which they are attached are optionally substituted with 1, 2, or 3 groups that are independently alkyl, alkoxy, halo, OH, thioalkoxy, NH$_2$, NH(C$_1$-C$_6$ alkyl), N(C$_1$-C$_6$ alkyl)(C$_1$-C$_6$ alkyl), CF$_3$, OCF$_3$, phenyl optionally substituted with a halogen, —(C$_1$-C$_4$ alkyl)-N(H or C$_1$-C$_4$ alkyl)-phenyl, C$_1$-C$_4$ hydroxyalkyl, arylalkoxy, arylalkyl, arylalkanoyl, C(O)NH$_2$, C(O)NH(C$_1$-C$_6$ alkyl), C(O)N(C$_1$-C$_6$ alkyl)(C$_1$-C$_6$ alkyl), heterocycloalkylalkyl, C$_1$-C$_6$ alkoxycarbonyl, C$_2$-C$_6$ alkanoyl, heteroaryl, or —SO$_2$—(C$_1$-C$_6$ alkyl)

x is 0, 1, or 2;

R$_{25}$ is C$_1$-C$_6$ alkyl, OH, NR$_{26}$R$_{27}$;

R$_{26}$ and R$_{27}$ are independently H, C$_1$-C$_6$ alkyl, phenyl (C$_1$-C$_4$ alkyl), aryl, or heteroaryl; or R$_{26}$, R$_{27}$ and the nitrogen to which they are attached form a heterocycloalkyl ring;

R$_1$ is heteroaryl(C$_1$-C$_6$)alkyl wherein the cyclic portion is optionally substituted with 1, 2, 3, 4, or 5 groups that are independently halogen, C$_1$-C$_6$ alkyl, C$_1$-C$_6$ alkoxy, C$_1$-C$_4$ haloalkyl, C$_1$-C$_4$ haloalkoxy, aryl, arylalkyl, aryloxy, heteroaryl, —SO$_2$-aryl, —S(O)$_x$—R$_{25}$, —(C$_1$-C$_4$ alkyl)-S(O)$_x$—R$_{25}$, CN, C$_1$-C$_6$ thioalkoxy, C$_1$-C$_6$ alkoxycarbonyl, —NR'R", —C(O)—NR'R", heterocycloalkyl, wherein the above aryl groups are optionally substituted with 1, 2, 3, or 4 groups that are independently halogen, C$_1$-C$_6$ alkyl, C$_1$-C$_6$ alkoxy, C$_1$-C$_4$ haloalkyl, C$_1$-C$_4$ haloalkoxy, or CN;

wherein the above heteroaryl and heterocycloalkyl groups are optionally substituted with 1, 2, or 3 groups that are independently halogen, CF$_3$, (C$_1$-C$_4$)alkyl, C$_1$-C$_6$ thioalkoxy, OH, C$_1$-C$_4$ hydroxyalkyl, or C$_1$-C$_4$ alkoxy; or R$_1$ is heterocycloalkyl(C$_1$-C$_6$ alkyl) wherein the cyclic portion is optionally substituted with 1, 2, 3, 4, or 5 groups that are independently halogen, C$_1$-C$_6$ alkyl, C$_1$-C$_6$ alkoxy, C$_1$-C$_4$ haloalkyl, C$_1$-C$_4$ haloalkoxy, aryl, arylalkyl, aryloxy, heteroaryl, —SO$_2$-aryl, —S(O)$_x$—R$_{25}$, —(C$_1$-C$_4$ alkyl)-S(O)$_x$—R$_{25}$, CN, C$_1$-C$_6$ thioalkoxy, C$_1$-C$_6$ alkoxycarbonyl, —NR'R", —C(O)—NR'R", heterocycloalkyl;

R$_2$ is H, C$_1$-C$_6$ alkyl, or phenyl(C$_1$-C$_4$)alkyl;

R$_3$ is H, halogen, C$_1$-C$_6$ alkyl, C$_1$-C$_6$ alkoxy, C$_1$-C$_6$ haloalkyl, CN, $R_4$ is H, halogen, $C_1$-$C_6$ alkyl optionally substituted with —$CO_2$—($C_1$-$C_6$ alkyl), $C_1$-$C_6$ alkoxy, $C_1$-$C_6$ haloalkyl, $C_1$-$C_6$ haloalkoxy, CN, aryloxy, isocyanato, —$SO_2$—($C_1$-$C_6$ alkyl), —NHR', —NR'R", $C_1$-$C_6$ alkanoyl, heteroaryl, aryl, or $R_3$ and $R_4$ and the carbons to which they are attached form a heterocycloalkyl ring which is optionally substituted with 1, 2, or 3 groups that are independently $C_1$-$C_4$ alkyl, $C_1$-$C_4$ alkoxy, halogen, or $C_1$-$C_4$ alkanoyl wherein the alkanoyl group is optionally substituted with up to 3 halogen atoms;

$R_{3'}$ is H, —$SO_2$—NR'R", halogen, or $R_4$ and $R_{3'}$ and the carbons to which they are attached form a benzo ring; or $R_4$ and $R_{3'}$ and the carbons to which they are attached form a 1-oxa-2,3-diazacyclopentyl ring;

$R_{10}$ and $R_{11}$ are independently H or F; or $R_{10}$, $R_3$, and the carbons to which they are attached for a 1,2,5-oxadiazolyl ring; or $R_{10}$, $R_3$, and the carbons to which they are attached form a naphthyl ring.

The compounds of Formula I inhibit β-amyloid peptide release and/or its synthesis and, therefore, are useful in the prevention of Alzheimer's Disease (AD) in patients susceptible to AD and/or in the treatment of patients with AD in order to inhibit further deterioration in their condition. The invention also, encompasses pharmaceutical compositions containing the compounds of Formula I, and methods employing such compounds or compositions in the treatment of cognitive diseases, including Alzheimer's disease.

The invention also provides a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, age related macular degeneration or diffuse Lewy body type of Alzheimer's disease and who is in need of such treatment which comprises administration of a therapeutically effective amount of a compound of formula (I).

In another aspect, the invention provides methods of preparing the compounds of interest, as well as intermediates useful in preparing the compounds of interest.

DETAILED DESCRIPTION OF THE INVENTION

In another aspect, the invention provides compounds of formula I-a, i.e., compounds of formula I wherein $R_1$ is phenyl($C_1$-$C_8$ alkyl), naphthyl($C_1$-$C_8$ alkyl), phenyl($C_2$-$C_6$ alkenyl), or naphthyl($C_2$-$C_6$ alkenyl), wherein the cyclic portion of each is optionally substituted with 1, 2, 3, 4, or 5 groups that are independently $C_1$-$C_6$ alkyl, $C_1$-$C_6$ alkoxy, halogen, $CF_3$, $OCF_3$, thiazolyl, oxazolyl, pyrazolyl, thiazolyl($C_1$-$C_6$)alkoxy, pyridyl ($C_1$-$C_6$)alkoxy, phenyl($C_1$-$C_6$ alkanoyl) phenyl($C_1$-$C_4$) alkoxy, oxazolyl($C_1$-$C_4$)alkoxy, pyrazolyl($C_1$-$C_4$) alkoxy, phenyloxy, $C_1$-$C_6$ alkoxycarbonyl, triazolyl, —O—$CH_2CH_2$—O—, —O—$CH_2$—O—, —C(O) $NR_{30}R_{31}$, —NHR', —NR'R", —N($R_{16}$)C(O)—$R_{17}$, morpholinyl, thiomorpholinyl, thiomorpholinyl S,S-dioxide, piperidinyl, pyrrolidinyl, phenyl, CN, —$SO_2$-phenyl, —S(O)$_x$—$R_{25}$, —($C_1$-$C_4$ alkyl)-S(O)$_x$—$R_{25}$, —($C_1$-$C_4$ alkyl)-$SO_2$-phenyl, OH, $C_1$-$C_6$ thioalkoxy, $C_2$-$C_6$ alkenyl, —O—$SO_2$-phenyl, or hydroxyalkyl, wherein the heteroaryl group is optionally substituted with 1, 2, or 3 groups that are independently $C_1$-$C_6$ alkyl, $C_1$-$C_6$ alkoxy, or halogen, wherein the heterocycloalkyl group is optionally substituted with $C_1$-$C_6$ alkyl, $C_1$-$C_6$ alkoxy, or halogen, wherein the above phenyl groups are optionally substituted with 1, 2, 3, 4 or 5 groups that are independently halogen, $C_1$-$C_6$ alkyl, or $C_1$-$C_4$ alkoxy, $R_{16}$ is H or $C_1$-$C_6$ alkyl;

$R_{17}$ is $C_1$-$C_6$ alkyl, phenyl, pyridyl, pyrimidyl, pyridazyl, pyrazinyl, thienyl, oxazolyl, thiazolyl, furanyl, $C_1$-$C_6$ alkoxy, OH, phenyloxy, pyridyloxy, pyrimidyloxy, pyridazyloxy, pyrazinyloxy, thienyloxy, oxazolyloxy, thiazolyloxy, furanyloxy, phenyl ($C_1$-$C_6$)alkoxy, or —$NR_{18}R_{19}$;

$R_{18}$ and $R_{19}$ are independently H, $C_1$-$C_6$ alkyl, phenyl, pyridyl, thienyl, furanyl, piperidinyl, pyrrolidinyl, dioxolanyl, dioxanyl, morpholinyl, thiomorpholinyl, thiomorpholinyl 1,1-dioxide, tetrahydro-thiopyranyl 1,1-dioxide, or phenyl($C_1$-$C_6$) alkyl;

$R_1$ is $C_3$-$C_7$ cycloalkyl($C_1$-$C_6$ alkyl) wherein the cyclic portion is optionally substituted with 1, 2, 3, 4, or 5 groups that are independently halogen, $C_1$-$C_6$ alkyl, OH, alkoxycarbonyl, or $C_1$-$C_6$ alkoxy; or $R_1$ is $C_1$-$C_{14}$ alkyl, $C_2$-$C_{16}$ alkenyl, or $C_2$-$C_6$ alkynyl, each of which is optionally substituted with 1 or 2 groups that are independently OH, halogen, $C_1$-$C_6$ alkoxy, phenyl, naphthyl, pyridyl, phenyl($C_1$-$C_4$)alkoxy, phenyloxy, —$CO_2$—($C_1$-$C_6$ alkyl), —NR'R", $C_1$-$C_6$ thioalkoxy, CN, —NH—S (O)$_x$—$R_{25}$, —N($C_1$-$C_6$ alkyl)-S(O)$_x$—$R_{25}$, —S(O)$_x$—$R_{25}$, —C(O)$NR_{30}R_{31}$, —N($R_{16}$)C(O)$NR_{16}R_{17}$, or —N($R_{16}$)C (O)—$R_{17}$;

wherein the above cyclic portions of the above groups are optionally substituted with 1, 2, 3, or 4 groups that are independently OH, $C_1$-$C_6$ alkoxy, $C_1$-$C_6$ alkyl, or halogen;

$R_{25}$ is $C_1$-$C_6$ alkyl, OH, $NR_{26}R_{27}$;

$R_{26}$ and $R_{27}$ are independently H, $C_1$-$C_6$ alkyl, phenyl ($C_1$-$C_4$ alkyl), phenyl, naphthyl, or pyridyl, pyrimidyl, pyridazyl, pyrazinyl, thienyl, oxazolyl, thiazolyl, furanyl; or $R_{26}$, $R_{27}$ and the nitrogen to which they are attached form a 5, 6, or 7 membered heterocycloalkyl ring;

or $R_1$ is thienyl($C_1$-$C_6$ alkyl), pyridyl($C_1$-$C_6$ alkyl), furanyl($C_1$-$C_6$ alkyl), pyrazolyl($C_1$-$C_6$ alkyl), pyrrolyl($C_1$-$C_6$ alkyl), thiazolyl($C_1$-$C_6$ alkyl), 1,2,3-thiadiazolyl($C_1$-$C_6$ alkyl), 1,2,4-thiadiazolyl($C_1$-$C_6$ alkyl), 1,3,4-oxadiazole($C_1$-$C_6$ alkyl), 1,2,4-oxadiazole($C_1$-$C_6$ alkyl), indolyl($C_1$-$C_6$ alkyl), triazolyl($C_1$-$C_6$ alkyl), imidazolyl($C_1$-$C_6$ alkyl), isoxazolyl($C_1$-$C_6$ alkyl), benzothienyl($C_1$-$C_6$ alkyl), benzofuranyl($C_1$-$C_6$ alkyl), quinolinyl($C_1$-$C_6$ alkyl), imidazo [2,1-b]thiazolyl($C_1$-$C_6$ alkyl), benzo[c][1,2,5]thiadiazolyl ($C_1$-$C_6$ alkyl), benzoimidazolyl($C_1$-$C_6$ alkyl), benzooxazolyl($C_1$-$C_6$ alkyl), benzo[1,2,5]oxadiazolyl($C_1$-$C_6$ alkyl), 1H-indazolyl($C_1$-$C_6$ alkyl), 1H-benzotriazolyl ($C_1$-$C_6$ alkyl), furo[3,2-b]pyridinyl ($C_1$-$C_6$ alkyl), 1H-pyrazolo[3,4-b]pyridinyl($C_1$-$C_6$ alkyl), 1H-pyrazolo [3,4-c]pyridinyl($C_1$-$C_6$ alkyl), quinoxalinyl($C_1$-$C_6$ alkyl), or isoquinolinyl($C_1$-$C_6$ alkyl), wherein the cyclic portions of each of the above are optionally substituted with 1, 2, 3, 4, or 5 groups that are independently halogen, $C_1$-$C_6$ alkyl, $C_1$-$C_6$ alkoxy, $C_1$-$C_4$ haloalkyl, $C_1$-$C_4$ haloalkoxy, phenyl, phenyl($C_1$-$C_6$ alkyl), phenyloxy, pyrazolyl, imidazolyl, furanyl, thienyl, morpholinyl, —$SO_2$-phenyl, —$SO_2$—($C_1$-$C_6$ alkyl), —$S(O)_x$—$R_{25}$, —($C_1$-$C_4$ alkyl)-$S(O)_x$—$R_{25}$, CN, $C_1$-$C_6$ thioalkoxy, $C_1$-$C_6$ alkoxycarbonyl, —NR'R", —C(O)—NR'R", pyridyl, piperidinyl, piperazinyl, pyrrolidinyl, or tetrahydrofuranyl, wherein the above phenyl groups are optionally substituted with 1, 2, 3, or 4 groups that are independently halogen, $C_1$-$C_6$ alkyl, $C_1$-$C_6$ alkoxy, $C_1$-$C_4$ haloalkyl, $C_1$-$C_4$ haloalkoxy, or CN;

wherein the above heteroaryl and heterocycloalkyl groups are optionally substituted with 1, 2, or 3 groups that are independently halogen, $CF_3$, ($C_1$-$C_4$) alkyl, $C_1$-$C_6$ thioalkoxy, or $C_1$-$C_4$ alkoxy;

R' is H, $C_1$-$C_6$ alkyl, $C_3$-$C_8$ cycloalkyl, phenyl, phenyl($C_1$-$C_4$)alkyl, $C_1$-$C_6$ alkanoyl, phenyl($C_1$-$C_6$)alkanoyl, pyridyl($C_1$-$C_4$)alkyl, pyrimidyl($C_1$-$C_4$)alkyl, pyridazyl($C_1$-$C_4$)alkyl, pyrazinyl($C_1$-$C_4$)alkyl, thienyl($C_1$-$C_4$) alkyl, oxazolyl($C_1$-$C_4$)alkyl, thiazolyl($C_1$-$C_4$)alkyl, furanyl($C_1$-$C_4$)alkyl, piperidinyl($C_1$-$C_4$)alkyl, —$SO_2$-alkyl, —$SO_2$-phenyl, —$SO_2$-pyridyl, —$SO_2$-pyrimidyl, —$SO_2$-pyridazyl, —$SO_2$-pyrazinyl, —$SO_2$-thienyl, —$SO_2$-oxazolyl, —$SO_2$-thiazolyl, —$SO_2$-furanyl, pyridyl($C_1$-$C_6$)alkanoyl, pyrimidyl($C_1$-$C_6$)alkanoyl, pyridazyl($C_1$-$C_6$)alkanoyl, pyrazinyl($C_1$-$C_6$)alkanoyl, thienyl($C_1$-$C_6$)alkanoyl, oxazolyl($C_1$-$C_6$)alkanoyl, thiazolyl($C_1$-$C_6$)alkanoyl, or furanyl($C_1$-$C_6$)alkanoyl, wherein the alkyl portion of the alkyl and alkanoyl groups are optionally substituted with halogen or $C_1$-$C_6$ alkoxy, wherein the aryl, and heteroaryl groups are optionally substituted with alkyl, alkoxy, halogen, haloalkyl, haloalkoxy, R" is H, or $C_1$-$C_6$ alkyl, wherein the alkyl group is optionally substituted with halogen, or $R_1$ is 4-oxo-4H-chromenyl($C_1$-$C_6$ alkyl), 2H-chromenyl ($C_1$-$C_6$ alkyl), pyrrolidinonyl dione ($C_1$-$C_6$ alkyl), pyrrolidinonyl($C_1$-$C_6$ alkyl), isoindolyl dione($C_1$-$C_6$ alkyl), 1,3-dioxolanyl($C_1$-$C_6$ alkyl), dioxanyl($C_1$-$C_6$ alkyl), tetrahydropyranyl($C_1$-$C_6$ alkyl), indolinyl ($C_1$-$C_6$ alkyl), 3-oxo-1,3-dihydro-benzo[c]isoxazolyl($C_1$-$C_6$ alkyl), 2-oxo-2,3-dihydro-1H-benzoimidazolyl($C_1$-$C_6$ alkyl), 3-oxo-3,4-dihydro-1H-2-oxa-3lambda4-thia-1,4-diazanaphthyl($C_1$-$C_6$ alkyl), 3,3-dimethyl-3H-indazolyl ($C_1$-$C_6$ alkyl), or piperidinyl($C_1$-$C_6$ alkyl), wherein the cyclic portion of each is optionally substituted with 1, 2, 3, 4, or 5 groups that are independently halogen, $C_1$-$C_6$ alkyl, $C_1$-$C_6$ alkoxy, $C_1$-$C_4$ haloalkyl, $C_1$-$C_4$ haloalkoxy, phenyl, phenyl($C_1$-$C_6$ alkyl), phenyloxy, pyrazolyl, imidazolyl, furanyl, thienyl, morpholinyl, —$SO_2$-phenyl, —$SO_2$—($C_1$-$C_6$ alkyl), —$S(O)_x$—$R_{25}$, —($C_1$-$C_4$ alkyl)-$S(O)_x$—$R_{25}$, CN, $C_1$-$C_6$ thioalkoxy, $C_1$-$C_6$ alkoxycarbonyl, —NR'R", —C(O)—NR'R", pyridyl, piperidinyl, piperazinyl, pyrrolidinyl, or tetrahydrofuranyl, wherein the above phenyl groups are optionally substituted with 1, 2, 3, or 4 groups that are independently halogen, $C_1$-$C_6$ alkyl, $C_1$-$C_6$ alkoxy, $C_1$-$C_4$ haloalkyl, $C_1$-$C_4$ haloalkoxy, or CN;

wherein the above heteroaryl and heterocycloalkyl groups are optionally substituted with 1, 2, or 3 groups that are independently halogen, $CF_3$, ($C_1$-$C_4$) alkyl, $C_1$-$C_6$ thioalkoxy, or $C_1$-$C_4$ alkoxy;

$R_2$ is H, $C_1$-$C_4$ alkyl, or benzyl;

$R_3$ is H, halogen, $C_1$-$C_6$ alkyl, $C_1$-$C_6$ alkoxy, $CF_3$, CN, $R_4$ is H, halogen, $C_1$-$C_6$ alkyl optionally substituted with —$CO_2$—($C_1$-$C_6$ alkyl), $C_1$-$C_6$ alkoxy, $C_1$-$C_6$ haloalkyl, $OCF_3$, CN, phenyloxy, isocyanato, —$SO_2$—($C_1$-$C_6$ alkyl), —NHR', —NR'R", $C_1$-$C_6$ alkanoyl, oxazolyl, pyrazolyl, thiazolyl, pyridyl, furanyl or thienyl, phenyl, or $R_3$ and $R_4$ and the carbons to which they are attached form a piperidinyl or pyrrolidinyl ring which is optionally substituted with 1, 2, or 3 groups that are independently $C_1$-$C_4$ alkyl, $C_1$-$C_4$ alkoxy, halogen, or $C_1$-$C_4$ alkanoyl wherein the alkanoyl group is optionally substituted with up to 3 halogen atoms;

$R_{3'}$ is H, —$SO_2$—NR'R", or halogen;

or $R_4$ and $R_{3'}$ and the carbons to which they are attached form a benzo ring.

Preferred compounds of formula I include those of formula II,

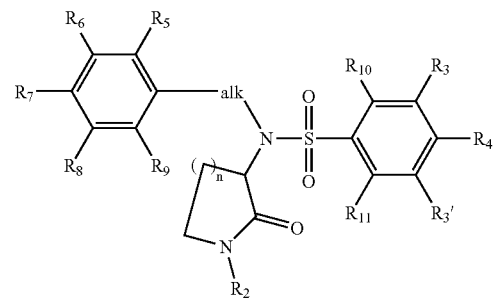

(II)

wherein alk is

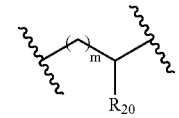

wherein m is 0, 1, 2, 3, 4, 5, or 6;

$R_{20}$ is H or methyl; and the alk group is optionally substituted with phenyl;

$R_5$ is H, $C_1$-$C_6$ alkoxy, $CF_3$, morpholinyl, oxazolyl, pyrazolyl, thiomorpholinyl, thiomorpholinyl S,S-dioxide, piperidinyl, pyrrolidinyl, halogen, $C_1$-$C_6$ alkyl, phenyl optionally substituted with 1, 2, 3, 4 or 5 groups that are independently halogen, $C_1$-$C_6$ alkyl, or $C_1$-$C_4$ alkoxy, morpholin-4-yl, phenyl, —O—($CH_2$)—C(O)O—($CH_2CH_3$), CN, —($C_1$-$C_4$ alkyl)-$SO_2$-phenyl, $R_6$ is H, $C_1$-$C_6$ alkoxy, halogen, $C_1$-$C_6$ alkyl, $C_1$-$C_6$ alkoxy, $CF_3$, $OCF_3$, phenyl($C_1$-$C_4$)alkoxy, phenyloxy, $C_1$-$C_6$ alkoxycarbonyl, CN, $C_2$-$C_6$ alkenyl, wherein the above phenyl groups are optionally substituted with 1, 2, 3, 4 or 5 groups that are independently halogen, $C_1$-$C_6$ alkyl, $C_2$-$C_6$ alkenyl, $C_1$-$C_4$ alkoxy, $C_1$-$C_4$ alkoxycarbonyl, or benzyloxy; or $R_5$, $R_6$, and the carbons to which they are attached form a benzo ring, which is optionally substituted with 1 or 2 groups that are independently halogen, $C_1$-$C_4$ alkyl, $C_1$-$C_4$ alkoxy, $CF_3$, or $OCF_3$;

$R_7$ is H, OH, $C_1$-$C_6$ alkoxy, $CO_2H$, haloalkyl, CN, triazolyl, tetrazolyl, $NO_2$, phenyl($C_1$-$C_6$ alkanoyl),

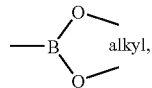

—O—$SO_2$-phenyl, —S(O)$_x$—$R_{25}$, —($C_1$-$C_4$ alkyl)-S(O)$_x$—$R_{25}$, halogen, $C_1$-$C_6$ alkyl, phenyloxy, $CF_3$, $C_1$-$C_6$ alkoxycarbonyl, —($C_1$-$C_4$ alkyl)-C(O)$NR_{30}R_{31}$, —O—($C_1$-$C_4$ alkyl)-C(O)$NR_{30}R_{31}$, —NHR', —NR'R'', pyridyl, oxazolyl, oxadiazolyl, —N($R_{16}$)C(O)—$R_{17}$, thiazolyl($C_1$-$C_6$)alkoxy, pyridyl($C_1$-$C_6$)alkoxy, oxazolyl ($C_1$-$C_4$)alkoxy, or pyrazolyl ($C_1$-$C_4$)alkoxy, wherein the cyclic portions of the above are optionally substituted with 1, 2, or 3 groups that are independently $C_1$-$C_6$ alkyl, $C_1$-$C_6$ alkoxy, $C_1$-$C_4$ alkoxy $C_1$-$C_4$ alkyl, pyridyl, pyrrolyl, imidazolyl, furanyl, thienyl optionally substituted with 1 or 2 methyls, halogen, $C_3$-$C_6$ cycloalkyl(in one aspect, cyclohexyl) or phenyl optionally substituted with 1, 2, 3, 4 or 5 groups that are independently halogen, OH, $C_1$-$C_6$ alkyl, $C_1$-$C_4$ alkoxy, $CF_3$, $OCF_3$, CN, or $C_1$-$C_6$ thioalkoxy, or $R_7$ is methoxycarbonyl, methoxy, ethoxy, isopropoxy, ethoxy substituted with thiazol-5-yl, wherein the thiazolyl ring is substituted with methyl, —$SCH_3$, methyl, isopropyl, tert-butyl, isobutyl, F, Br, Cl, $CF_3$, $OCF_3$, cyano, $N(CH_3)_2$, $N(C_2$ alkyl substituted with Cl) ($C_2$ alkyl substituted with Cl), phenyl, phenyl substituted with methyl, benzyloxy, $NO_2$, —S(O)—$C_1$-$C_6$ alkyl, —$SO_2$—$C_1$-$C_6$ alkyl, $NH_2$, NH($C_1$-$C_6$ alkyl), N($C_1$-$C_6$ alkyl)($C_1$-$C_6$ alkyl), —N($R_{16}$)C(O)$R_{17}$, —C(O)$NR_{30}R_{31}$, $C_1$-$C_2$ haloalkyl, phenyloxy, —O—$SO_2$—(4-chlorophenyl), —NH—C(O)—$CH_3$, —O—C(O)—$CH_3$, thiazolyl substituted with tert-butyl, or OH; wherein $R_{30}$ and $R_{31}$ are independently H, $C_1$-$C_6$ alkyl, phenyl, phenyl $C_1$-$C_6$ alkyl, benzyl, phenylalkanoyl, $C_2$-$C_6$ alkenyl, $C_3$-$C_6$ cycloalkyl, alkynyl, cycloalkenyl, piperidinyl optionally substituted with $C_1$-$C_4$ alkyl or $C_2$-$C_6$ alkanoyl, pyridyl $C_1$-$C_6$ alkyl, pyrazolyl $C_1$-$C_6$ alkyl, $C_2$-$C_6$ alkynyl, tetrahydronaphthyl, tetrahydrofuranyl, dihydrofuranonyl, cyclohexenyl, pyrrolidinyl, pyrazolyl, naphthyl, quinuclidinyl, 4H-pyranonyl(preferably 3-hydroxy 4H-pyranonyl), 1,4-dioxanyl, tetrahydronaphthyl $C_1$-$C_6$ alkyl, tetrahydrofuranyl $C_1$-$C_6$ alkyl, cyclohexenyl $C_1$-$C_6$ alkyl, pyrrolidinyl $C_1$-$C_6$ alkyl, pyrazolyl $C_1$-$C_6$ alkyl, naphthyl $C_1$-$C_6$ alkyl, quinuclidinyl $C_1$-$C_6$ alkyl, 4H-pyranonyl $C_1$-$C_6$ alkyl(preferably 3-hydroxy 4H-pyranonyl $C_1$-$C_6$ alkyl), pyrazinyl $C_1$-$C_6$ alkyl, pyrrolidinyl $C_1$-$C_6$ alkyl, furanyl $C_1$-$C_6$ alkyl, thienyl $C_1$-$C_6$ alkyl, pyrrolyl $C_1$-$C_6$ alkyl, 2,5-dihydro-1H-pyrrolyl $C_1$-$C_6$ alkyl, thiazolyl $C_1$-$C_6$ alkyl, biphenyl $C_1$-$C_6$ alkyl, benzothienyl $C_1$-$C_6$ alkyl, furanyl $C_1$-$C_6$ alkyl, isoxazolyl $C_1$-$C_6$ alkyl, 1,4-dioxanyl $C_1$-$C_6$ alkyl, pyridyl, imidazolyl, thiazolyl, oxazolyl, or indolyl,
wherein the alkyl portions of the above are optionally substituted with 1, 2, or 3 groups that are independently $NH_2$, NH($C_1$-$C_6$ alkyl), N($C_1$-$C_6$ alkyl) ($C_1$-$C_6$ alkyl), OH, phenyl, $C_1$-$C_6$ thioalkoxy, CN, halogen, or alkoxy optionally substituted with OH or phenyl; or $R_{30}$, $R_{31}$, and the nitrogen to which they are attached form a heterocycloalkyl ring that is pyrrolidinyl, piperidinyl, morpholinyl, dihydro 1H-indolyl, tetrahydroisoquinolinyl, thiomorpholinyl, thiomorpholinyl, S,S-dioxide, tetrahydroquinolinyl, or piperazinyl, wherein the cyclic portions of $R_{30}$ and $R_{31}$ or the heterocyclic ring formed from $R_{30}$, $R_{31}$, and the nitrogen to which they are attached are optionally substituted with 1, 2, or 3 groups that are independently alkyl, alkoxy, halo, thioalkoxy, OH, $NH_2$, NH($C_1$-$C_6$ alkyl), N($C_1$-$C_6$ alkyl) ($C_1$-$C_6$ alkyl), $CF_3$, $OCF_3$, phenyl, 4-halophenyl, —($C_1$-$C_4$ alkyl)-N(H or $C_1$-$C_4$ alkyl)-phenyl, $C_1$-$C_4$ hydroxyalkyl, phenylalkoxy, phenylalkyl, phenylalkanoyl, —($C_1$-$C_4$ alkyl)-pyrrolidinyl, C(O)$NH_2$, C(O)NH($C_1$-$C_6$ alkyl), C(O)N($C_1$-$C_6$ alkyl) ($C_1$-$C_6$ alkyl), $C_1$-$C_6$ alkoxycarbonyl, $C_2$-$C_6$ alkanoyl, pyrazolyl, pyrrolyl, pyridyl, furanyl, morpholinyl, or —$SO_2$—($C_1$-$C_6$ alkyl);

R' is H, $C_1$-$C_6$ alkyl, or $C_1$-$C_6$ alkanoyl, wherein the alkyl portion of the alkyl and alkanoyl groups are optionally substituted with halogen, R'' is H or $C_1$-$C_6$ alkyl, wherein the alkyl group is optionally substituted with halogen;

$R_{16}$ is H or $C_1$-$C_6$ alkyl;

$R_{17}$ is $C_1$-$C_6$ alkyl, phenyl, pyridyl, pyrimidyl, pyridazyl, pyrazinyl, thienyl, $C_1$-$C_6$ alkoxy, OH, phenyloxy, pyridyloxy, pyrimidyloxy, pyridazyloxy, pyrazinyloxy, thienyloxy, phenyl($C_1$-$C_4$)alkoxy, phenyl $C_1$-$C_6$ alkyl, thienyl $C_1$-$C_6$ alkyl, $C_3$-$C_6$ cycloalkyl, or phenyl $C_1$-$C_6$ alkyl, or —$NR_{18}R_{19}$,
wherein the cyclic portions of each of the above are optionally substituted with 1, 2, 3, 4, or 5 groups that are independently alkyl, alkoxy, halo, $CF_3$, $OCF_3$, CN, $NH_2$, NH(alkyl), N(alkyl) (alkyl), $CO_2H$, or $C_1$-$C_6$ alkoxycarbonyl;

$R_{18}$, and $R_{19}$ are independently H, $C_1$-$C_6$ alkyl, phenyl, pyridyl, thienyl, piperidinyl, pyrrolidinyl, morpholinyl, thiomorpholinyl, thiomorpholinyl 1,1-dioxide, tetrahydro-thiopyranyl 1,1-dioxide, isoxazolyl or phenyl($C_1$-$C_4$)alkyl, wherein the cyclic portions of each are optionally substituted with 1, 2, or 3 groups that are independently alkyl, alkoxy, halogen, hydroxyl, $CF_3$, or $OCF_3$; or $R_6$, $R_7$, and the carbons to which they are attached form a benzo ring, which is optionally substituted with 1 or 2 groups that are independently halogen, $C_1$-$C_4$ alkyl, $C_1$-$C_4$ alkoxy, $CF_3$, or $OCF_3$;

$R_8$ is H, halogen, $C_1$-$C_6$ alkoxy, $C_1$-$C_6$ alkyl, or $R_7$ and $R_8$ are —O—$CH_2CH_2$—O—, or —O—$CH_2$—O—;

$R_9$ is H, halogen, $C_1$-$C_6$ alkoxy, $C_1$-$C_6$ alkyl, or CN.

In another aspect, the invention provides compounds of formula II-a, i.e., compounds of formula II wherein $R_2$, $R_{10}$ and $R_{11}$ are simultaneously H.

In another aspect, the invention provides compounds of formula II-b, i.e., compounds of formula II-a wherein
$R_3$ is H, halogen, $C_1$-$C_4$ alkyl, $C_1$-$C_4$ alkoxy, $CF_3$, or CN,
$R_4$ is halogen, $C_1$-$C_4$ alkoxy, $C_1$-$C_4$ alkyl, $CF_3$, $OCF_3$, CN, —NHR', —NR'R'', or $C_1$-$C_4$ alkanoyl,
$R_3$' is H, —$SO_2$—NR'R'', or halogen; or
$R_4$ and $R_3$' and the carbons to which they are attached form a benzo ring.

In another aspect, the invention provides compounds of formula II-c, i.e., compounds of formula II-b wherein
$R_6$ is H, $C_1$-$C_6$ alkoxy, halogen, $CF_3$, $OCF_3$, benzyloxy, phenyloxy, $C_1$-$C_4$ alkoxycarbonyl, $C_1$-$C_4$ alkyl, CN, $C_2$-$C_6$ alkenyl,
wherein the above phenyl groups are optionally substituted with 1, 2, 3, 4 or 5 groups that are independently halogen, $C_1$-$C_6$ alkyl, or $C_1$-$C_4$ alkoxy, $R_7$ is H, OH, $C_1$-$C_6$ alkoxy, halogen, $C_1$-$C_4$ alkyl, $CF_3$, $C_1$-$C_4$ alkoxycarbonyl, —C(O)$NR_{30}R_{31}$, —NHR', —NR'R'', —N($R_{16}$)C(O)—$R_{17}$, phenyl optionally substituted with 1, 2, 3, 4 or 5 groups that are independently halogen, $C_1$-$C_6$ alkyl, or $C_1$-$C_4$ alkoxy, $OCF_3$, CN, $C_1$-$C_4$ thioalkoxy, $R_{16}$ is H or $C_1$-$C_6$ alkyl;

$R_{17}$ is $C_1$-$C_6$ alkyl, phenyl, pyridyl, pyrimidyl, thienyl, $C_1$-$C_6$ alkoxy, OH, phenyloxy, pyridyloxy, pyrimidyloxy, thienyloxy, phenyl($C_1$-$C_4$)alkoxy, or —$NR_{18}R_{19}$;

$R_{18}$ and $R_{19}$ are independently H, $C_1$-$C_6$ alkyl, phenyl, pyridyl, thienyl, piperidinyl, pyrrolidinyl, morpholinyl, thiomorpholinyl, thiomorpholinyl 1,1-dioxide, tetrahydro-thiopyranyl 1,1-dioxide, or phenyl($C_1$-$C_4$)alkyl;

$R_{30}$ and $R_{31}$ are independently H, $C_1$-$C_6$ alkyl, phenyl, benzyl, pyridyl, thiazolyl, oxazolyl, or indolyl, or $R_{30}$, $R_{31}$, and the nitrogen to which they are attached form a azepanyl, piperidinyl, pyrrolidinyl, morpholinyl, thiomorpholinyl, or thiomorpholinyl 1,1-dioxide, or $R_6$, $R_7$, and the carbons to which they are attached form a benzo ring, which is optionally substituted with 1 or 2 groups that are independently halogen, $C_1$-$C_4$ alkyl, $C_1$-$C_4$ alkoxy, $CF_3$, or $OCF_3$;

$R_8$ is H, halogen, $C_1$-$C_6$ alkoxy, $C_1$-$C_6$ alkyl, or $R_7$ and $R_8$ are —O—$CH_2CH_2$—O—, or —O—$CH_2$—O—; and $R_9$ is H, halogen, $C_1$-$C_2$ alkoxy, $C_1$-$C_2$ alkyl.

In another aspect, the invention provides compounds of formula II-d, i.e., compounds of formula II-b wherein $R_7$ is thiazolyl($C_1$-$C_6$)alkoxy, phenyloxy, —O—$SO_2$-phenyl, pyridyl($C_1$-$C_6$)alkoxy, oxazolyl($C_1$-$C_4$)alkoxy, pyrazolyl ($C_1$-$C_4$)alkoxy, wherein the thiazolyl, pyridyl, oxazolyl, and pyrazolyl groups are optionally substituted with 1, 2, or 3 groups that are independently $C_1$-$C_4$ alkyl, $C_1$-$C_4$ alkoxy, $C_1$-$C_4$ thioalkoxy, or halogen;

the phenyl groups are optionally substituted with 1, 2, 3, 4 or 5 groups that are independently halogen, $C_1$-$C_6$ alkyl, or $C_1$-$C_4$ alkoxy, $OCF_3$, CN, $C_1$-$C_4$ thioalkoxy, or $R_8$ is H, halogen, $C_1$-$C_6$ alkoxy, $C_1$-$C_6$ alkyl;

$R_7$ and $R_8$ are —O—$CH_2CH_2$—O—, or —O—$CH_2$—O—;

$R_9$ is H, halogen, $C_1$-$C_2$ alkoxy, $C_1$-$C_2$ alkyl.

In another aspect, the invention provides compounds of formula II-e, i.e., compounds of formula II-c wherein $R_4$ is halogen, $C_1$-$C_4$ alkoxy (in one aspect, methoxy or ethoxy), $C_1$-$C_4$ alkyl (in one aspect, methyl), $CF_3$, $OCF_3$, CN, —NHR', or $C_1$-$C_4$ thioalkoxy (in one aspect, thiomethoxy or thioethoxy); and $R_6$, $R_7$, and the carbons to which they are attached form a benzo ring, which is optionally substituted with 1 or 2 groups that are independently halogen, $C_1$-$C_4$ alkyl, $C_1$-$C_4$ alkoxy, $CF_3$, or $OCF_3$. In another aspect, the phenyl ring is unsubstituted.

In another aspect, the invention provides compounds of formula II-f, i.e., compounds of formula II-c wherein $R_6$ and $R_8$ are independently H, $C_1$-$C_4$ alkyl, halogen, $C_2$-$C_6$ alkenyl $C_1$-$C_4$ alkoxy, or phenyloxy wherein the phenyl is optionally substituted with 1, 2, 3, 4 or 5 groups that are independently halogen, $C_1$-$C_4$ alkyl, or $C_1$-$C_4$ alkoxy; and $R_7$ is H, OH, $C_1$-$C_4$ alkoxy, halogen, $C_1$-$C_4$ alkyl, $CF_3$, $C_1$-$C_4$ alkoxycarbonyl, —C(O)$NR_{30}R_{31}$, —NHR', —NR'R", —N($R_{16}$)C(O)—$R_{17}$, $OCF_3$, CN, $C_1$-$C_4$ thioalkoxy.

In another aspect, the invention provides compounds of formula II-g, i.e., compounds of formula II-f wherein $R_4$ and $R_3$, and the carbons to which they are attached form a benzo ring.

In another aspect, the invention provides compounds of formula II-h, i.e., compounds of formulas II-f, or II-g wherein $R_5$, $R_6$, $R_8$, and $R_9$ are H.

In another aspect, the invention provides compounds of formula II-i, i.e., compounds of formulas II-c, II-f, or II-g wherein $R_5$ is H, F or Cl; and $R_6$ is H, CN, methyl, $C_2$-$C_4$ alkenyl, or phenyloxy wherein the phenyl is optionally substituted with 1, 2, 3, 4 or 5 groups that are independently halogen, $C_1$-$C_4$ alkyl, or $C_1$-$C_4$ alkoxy.

In another aspect, the invention provides compounds of formula II-j, i.e., compounds of formulas II-c, II-f, II-g, II-h, or II-i wherein alk is —$CH_2$—, or —$CH(CH_3)$—.

In another aspect, the invention provides compounds of formula II-k, i.e., compounds of formulas II-f, II-g, II-h, or II-i wherein $R_7$ is —C(O)$NR_{30}R_{31}$.

In another aspect, the invention provides compounds of formula II-l, i.e., compounds of formula II-c wherein n is 3;

$R_3$ is H, halogen, $C_1$-$C_3$ alkyl, $C_1$-$C_3$ alkoxy, $CF_3$, or CN, $R_4$ is halogen, $C_1$-$C_4$ alkoxy, $CF_3$, $OCF_3$, CN, —NHR', —NR'R", or $C_1$-$C_4$ alkanoyl, $R_{3'}$ is H, or halogen; or $R_4$ and $R_{3'}$ and the carbons to which they are attached form a benzo ring; and $R_7$ and $R_8$ are —O—$CH_2CH_2$—O—, or —O—$CH_2$—O—.

In another aspect, the invention provides compounds of formula II-m, i.e., compounds of formula II-l wherein $R_4$ is F, Cl, Br, I or methyl. In another aspect, $R_4$ is Cl or Br. In still another aspect, at least one of $R_3$ and $R_{3'}$ is H. In yet another aspect, $R_4$ if F or Cl. Still more preferably, $R_4$ is F or Cl and $R_3$, $R_{3'}$, $R_{10}$, and $R_{11}$ are all H.

In another aspect, the invention provides compounds of formula II-n, i.e., compounds of formula II-l wherein $R_4$ and $R_{3'}$ and the carbons to which they are attached form a benzo ring.

In another aspect, the invention provides compounds of formula II-o, i.e., compounds of formulas II-l, II-m, or II-n wherein $R_3$ is H, F, Cl, $C_1$-$C_2$ alkyl, $C_1$-$C_2$ alkoxy, $CF_3$, or CN.

In another aspect, the invention provides compounds of formula II-p, i.e., compounds of formulas II-l, II-m, II-n, or II-o wherein alk is —$CH_2$—, or —$CH(CH_3)$—.

In another aspect, the invention provides compounds of formula II-q, i.e., compounds of formula II wherein $R_5$ is H;

$R_6$, $R_7$ together are —O—$CH_2$—O—, or —O—$CH_2CH_2$—O—; or $R_6$ and $R_7$ together form a phenyl group which is optionally substituted with methoxy;

$R_8$ is H; and $R_9$ is H.

In another aspect, the invention provides compounds of formula II-r, i.e., compounds of formula II-q wherein $R_4$ is methyl, F, Cl or $CF_3$. In another aspect, $R_3$ is H. In still another aspect, $R_{3'}$ is also H. In yet still another aspect, $R_2$, $R_{10}$, and $R_{11}$ are H. In yet another aspect, $R_4$ is F or Cl. In still another aspect, $R_4$ is Cl.

In another aspect, the invention provides compounds of formula II-s, i.e., compounds of formula II-q wherein $R_4$ is H. In another aspect, at least one of $R_3$ and $R_{3'}$ is not H. In another aspect, neither of $R_3$ nor $R_{3'}$ is H.

In still yet another aspect, the invention provides compounds of formula II-t, i.e., compounds of formula II-c, wherein R5, R6, R7, R8, and R9 are all independently halogen. In another aspect, the halogens are the same. In still another aspect, the halogen is F.

Other preferred compounds of formulas I or I-a are those of formula III

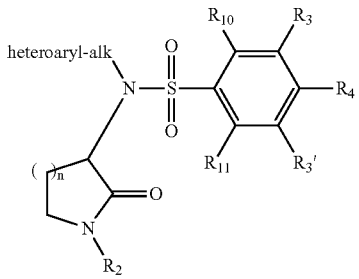

alk is

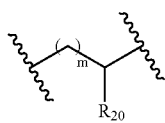

wherein
m is 0, 1, 2, 3, 4, 5, or 6;
$R_{20}$ is H or methyl;
heteroaryl is thienyl, pyridyl, furanyl, pyrazolyl, pyrrolyl, thiazolyl, 1,2,3-thiadiazolyl, indolyl, triazolyl, benzothienyl, benzofuranyl, quinolinyl, or imidazo[2,1-b]thiazolyl, each of which is optionally substituted with 1, 2, 3, 4, or 5 groups that are independently halogen, $C_1$-$C_6$ alkyl, phenyl, phenyl($C_1$-$C_6$ alkyl), phenyloxy, pyrazolyl, imidazolyl, furanyl, thienyl, —$SO_2$-phenyl, CN, $C_1$-$C_6$ thioalkoxy, $C_1$-$C_6$ alkoxycarbonyl, —NR'R", piperidinyl, piperazinyl, pyrrolidinyl, or tetrahydrofuranyl,
wherein the above phenyl groups are optionally substituted with 1, 2, 3, or 4 groups that are independently halogen, $C_1$-$C_6$ alkyl, $C_1$-$C_6$ alkoxy, or CN;
wherein the pyrazolyl, imidazolyl, furanyl, and thienyl groups are optionally substituted with 1, 2, or 3 groups that are independently halogen, $CF_3$, or ($C_1$-$C_4$)alkyl;
wherein R' is H, $C_1$-$C_6$ alkyl, or $C_1$-$C_6$ alkanoyl, wherein the alkyl portion of the alkyl and alkanoyl groups are optionally substituted with halogen,
wherein R" is H, or $C_1$-$C_6$ alkyl, wherein the alkyl group is optionally substituted with halogen.

In another aspect, the invention provides compounds of formula III-a, i.e., compounds of formula III wherein
$R_2$ is H, methyl, or benzyl; and
$R_{10}$ and $R_{11}$ are simultaneously H.

In another aspect, the invention provides compounds of formula III-b, i.e., compounds of formula III-a wherein
$R_3$ is H, halogen, $C_1$-$C_4$ alkyl, $C_1$-$C_4$ alkoxy, $CF_3$, or CN,
$R_4$ is halogen, $C_1$-$C_4$ alkoxy, $C_1$-$C_4$ alkyl, $CF_3$, $OCF_3$, CN, —NHR', —NR'R", or $C_1$-$C_4$ alkanoyl, and
$R_{3'}$ is H, —$SO_2$—NR'R", or halogen; or
$R_4$ and $R_{3'}$ and the carbons to which they are attached form a benzo ring.

In another aspect, the invention provides compounds of formula III-c, i.e., compounds of formula III-b wherein $R_4$ is halogen, methoxy, methyl, $CF_3$, $OCF_3$, or CN; and
$R_{3'}$ is H, or halogen.

In another aspect, the invention provides compounds of formula III-d, i.e., compounds of formula III-c wherein m is 0, 1, 2, 3, or 4;
heteroaryl is thienyl, pyridyl, furanyl, pyrazolyl, pyrrolyl, thiazolyl, 1,2,3-thiadiazolyl, or triazolyl, each of which is optionally substituted with 1, 2, or 3 groups that are independently halogen, $C_1$-$C_6$ alkyl, phenyl, phenyl($C_1$-$C_4$ alkyl), phenyloxy, pyrazolyl, imidazolyl, furanyl, thienyl, —$SO_2$-phenyl, CN, $C_1$-$C_4$ thioalkoxy, $C_1$-$C_4$ alkoxycarbonyl, —NR'R", piperidinyl, wherein
the above phenyl groups are optionally substituted with 1, 2, 3, or 4 groups that are independently halogen, $C_1$-$C_6$ alkyl, $C_1$-$C_6$ alkoxy, or CN;
the pyrazolyl, imidazolyl, furanyl, and thienyl groups are optionally substituted with 1, 2, or 3 groups that are independently halogen, $CF_3$, or ($C_1$-$C_4$)alkyl.

In another aspect, the invention provides compounds of formula III-e, i.e., compounds of formula III-d wherein
m is 0, 1, or 2;
heteroaryl is thienyl, pyridyl, furanyl, pyrazolyl, pyrrolyl, thiazolyl, 1,2,3-thiadiazolyl, or triazolyl, wherein each is optionally substituted with 1, 2, or 3 groups that are independently halogen, $C_1$-$C_6$ alkyl, phenyl, benzyl, phenyloxy, pyrazolyl, —$SO_2$-phenyl, CN, $C_1$-$C_4$ thioalkoxy, $C_1$-$C_4$ alkoxycarbonyl, —NR'R", piperidinyl, wherein
the above phenyl groups are optionally substituted with 1, 2, 3, or 4 groups that are independently halogen, $C_1$-$C_6$ alkyl, $C_1$-$C_6$ alkoxy, or CN;
the pyrazolyl, is optionally substituted with 1, or 2, or 3 groups that are independently halogen, $CF_3$, or ($C_1$-$C_4$) alkyl.

In another aspect, the invention provides compounds of formula III-f, i.e., compounds of formula III-e wherein
m is 0;
heteroaryl is thienyl, pyridyl, furanyl, pyrazolyl, pyrrolyl, thiazolyl, or triazolyl, wherein each is optionally substituted with 1, 2, or 3 groups that are independently halogen, $C_1$-$C_6$ alkyl, phenyl, benzyl, phenyloxy, pyrazolyl, —$SO_2$-phenyl, CN, $C_1$-$C_4$ thioalkoxy, $C_1$-$C_4$ alkoxycarbonyl, —NR'R", piperidinyl, wherein
the above phenyl groups are optionally substituted with 1, 2, 3, or 4 groups that are independently halogen, $C_1$-$C_6$ alkyl, $C_1$-$C_6$ alkoxy, or CN;
the pyrazolyl, is optionally substituted with 1, or 2, or 3 groups that are independently halogen, $CF_3$, or ($C_1$-$C_4$) alkyl.

In another aspect, the invention provides compounds of formula III-f1, i.e., compounds of formula III-e wherein
m is 2;
heteroaryl is thienyl, pyridyl, furanyl, pyrazolyl, pyrrolyl, thiazolyl, or triazolyl, wherein each is optionally substituted with 1, 2, or 3 groups that are independently halogen, $C_1$-$C_6$ alkyl, phenyl, benzyl, phenyloxy, pyrazolyl, —$SO_2$-phenyl, CN, $C_1$-$C_4$ thioalkoxy, $C_1$-$C_4$ alkoxycarbonyl, —NR'R", piperidinyl, wherein
the above phenyl groups are optionally substituted with 1, 2, 3, or 4 groups that are independently halogen, $C_1$-$C_6$ alkyl, $C_1$-$C_6$ alkoxy, or CN;
the pyrazolyl, is optionally substituted with 1, or 2, or 3 groups that are independently halogen, $CF_3$, or ($C_1$-$C_4$) alkyl.

In another aspect, the invention provides compounds of formula III-g, i.e., compounds according to anyone of formulas III, III-a, III-b, III-c, III-d, III-e, III-f, or III-f1 wherein n is 1. In another aspect, n is 2. In still another aspect, n is 3.

In another aspect, the invention provides compounds of formula III-h, i.e., compounds according to formula III-b wherein
m is 0, 1, 2, or 3;

heteroaryl is indolyl, benzothienyl, benzofuranyl, quinolinyl, or imidazo[2,1-b]thiazolyl, wherein each is optionally substituted with 1, 2, or 3 groups that are independently halogen, $C_1$-$C_6$ alkyl, phenyl, benzyl, phenyloxy, pyrazolyl, —$SO_2$-phenyl, CN, $C_1$-$C_4$ thioalkoxy, $C_1$-$C_4$ alkoxycarbonyl, —NR'R", piperidinyl, wherein the above phenyl groups are optionally substituted with 1, 2, 3, or 4 groups that are independently halogen, $C_1$-$C_6$ alkyl, $C_1$-$C_6$ alkoxy, or CN;

the pyrazolyl, is optionally substituted with 1, or 2, or 3 groups that are independently halogen, $CF_3$, or ($C_1$-$C_4$) alkyl.

In another aspect, the invention provides compounds of formula III-i, i.e., compounds according to formula III-h wherein m is 0 or 1;

heteroaryl is indolyl, benzothienyl, benzofuranyl, quinolinyl, or imidazo[2,1-b]thiazolyl, wherein each is optionally substituted with 1, 2, or 3 groups that are independently halogen, $C_1$-$C_6$ alkyl, phenyl, benzyl, phenyloxy, pyrazolyl, —$SO_2$-phenyl, CN, $C_1$-$C_4$ thioalkoxy, $C_1$-$C_4$ alkoxycarbonyl, —NR'R", piperidinyl, wherein the above phenyl groups are optionally substituted with 1, 2, 3, or 4 groups that are independently halogen, $C_1$-$C_6$ alkyl, $C_1$-$C_6$ alkoxy, or CN;

the pyrazolyl, is optionally substituted with 1, or 2, or 3 groups that are independently halogen, $CF_3$, or ($C_1$-$C_4$) alkyl.

In another aspect, the invention provides compounds of formula III-i, i.e., compounds according to formula III-h wherein m is 2;

heteroaryl is indolyl, benzothienyl, benzofuranyl, quinolinyl, or imidazo[2,1-b]thiazolyl, wherein each is optionally substituted with 1, 2, or 3 groups that are independently halogen, $C_1$-$C_6$ alkyl, phenyl, benzyl, phenyloxy, pyrazolyl, —$SO_2$-phenyl, CN, $C_1$-$C_4$ thioalkoxy, $C_1$-$C_4$ alkoxycarbonyl, —NR'R", piperidinyl, wherein the above phenyl groups are optionally substituted with 1, 2, 3, or 4 groups that are independently halogen, $C_1$-$C_6$ alkyl, $C_1$-$C_6$ alkoxy, or CN;

the pyrazolyl, is optionally substituted with 1, or 2, or 3 groups that are independently halogen, $CF_3$, or ($C_1$-$C_4$) alkyl.

In another aspect, the invention provides compounds of formula III-i1, i.e., compounds according to formula III-b, wherein $R_1$ is benzoimidazolyl($C_1$-$C_6$ alkyl), benzooxazolyl($C_1$-$C_6$ alkyl), benzo[1,2,5]oxadiazolyl($C_1$-$C_6$ alkyl), 1H-indazolyl($C_1$-$C_6$ alkyl), 1H-benzotriazolyl($C_1$-$C_6$ alkyl), furo[3,2-b]pyridinyl($C_1$-$C_6$ alkyl), 1H-pyrazolo[3,4-b]pyridinyl($C_1$-$C_6$ alkyl), 1H-pyrazolo[3,4-c]pyridinyl($C_1$-$C_6$ alkyl), quinoxalinyl($C_1$-$C_6$ alkyl), or isoquinolinyl($C_1$-$C_6$ alkyl), wherein the cyclic portions of each of the above are optionally substituted with 1, 2, or 3 groups that are independently halogen, $C_1$-$C_6$ alkyl, $C_1$-$C_6$ alkoxy, $CF_3$, $OCF_3$, phenyl, phenyl($C_1$-$C_6$ alkyl), phenyloxy, pyrazolyl, imidazolyl, furanyl, thienyl, morpholinyl, —$SO_2$-phenyl, —$SO_2$—($C_1$-$C_6$ alkyl), —$S(O)_x$—$R_{25}$,—($C_1$-$C_4$ alkyl)-$S(O)_x$—$R_{25}$, CN, $C_1$-$C_6$ thioalkoxy, $C_1$-$C_6$ alkoxycarbonyl, pyridyl, piperidinyl, piperazinyl, pyrrolidinyl, or tetrahydrofuranyl, wherein the above phenyl groups are optionally substituted with 1, 2, 3, or 4 groups that are independently halogen, $C_1$-$C_6$ alkyl, $C_1$-$C_6$ alkoxy, $C_1$-$C_4$ haloalkyl, $C_1$-$C_4$ haloalkoxy, or CN;

wherein the above heteroaryl and heterocycloalkyl groups are optionally substituted with 1, 2, or 3 groups that are independently halogen, $CF_3$, ($C_1$-$C_4$) alkyl, $C_1$-$C_6$ thioalkoxy, or $C_1$-$C_4$ alkoxy.

In another aspect, the invention provides compounds of formula III-i2, i.e., compounds according to formula III-i1, wherein $R_1$ is benzoimidazolyl($C_1$-$C_6$ alkyl), benzooxazolyl($C_1$-$C_6$ alkyl), benzo[1,2,5]oxadiazolyl($C_1$-$C_6$ alkyl), 1H-indazolyl($C_1$-$C_6$ alkyl), 1H-benzotriazolyl($C_1$-$C_6$ alkyl), furo[3,2-b]pyridinyl($C_1$-$C_6$ alkyl), 1H-pyrazolo[3,4-b]pyridinyl($C_1$-$C_6$ alkyl), 1H-pyrazolo[3,4-c]pyridinyl($C_1$-$C_6$ alkyl), quinoxalinyl($C_1$-$C_6$ alkyl), or isoquinolinyl($C_1$-$C_6$ alkyl), wherein the cyclic portions of each of the above are optionally substituted with 1, 2, or 3 groups that are independently halogen, $C_1$-$C_6$ alkyl, $C_1$-$C_6$ alkoxy, $CF_3$, $OCF_3$, CN, $C_1$-$C_6$ thioalkoxy, or $C_1$-$C_6$ alkoxycarbonyl.

In another aspect, the invention provides compounds of formula III-i3, i.e., compounds according to formula III-b, wherein $R_1$ is benzoimidazolyl($C_1$-$C_6$ alkyl), benzooxazolyl($C_1$-$C_6$ alkyl), benzo[1,2,5]oxadiazolyl($C_1$-$C_6$ alkyl), 1H-indazolyl($C_1$-$C_6$ alkyl), 1H-benzotriazolyl($C_1$-$C_6$ alkyl), furo[3,2-b]pyridinyl($C_1$-$C_6$ alkyl), 1H-pyrazolo[3,4-b]pyridinyl($C_1$-$C_6$ alkyl), 1H-pyrazolo[3,4-c]pyridinyl($C_1$-$C_6$ alkyl), quinoxalinyl($C_1$-$C_6$ alkyl), or isoquinolinyl($C_1$-$C_6$ alkyl), wherein the cyclic portions of each of the above are optionally substituted with 1, 2, 3, 4, or 5 groups that are independently halogen, $C_1$-$C_6$ alkyl, $C_1$-$C_6$ alkoxy, $CF_3$, $OCF_3$, —NR'R", or —C(O)—NR'R", wherein R' is H, $C_1$-$C_6$ alkyl, $C_3$-$C_8$ cycloalkyl, phenyl, phenyl($C_1$-$C_4$)alkyl, $C_1$-$C_6$ alkanoyl, phenyl($C_1$-$C_6$)alkanoyl, pyridyl($C_1$-$C_4$)alkyl, pyrimidyl($C_1$-$C_4$)alkyl, pyridazyl($C_1$-$C_4$)alkyl, pyrazinyl($C_1$-$C_4$)alkyl, thienyl($C_1$-$C_4$) alkyl, oxazolyl($C_1$-$C_4$)alkyl, thiazolyl($C_1$-$C_4$)alkyl, furanyl($C_1$-$C_4$)alkyl, piperidinyl($C_1$-$C_4$)alkyl, —$SO_2$-alkyl, —$SO_2$-phenyl, —$SO_2$-pyridyl, —$SO_2$-pyrimidyl, —$SO_2$-pyridazyl, —$SO_2$-pyrazinyl, —$SO_2$-thienyl, —$SO_2$-oxazolyl, —$SO_2$-thiazolyl, —$SO_2$-furanyl, pyridyl($C_1$-$C_6$)alkanoyl, pyrimidyl($C_1$-$C_6$)alkanoyl, pyridazyl($C_1$-$C_6$)alkanoyl, pyrazinyl($C_1$-$C_6$)alkanoyl, thienyl($C_1$-$C_6$)alkanoyl, oxazolyl($C_1$-$C_6$)alkanoyl, thiazolyl($C_1$-$C_6$)alkanoyl, or furanyl($C_1$-$C_6$)alkanoyl, wherein the alkyl portion of the alkyl and alkanoyl groups are optionally substituted with halogen or $C_1$-$C_6$ alkoxy, wherein the aryl, and heteroaryl groups are optionally substituted with alkyl, alkoxy, halogen, haloalkyl, haloalkoxy, and R" is H, or $C_1$-$C_6$ alkyl, wherein the alkyl group is optionally substituted with halogen.

In another aspect, the invention provides compounds of formula III-i4, i.e., compounds according to formula III-i3, wherein R' is H, $C_1$-$C_6$ alkyl, $C_3$-$C_6$ cycloalkyl, phenyl, phenyl($C_1$-$C_4$)alkyl, $C_1$-$C_4$ alkanoyl, phenyl($C_1$-$C_4$)alkanoyl, pyridyl($C_1$-$C_4$)alkyl, pyrimidyl($C_1$-$C_4$)alkyl, pyridazyl($C_1$-$C_4$)alkyl, pyrazinyl($C_1$-$C_4$)alkyl, thienyl($C_1$-$C_4$)alkyl, oxazolyl($C_1$-$C_4$)alkyl, thiazolyl($C_1$-$C_4$)alkyl, furanyl($C_1$-$C_4$) alkyl, piperidinyl($C_1$-$C_4$)alkyl, —$SO_2$-alkyl, —$SO_2$-phenyl, pyridyl($C_1$-$C_6$)alkanoyl, thienyl($C_1$-$C_4$)alkanoyl, oxazolyl($C_1$-$C_4$)alkanoyl, thiazolyl($C_1$-$C_4$)alkanoyl, or furanyl($C_1$-$C_4$)alkanoyl, wherein the alkyl portion of the alkyl and alkanoyl groups are optionally substituted with halogen or $C_1$-$C_4$ alkoxy, wherein the aryl, and heteroaryl groups are optionally substituted with alkyl, alkoxy, halogen, $CF_3$, $OCF_3$, and R" is H, or $C_1$-$C_4$ alkyl, wherein the alkyl group is optionally substituted with halogen.

In another aspect, the invention provides compounds of formula III-i5, i.e., compounds according to formula III-i4, wherein R' is H, $C_1$-$C_6$ alkyl, cyclopropyl, cyclohexyl, phenyl, benzyl, $C_1$-$C_4$ alkanoyl, phenyl($C_1$-$C_4$)alkanoyl, pyridyl ($C_1$-$C_4$)alkyl, pyrimidyl($C_1$-$C_4$)alkyl, pyrazinyl($C_1$-$C_4$) alkyl, thienyl($C_1$-$C_4$)alkyl, oxazolyl($C_1$-$C_4$)alkyl, thiazolyl ($C_1$-$C_4$)alkyl, furanyl($C_1$-$C_4$)alkyl, piperidinyl($C_1$-$C_4$)alkyl, —$SO_2$-alkyl, —$SO_2$-phenyl, pyridyl($C_1$-$C_4$)alkanoyl, thienyl($C_1$-$C_4$)alkanoyl, wherein the alkyl portion of the alkyl and alkanoyl groups are optionally substituted with halogen or $C_1$-$C_4$ alkoxy, wherein the aryl, and heteroaryl groups are optionally substituted with alkyl, alkoxy, halogen, $CF_3$, $OCF_3$, and R" is H, or $C_1$-$C_4$ alkyl.

In another aspect, the invention provides compounds of formula III-i6, i.e., compounds according to formula III-i5, wherein R' is H, $C_1$-$C_6$ alkyl, cyclopropyl, cyclohexyl, phenyl, or benzyl, wherein the alkyl portion of the alkyl group is optionally substituted with halogen or $C_1$-$C_4$ alkoxy, and wherein the groups are optionally substituted with $C_1$-$C_4$ alkyl, $C_1$-$C_4$ alkoxy, halogen, $CF_3$, or $OCF_3$ and R" is H, or $C_1$-$C_4$ alkyl.

In another aspect, the invention provides compounds of formula III-i7, i.e., compounds according to formula III-i5, wherein R' is $C_1$-$C_4$ alkanoyl, phenyl($C_1$-$C_4$)alkanoyl, pyridyl($C_1$-$C_4$)alkyl, pyrimidyl($C_1$-$C_4$)alkyl, pyrazinyl($C_1$-$C_4$)alkyl, thienyl($C_1$-$C_4$)alkyl, oxazolyl($C_1$-$C_4$)alkyl, thiazolyl($C_1$-$C_4$)alkyl, furanyl($C_1$-$C_4$)alkyl, piperidinyl($C_1$-$C_4$) alkyl, —$SO_2$-alkyl, —$SO_2$-phenyl, pyridyl($C_1$-$C_4$)alkanoyl, thienyl($C_1$-$C_4$)alkanoyl, wherein the alkyl portion of the alkyl and alkanoyl groups are optionally substituted with halogen or $C_1$-$C_4$ alkoxy, wherein the aryl, and heteroaryl groups are optionally substituted with alkyl, alkoxy, halogen, $CF_3$, $OCF_3$, and R" is H, or $C_1$-$C_4$ alkyl.

In another aspect, the invention provides compounds of formula III-i8, i.e., compounds according to formula III-i5, wherein R' is H, $C_1$-$C_4$ alkyl, $C_1$-$C_4$ alkanoyl, phenyl($C_1$-$C_4$) alkanoyl, —$SO_2$-alkyl, —$SO_2$-phenyl, pyridyl($C_1$-$C_4$)alkanoyl, orthienyl($C_1$-$C_4$)alkanoyl, wherein the alkyl portion of the alkyl and alkanoyl groups are optionally substituted with halogen or $C_1$-$C_4$ alkoxy, wherein the aryl, and heteroaryl groups are optionally substituted with alkyl, alkoxy, halogen, $CF_3$, $OCF_3$, and R" is H, or $C_1$-$C_4$ alkyl.

In another aspect, the invention provides compounds of formula III-i9, i.e., compounds according to formula III-i5, wherein R' is H, $C_1$-$C_4$ alkyl, pyridyl($C_1$-$C_4$)alkyl, pyrimidyl ($C_1$-$C_4$)alkyl, pyrazinyl($C_1$-$C_4$)alkyl, thienyl($C_1$-$C_4$)alkyl, oxazolyl($C_1$-$C_4$)alkyl, thiazolyl($C_1$-$C_4$)alkyl, furanyl($C_1$-$C_4$) alkyl, piperidinyl($C_1$-$C_4$)alkyl, —$SO_2$-alkyl, —$SO_2$-phenyl, pyridyl($C_1$-$C_4$)alkanoyl, thienyl($C_1$-$C_4$)alkanoyl, wherein the alkyl portion of the alkyl and alkanoyl groups are optionally substituted with halogen or $C_1$-$C_4$ alkoxy, wherein the aryl, and heteroaryl groups are optionally substituted with alkyl, alkoxy, halogen, $CF_3$, $OCF_3$, and R" is H, or $C_1$-$C_4$ alkyl.

In another aspect, the invention provides compounds of formula III-i10, i.e., compounds according to any one of formulas III-i, III-i1, III-i2, III-i3, III-i4, III-i5, III-i6, III-i7, III-i8, or III-i9, wherein $R_{10}$, $R_{11}$, and $R_{3'}$ are all H. Preferably, at least one of $R_3$ and $R_4$ is halogen. More preferably, n is 2 or 3. Still more preferably, n is 3.

In another aspect, the invention provides compounds of formula III-j, i.e., compounds according to formula I-a wherein
$R_1$ is phenyl($C_2$-$C_6$ alkenyl) or naphthyl($C_2$-$C_6$ alkenyl), wherein the cyclic portion of each is optionally substituted with 1, 2, 3, 4, or 5 groups that are independently $C_1$-$C_6$ alkyl, $C_1$-$C_6$ alkoxy, halogen, $CF_3$, $OCF_3$, thiazolyl, oxazolyl, pyrazolyl, thiazolyl($C_1$-$C_6$)alkoxy, pyridyl ($C_1$-$C_6$)alkoxy, phenyl($C_1$-$C_4$)alkoxy, oxazolyl($C_1$-$C_4$) alkoxy, pyrazolyl($C_1$-$C_4$)alkoxy, phenyloxy, $C_1$-$C_6$ alkoxycarbonyl, —O—$CH_2CH_2$—O—, —O—$CH_2$—O—, —NHR', —NR'R", morpholinyl, thiomorpholinyl, thiomorpholinyl S,S-dioxide, piperidinyl, pyrrolidinyl, phenyl, CN, —$SO_2$-phenyl, —($C_1$-$C_4$ alkyl)-$SO_2$-phenyl, OH, $C_1$-$C_6$ thioalkoxy, $C_2$-$C_6$ alkenyl, or —O—$SO_2$-phenyl, wherein
the heteroaryl group is optionally substituted with 1, 2, or 3 groups that are independently $C_1$-$C_6$ alkyl, $C_1$-$C_6$ alkoxy, or halogen,
the heterocycloalkyl group is optionally substituted with $C_1$-$C_6$ alkyl, $C_1$-$C_6$ alkoxy, or halogen,
the above phenyl groups are optionally substituted with 1, 2, 3, 4 or 5 groups that are independently halogen, $C_1$-$C_6$ alkyl, or $C_1$-$C_4$ alkoxy,
R' is H, $C_1$-$C_6$ alkyl, or $C_1$-$C_6$ alkanoyl, wherein the alkyl portion of the alkyl and alkanoyl groups are optionally substituted with halogen, or $C_1$-$C_6$ alkoxy,
R" is H or $C_1$-$C_6$ alkyl, wherein the alkyl group is optionally substituted with halogen.

In another aspect, the invention provides compounds of formula III-k, i.e., compounds according to formula I-j wherein
$R_3$ is H, halogen, $C_1$-$C_4$ alkyl, $C_1$-$C_4$ alkoxy, $CF_3$, or CN;
$R_4$ is halogen, $C_1$-$C_4$ alkoxy, $C_1$-$C_4$ alkyl, $CF_3$, $OCF_3$, CN, —NHR', —NR'R", or $C_1$-$C_4$ alkanoyl,
$R_{3'}$ is H. —$SO_2$—NR'R", or halogen; or
$R_4$ and $R_{3'}$ and the carbons to which they are attached form a benzo ring.

In another aspect, the invention provides compounds of formula III-l, i.e., compounds according to formula III-k wherein
$R_1$ is phenyl($C_2$-$C_6$ alkenyl) wherein the cyclic portion is optionally substituted with 1, 2, 3, 4, or 5 groups that are independently
$C_1$-$C_6$ alkyl, $C_1$-$C_6$ alkoxy, halogen, $CF_3$, $OCF_3$, thiazolyl, oxazolyl, pyrazolyl, thiazolyl($C_1$-$C_4$)alkoxy, pyridyl ($C_1$-$C_4$)alkoxy, phenyl($C_1$-$C_4$)alkoxy, oxazolyl($C_1$-$C_4$) alkoxy, pyrazolyl($C_1$-$C_4$)alkoxy, phenyloxy, $C_1$-$C_4$ alkoxycarbonyl, —O—$CH_2CH_2$—O—, —O—$CH_2$—O—, morpholinyl, $NH_2$, NH($C_1$-$C_4$)alkyl, N($C_1$-$C_4$) alkyl($C_1$-$C_4$)alkyl, piperidinyl, pyrrolidinyl, phenyl, CN, OH, $C_1$-$C_4$ thioalkoxy, $C_2$-$C_6$ alkenyl,
wherein
the heteroaryl group is optionally substituted with 1, 2, or 3 groups that are independently $C_1$-$C_6$ alkyl, $C_1$-$C_6$ alkoxy, or halogen,
the heterocycloalkyl group is optionally substituted with $C_1$-$C_6$ alkyl, $C_1$-$C_6$ alkoxy, or halogen,
the above phenyl groups are optionally substituted with 1, 2, 3, 4 or 5 groups that are independently halogen, $C_1$-$C_6$ alkyl, or $C_1$-$C_4$ alkoxy.

In another aspect, the invention provides compounds of formula III-m, i.e., compounds according to formula III-l wherein
$R_2$ is H, methyl, or benzyl;
$R_{10}$ and $R_{11}$ are simultaneously H; and
$R_1$ is phenyl($C_3$-$C_6$ alkenyl) wherein the cyclic portion is optionally substituted with 1, 2, 3, 4, or 5 groups that are independently $C_1$-$C_6$ alkyl, $C_1$-$C_6$ alkoxy, halogen, $CF_3$, $OCF_3$, phenyl($C_1$-$C_4$)alkoxy, phenyloxy, $C_1$-$C_4$ alkoxycarbonyl, —O—$CH_2CH_2$—O—, —O—$CH_2$—O—, $NH_2$, NH($C_1$-$C_4$)alkyl, N($C_1$-$C_4$)alkyl($C_1$-$C_4$)alkyl, phenyl, CN, OH, $C_1$-$C_4$ thioalkoxy, $C_2$-$C_6$ alkenyl, wherein the above phenyl groups are optionally substituted with 1, 2, or 3 groups that are independently halogen, $C_1$-$C_4$ alkyl, or $C_1$-$C_4$ alkoxy.

In another aspect, the invention provides compounds of formula III-n, i.e., compounds according to formula III-m wherein
$R_2$ is H; $R_3$ is H, halogen, methyl, ethyl, methoxy, ethoxy, $CF_3$, or CN;
$R_4$ is halogen, $C_1$-$C_4$ alkoxy, $C_1$-$C_4$ alkyl, $CF_3$, $OCF_3$, CN, —NHR', —NR'R", or $C_1$-$C_4$ alkanoyl,
$R_{3'}$ is H, or halogen; or
$R_4$ and $R_{3'}$ and the carbons to which they are attached form a benzo ring.

In another aspect, the invention provides compounds of formula III-o, i.e., compounds according to formula III-n wherein $R_4$ is halogen; and $R_3$ is H, halogen, methyl or methoxy. In another aspect, $R_4$ is Cl. In another aspect, $R_3$ is H or halogen. In still another aspect, $R_4$ is Cl, and $R_3$ is H or halogen.

In another aspect, the invention provides compounds of formula III-p, i.e., compounds according to formula III-n wherein $R_4$ and $R_{3'}$ and the carbons to which they are attached form a benzo ring.

In another aspect, the invention provides compounds of formula III-q, i.e., compounds according to any one of formulas III-j, III-k, III-l, III-m, III-n, III-o, or III-p
wherein
n is 1. In another aspect, n is 2. In still another aspect, n is 3.

In yet another aspect, the invention provides compounds of formula I-b, i.e., compounds of formula I wherein
$R_2$ is H, methyl, or benzyl;
$R_{10}$ and $R_{11}$ are simultaneously H;
$R_3$ is H, halogen, $C_1$-$C_4$ alkyl, $C_1$-$C_4$ alkoxy, $CF_3$, or CN,
$R_4$ is halogen, $C_1$-$C_4$ alkoxy, $C_1$-$C_4$ alkyl, $CF_3$, $OCF_3$, CN, —NHR', —NR'R", or $C_1$-$C_4$ alkanoyl,
$R_{3'}$ is H, —$SO_2$—NR'R", or halogen; or
$R_4$ and $R_{3'}$ and the carbons to which they are attached form a benzo ring.

In another aspect, the invention provides compounds of formula I-c, i.e., compounds of formula I-b wherein
$R_1$ is $C_1$-$C_{14}$ alkyl, $C_2$-$C_{16}$ alkenyl, or $C_2$-$C_6$ alkynyl, each of which is optionally substituted with 1 or 2 groups that are independently OH, halogen, $C_1$-$C_6$ alkoxy, phenyl, naphthyl, phenyl($C_1$-$C_4$)alkoxy, phenyloxy, phenyl($C_1$-$C_4$)alkyl, pyridyl, thienyl, —$CO_2$—($C_1$-$C_6$ alkyl), —NR'R", $C_1$-$C_6$ thioalkoxy, OH, —N($R_{16}$)C(O)—$R_{17}$, —C(O)NR$_{30}$R$_{31}$, —NH—S(O)$_x$—$R_{25}$, —N($C_1$-$C_6$ alkyl)-S(O)$_x$—$R_{25}$, CN, or —S(O)$_x$—$R_{25}$,
wherein the above phenyl and naphthyl groups are optionally substituted with 1, 2, or 3 groups that are independently OH, $C_1$-$C_6$ alkoxy, $C_1$-$C_6$ alkyl, or halogen;
x is 0, 1, or 2;
$R_{16}$ is H or $C_1$-$C_6$ alkyl;
$R_{17}$ is $C_1$-$C_6$ alkyl, phenyl, pyridyl, pyrimidyl, pyridazyl, pyrazinyl, thienyl, oxazolyl, thiazolyl, furanyl, $C_1$-$C_6$ alkoxy, OH, phenyloxy, pyridyloxy, pyrimidyloxy, pyridazyloxy, pyrazinyloxy, thienyloxy, oxazolyloxy, thiazolyloxy, furanyloxy, phenyl($C_1$-$C_6$)alkoxy, or —$NR_{18}R_{19}$;
$R_{18}$ and $R_{19}$ are independently H, $C_1$-$C_6$ alkyl, phenyl, pyridyl, piperidinyl, pyrrolidinyl, morpholinyl, thiomorpholinyl, thiomorpholinyl 1,1-dioxide, tetrahydrothiopyranyl 1,1-dioxide, or phenyl($C_1$-$C_4$) alkyl;
$R_{25}$ is $C_1$-$C_6$ alkyl, OH, $NR_{26}R_{27}$;

$R_{26}$ and $R_{27}$ are independently H, $C_1$-$C_6$ alkyl, phenyl($C_1$-$C_4$ alkyl), phenyl, naphthyl or pyridyl, pyrimidyl, thienyl, furanyl or quinolinyl; or
$R_{26}$, $R_{27}$ and the nitrogen to which they are attached form a heterocycloalkyl ring, which contains 2 to 7 carbon atoms, and
$R_{30}$ and $R_{31}$ are independently H, $C_1$-$C_6$ alkyl, phenyl, benzyl, pyridyl, thiazolyl, oxazolyl, or indolyl, or
$R_{30}$, $R_{31}$, and the nitrogen to which they are attached form a azepanyl, piperidinyl, pyrrolidinyl, morpholinyl, thiomorpholinyl, or thiomorpholinyl 1,1-dioxide.

In another aspect, the invention provides compounds of formula I-d, i.e., compounds of formula I-c wherein $R_4$ is halogen; and $R_3$ is H, halogen, methyl or methoxy. In another aspect, $R_4$ is Cl. In another aspect, $R_3$ is H or halogen. In still another aspect, $R_4$ is Cl, and $R_3$ is H or halogen.

In another aspect, the invention provides compounds of formula I-e, i.e., compounds of formula I-c wherein $R_4$ and $R_{3'}$ and the carbons to which they are attached form a benzo ring. In another aspect, $R_4$ and $R_{3'}$ and the carbons to which they are attached form a benzo ring and $R_3$ is H, halogen, methyl or methoxy.

In yet another aspect, the invention provides compounds of formula I-f, i.e., compounds according to any one of formulas I-c, I-d, or I-e wherein
$R_1$ is $C_1$-$C_{14}$ alkyl (in another aspect, $C_1$-$C_{10}$ alkyl, in still another aspect, $C_1$-$C_8$ alkyl, in yet still another aspect, $C_1$-$C_6$ alkyl), which is optionally substituted with 1 or 2 groups that are independently OH, halogen, $C_1$-$C_6$ alkoxy, phenyl, naphthyl, phenyl($C_1$-$C_4$)alkoxy, phenyloxy, —$CO_2$—($C_1$-$C_4$ alkyl), —NR'R", $C_1$-$C_4$ thioalkoxy, OH, —C(O)NR$_{30}$R$_{31}$, —N($R_{16}$)C(O)—$R_{17}$, —NH—S(O)$_x$—$R_{25}$, —N($C_1$-$C_6$ alkyl)-S(O)$_x$—$R_{25}$, CN, or —S(O)$_x$—$R_{25}$;
wherein the above phenyl and naphthyl groups are optionally substituted with 1, 2, or 3 groups that are independently OH, $C_1$-$C_4$ alkoxy, $C_1$-$C_4$ alkyl, or halogen
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl($C_1$-$C_4$ alkyl), phenyl, naphthyl pyridyl, pyrimidyl, thienyl, furanyl or quinolinyl; or
$R_{26}$, $R_{27}$ and the nitrogen to which they are attached form a heterocycloalkyl ring selected from piperidinyl, morpholinyl, pyrrolidinyl, and piperazinyl.

In yet another aspect, the invention provides compounds of formula I-g, i.e., compounds according to any one of formulas I-d, I-e, or I-f wherein
$R_1$ is

wherein
m is 0, 1, 2, 3, 4, 5, or 6;
$R_{20}$ is H or methyl;
Y is halogen, $C_1$-$C_4$ alkoxy, benzyloxy, phenyloxy, —$CO_2$—($C_1$-$C_4$ alkyl), —NR'R", $C_1$-$C_4$ thioalkoxy, OH, —C(O)NR$_{30}$R$_{31}$, —N($R_{16}$)C(O)—$R_{17}$, or —S(O)$_x$—$R_{25}$;
wherein the above phenyl groups are optionally substituted with 1, 2, or 3 groups that are independently OH, $C_1$-$C_4$ alkoxy, $C_1$-$C_4$ alkyl, or halogen;
x is 0, 1, or 2;

$R_{25}$ is $C_1$-$C_6$ alkyl, OH, $NR_{26}R_{27}$;

$R_{26}$ and $R_{27}$ are independently H, $C_1$-$C_6$ alkyl, phenyl($C_1$-$C_4$ alkyl), phenyl, naphthyl, pyridyl, pyrimidyl, thienyl, or furanyl; or $R_{26}$, $R_{27}$ and the nitrogen to which they are attached form a heterocycloalkyl ring selected from piperidinyl, morpholinyl, pyrrolidinyl, and piperazinyl.

In still another aspect, the invention provides compounds of formula I-G1, i.e., compounds of formula I-G wherein Y is $-CO_2-(C_1$-$C_4$ alkyl).

In another aspect, the invention provides compounds of formula I-h, i.e., compounds according formula I-g wherein $R_{26}$ and $R_{27}$ are independently H, $C_1$-$C_6$ alkyl, phenyl($C_1$-$C_4$ alkyl), phenyl, naphthyl, pyridyl, pyrimidyl, thienyl, or furanyl.

In another aspect, the invention provides compounds of formula I-i, i.e., compounds according formula I-g, wherein $R_{26}$, $R_{27}$ and the nitrogen to which they are attached form a heterocycloalkyl ring selected from piperidinyl, morpholinyl, pyrrolidinyl, and piperazinyl.

In another aspect, the invention provides compounds of formula I-j, i.e., compounds according formula I-g wherein $R_{30}$ and $R_{31}$ are independently H, $C_1$-$C_6$ alkyl, phenyl, benzyl, pyridyl, thiazolyl, oxazolyl, or indolyl.

In another aspect, the invention provides compounds of formula I-k, i.e., compounds according formula I-g wherein $R_{30}$, $R_{31}$, and the nitrogen to which they are attached form a azepanyl, piperidinyl, pyrrolidinyl, morpholinyl, thiomorpholinyl, or thiomorpholinyl 1,1-dioxide.

In another aspect, the invention provides compounds of formula I-l, i.e., compounds according to any one of formulas I-c, I-d, I-e wherein $R_1$ is $C_2$-$C_{16}$ alkenyl which is optionally substituted with 1 or 2 groups that are independently OH, halogen, $C_1$-$C_6$ alkoxy, phenyl($C_1$-$C_4$)alkoxy, phenyloxy, phenyl($C_1$-$C_4$) alkyl, pyridyl, pyrimidyl, furanyl, thienyl, indolyl, $-CO_2-(C_1$-$C_4$ alkyl), $-NR'R''$, $C_1$-$C_4$ thioalkoxy, or OH, wherein the above phenyl and naphthyl groups are optionally substituted with 1, 2, or 3 groups that are independently OH, $C_1$-$C_4$ alkoxy, $C_1$-$C_4$ alkyl, or halogen.

In another aspect, the invention provides compounds of formula I-m, i.e., compounds of formula I-l wherein $R_1$ is

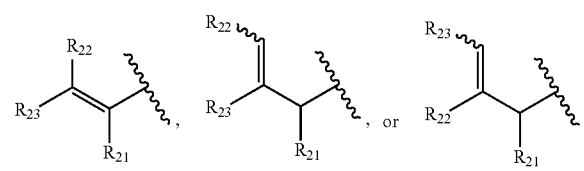

wherein $R_{21}$ and $R_{22}$ are independently H or $C_1$-$C_6$ alkyl;

$R_{23}$ is H, $-C(O)NR_{30}R_{31}$, $-CO_2-(C_1$-$C_4$ alkyl), $C_1$-$C_6$ alkyl, phenyl, naphthyl, benzyl, pyridyl, pyrimidyl, furanyl, or thienyl;

$R_{30}$ and $R_{31}$ are independently H, $C_1$-$C_6$ alkyl, phenyl, benzyl, pyridyl, thiazolyl, oxazolyl, or indolyl, or $R_{30}$, $R_{31}$, and the nitrogen to which they are attached form a azepanyl, piperidinyl, pyrrolidinyl, morpholinyl, thiomorpholinyl, or thiomorpholinyl 1,1-dioxide.

In another aspect, the invention provides compounds of formula I-n, i.e., compounds of formula I-m wherein $R_1$ is

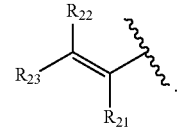

In another aspect, the invention provides compounds of formula I-o, i.e., compounds of formula I-m wherein $R_1$ is

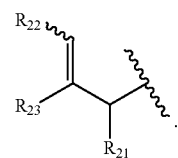

In another aspect, the invention provides compounds of formula I-p, i.e., compounds of formula I-m wherein $R_1$ is

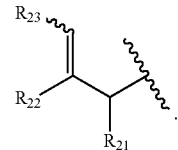

In still another aspect, the invention provides compounds of formula I-q, i.e., compounds according to any one of formulas I-m, I-n, I-o, or I-p wherein $R_{23}$ is $-C(O)NR_{30}R_{31}$.

In yet another aspect, the invention provides compounds of formula I-q1, i.e., compounds of formula I-p wherein $R_{23}$ is $-CO_2-(C_1$-$C_4$ alkyl).

In still another aspect, the invention provides compounds of formula I-r, i.e., compounds according to any one of formulas I-c, I-d, or I-e wherein $R_1$ is $C_2$-$C_6$ alkynyl, which is optionally substituted with 1 or 2 groups that are independently halogen, $C_1$-$C_6$ alkoxy, phenyl, naphthyl, phenyl($C_1$-$C_4$)alkoxy, phenyloxy, $-CO_2-(C_1$-$C_4$ alkyl), $-NR'R''$, $C_1$-$C_4$ thioalkoxy, or OH, wherein the above phenyl and naphthyl groups are optionally substituted with 1, 2, or 3 groups that are independently OH, $C_1$-$C_4$ alkoxy, $C_1$-$C_4$ alkyl, or halogen.

In another aspect, the invention provides compounds of formula I-s, i.e., compounds of formula I-r wherein $R_1$ is

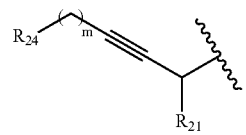

wherein m is 0, 1, or 2;

$R_{21}$ is H or methyl;

$R_{24}$ is H, halogen, $C_1$-$C_6$ alkoxy, phenyl, naphthyl, phenyl($C_1$-$C_4$)alkoxy, phenyloxy, $-CO_2-(C_1$-$C_4$ alkyl), —NR'R", $C_1$-$C_4$ thioalkoxy, or OH, wherein the above phenyl and naphthyl groups are optionally substituted with 1, 2, or 3 groups that are independently OH, $C_1$-$C_4$ alkoxy, $C_1$-$C_4$ alkyl, or halogen.

In another aspect, the invention provides compounds of formula I-t, i.e., compounds of formula I-m wherein $R_1$ is

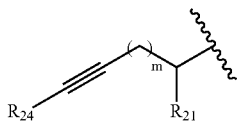

wherein
m is 0, 1, or 2;
$R_{21}$ is H or methyl;
$R_{24}$ is H, halogen, $C_1$-$C_6$ alkoxy, phenyl, naphthyl, phenyl($C_1$-$C_4$)alkoxy, phenyloxy, —$CO_2$—($C_1$-$C_4$ alkyl), —NR'R", $C_1$-$C_4$ thioalkoxy, or OH, wherein the above phenyl and naphthyl groups are optionally substituted with 1, 2, or 3 groups that are independently OH, $C_1$-$C_4$ alkoxy, $C_1$-$C_4$ alkyl, or halogen.

In another aspect, the invention provides compounds of formula I-u, i.e., compounds according to any one of formulas I-b, I-c, I-d, I-e, I-f, I-g, I-h, I-I, I-j, I-j, I-k, I-l, I-m, I-n, I-o, I-p, I-q, or I-r wherein n is 1. In another aspect, n is 2. In still another aspect, n is 3.

In another aspect, the invention provides compounds of formula I-v, i.e., compounds of formula I-b wherein
$R_1$ is $C_3$-$C_7$ cycloalkyl($C_1$-$C_4$ alkyl) wherein the cyclic portion is optionally substituted with 1, 2, 3, 4, or 5 groups that are independently halogen, $C_1$-$C_6$ alkyl, OH, $C_1$-$C_6$ alkoxycarbonyl, $CO_2H$, or $C_1$-$C_6$ alkoxy.

In another aspect, the invention provides compounds of formula I-w, i.e., compounds of formula I-v wherein $R_4$ is halogen; and $R_3$ is H. halogen, methyl or methoxy. In another aspect, $R_4$ is Cl. In another aspect, $R_3$ is H or halogen. In still another aspect, $R_4$ is Cl, and $R_3$ is H or halogen.

In another aspect, the invention provides compounds of formula I-x, i.e., compounds of formula I-v wherein $R_4$ and $R_3$, and the carbons to which they are attached form a benzo ring. In another aspect, $R_4$ and $R_3$, and the carbons to which they are attached form a benzo ring and $R_3$ is H, halogen, methyl or methoxy.

In another aspect, the invention provides compounds of formula I-y, i.e., compounds according to any one of formulas I-w or I-x wherein
$R_1$ is cyclopropyl($C_1$-$C_4$ alkyl), cyclopentyl($C_1$-$C_4$ alkyl), or cyclohexyl($C_1$-$C_4$ alkyl), wherein the cyclic portion is optionally substituted with 1, 2, or 3 groups that are independently halogen, $C_1$-$C_4$ alkyl, OH, $C_1$-$C_4$ alkoxycarbonyl, or $C_1$-$C_4$ alkoxy.

In another aspect, the invention provides compounds of formula I-z, i.e., compounds according to any one of formulas I-v, I-w, or I-x,
$R_1$ is of the formula:

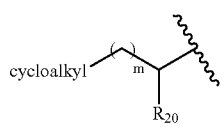

wherein
m is 0, 1, 2, or 3;
$R_{20}$ is H or methyl; and
cycloalkyl is $C_3$-$C_7$ cycloalkyl wherein the cyclic portion is optionally substituted with 1, 2, 3, 4, or 5 groups that are independently halogen, $C_1$-$C_6$ alkyl, OH, $C_1$-$C_4$ alkoxycarbonyl, or $C_1$-$C_6$ alkoxy.

In another aspect, the invention provides compounds of formula I-aa, i.e., compounds formula I-z wherein
cycloalkyl is cyclopropyl, cyclopentyl, or cyclohexyl, wherein the cyclic portion is optionally substituted with 1, 2, or 3 groups that are independently halogen, $C_1$-$C_4$ alkyl, OH, $C_1$-$C_4$ alkoxycarbonyl, or $C_1$-$C_4$ alkoxy.

In another aspect, the invention provides compounds of formula I-bb, i.e., compounds according to any one of formulas I-v, I-w, I-x, I-y, I-z, or I-aa wherein n is 1. In another aspect, n is 2. In still another aspect, n is 3.

In yet another aspect, the invention provides compounds of formula I-bb1, i.e., compounds of formula I-bb wherein cycloalkyl is cyclopropyl, which is optionally substituted as described above.

In yet another aspect, the invention provides compounds of formula I-bb2, i.e., compounds of formula I-bb wherein cycloalkyl is cyclopentyl, which is optionally substituted as described above.

In yet another aspect, the invention provides compounds of formula I-bb3, i.e., compounds of formula I-bb wherein cycloalkyl is cyclohexyl, which is optionally substituted as described above.

In another aspect, the invention provides compounds of formula I-cc, i.e., compounds of any one of formulas I-bb, I-bb1, I-bb2, or I-bb3, wherein m is 0 or 1.

In another aspect, the invention provides compounds of formula I-cc1, i.e., compounds of any one of formulas I-bb, I-bb1, I-bb2, or I-bb3, wherein m is 1 or 2.

In another aspect, the invention provides compounds of formula I-dd, i.e., compounds of formula I-b wherein
$R_1$ is 4-oxo-4H-chromen-3-yl($C_1$-$C_4$ alkyl), 2H-chromen-3-yl($C_1$-$C_4$ alkyl), pyrrolidinonyl dione($C_1$-$C_4$ alkyl), isoindol-2-yl dione($C_1$-$C_4$ alkyl), 1,3-dioxolan-2-yl($C_1$-$C_4$ alkyl), dioxanyl($C_1$-$C_4$ alkyl), or tetrahydropyran-2-yl($C_1$-$C_4$ alkyl), wherein the cyclic portion of each is optionally substituted with 1, 2, 3, 4, or 5 groups that are independently $C_1$-$C_4$ alkyl, $C_1$-$C_4$ alkoxy, or halogen; and
$R_2$ is H.

In another aspect, the invention provides compounds of formula I-ee, i.e., compounds of formula I-dd wherein $R_4$ is halogen; and $R_3$ is H, halogen, methyl or methoxy. In another aspect, $R_4$ is Cl. In another aspect, $R_3$ is H or halogen. In still another aspect, $R_4$ is Cl, and $R_3$ is H or halogen.

In another aspect, the invention provides compounds of formula I-ff, i.e., compounds of formula I-dd wherein $R_4$ and $R_3$, and the carbons to which they are attached form a benzo ring. In another aspect, $R_4$ and $R_3$, and the carbons to which they are attached form a benzo ring and $R_3$ is H, halogen, methyl or methoxy.

In another aspect, the invention provides compounds of formula I-gg, i.e., compounds according to any one of formulas I-b, I-c, I-d, I-e, I-f, I-g, I-h, I-i, I-j, I-k, or I-l wherein n is 1. In another aspect, n is 2. In still another aspect, n is 3.

In another aspect, the invention provides compounds of formula I-hh, i.e., compounds of formula I-f wherein $R_1$ is of the formula:

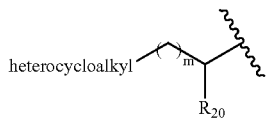

wherein
m is 0, 1, 2, or 3;
$R_{20}$ is H or methyl; and
heterocycloalkyl is 4-oxo-4H-chromen-3-yl, 2H-chromen-3-yl, pyrrolidinonyl dione, isoindol-2-yl dione, 1,3-dioxolan-2-yl, dioxanyl, or tetrahydropyran-2-yl, wherein the cyclic portion of each is optionally substituted with 1, 2, 3, 4, or 5 groups that are independently $C_1$-$C_4$ alkyl, $C_1$-$C_4$ alkoxy, or halogen.

In another aspect, the invention provides compounds of formula I-ii, i.e., compounds of formula I-g wherein m is 0 or 1. In another aspect, m is 0 or 1 and heterocycloalkyl is isoindol-2-yl dione.

In another aspect, the invention provides compounds of formula I-ii1, i.e., compounds of formula I-g wherein m is 1 or 2. In another aspect, m is 1 or 2 and heterocycloalkyl is isoindol-2-yl dione.

In another aspect, the invention provides compounds of formula I-ii2, i.e., compounds of formula I-b, wherein $R_1$ is 3-oxo-1,3-dihydro-benzo[c]isoxazolyl($C_1$-$C_4$ alkyl), 2-oxo-2,3-dihydro-1H-benzoimidazolyl($C_1$-$C_4$ alkyl), 3-oxo-3,4-dihydro-1H-2-oxa-3lambda4-thia-1,4-diaza-naphthyl($C_1$-$C_4$ alkyl), 3,3-dimethyl-3H-indazolyl($C_1$-$C_4$ alkyl), or piperidinyl($C_1$-$C_4$ alkyl), wherein the cyclic portion of each is optionally substituted with 1, 2, or 3 groups that are independently halogen, $C_1$-$C_4$ alkyl, $C_1$-$C_4$ alkoxy, $CF_3$, $OCF_3$, phenyl, phenyl($C_1$-$C_4$ alkyl), phenyloxy, pyrazolyl, imidazolyl, furanyl, thienyl, morpholinyl, —$SO_2$-phenyl, —$SO_2$—($C_1$-$C_6$ alkyl), —$S(O)_x$—$R_{25}$, —($C_1$-$C_4$ alkyl)-$S(O)_x$—$R_{25}$, CN, $C_1$-$C_4$ thioalkoxy, $C_1$-$C_4$ alkoxycarbonyl, —NR'R", —C(O)—NR'R", pyridyl, piperidinyl, piperazinyl, pyrrolidinyl, or tetrahydrofuranyl, wherein the above phenyl groups are optionally substituted with 1, 2, 3, or 4 groups that are independently halogen, $C_1$-$C_6$ alkyl, $C_1$-$C_6$ alkoxy, $C_1$-$C_4$ haloalkyl, $C_1$-$C_4$ haloalkoxy, or CN; wherein the above heteroaryl and heterocycloalkyl groups are optionally substituted with 1, 2, or 3 groups that are independently halogen, $CF_3$, ($C_1$-$C_4$)alkyl, $C_1$-$C_6$ thioalkoxy, or $C_1$-$C_4$ alkoxy.

In another aspect, the invention provides compounds of formula I-ii3, i.e., compounds of formula I-ii2, wherein $R_1$ is $R_1$ is 3-oxo-1,3-dihydro-benzo[c]isoxazolyl($C_1$-$C_2$ alkyl), 2-oxo-2,3-dihydro-1H-benzoimidazolyl($C_1$-$C_2$ alkyl), 3-oxo-3,4-dihydro-1H-2-oxa-3lambda4-thia-1,4-diaza-naphthyl($C_1$-$C_2$ alkyl), or 3,3-dimethyl-3H-indazolyl($C_1$-$C_2$ alkyl).

In another aspect, the invention provides compounds of formula I-ii4, i.e., compounds of formula I-ii3, wherein R' is H, $C_1$-$C_6$ alkyl, $C_3$-$C_8$ cycloalkyl, phenyl, phenyl($C_1$-$C_4$) alkyl, $C_1$-$C_6$ alkanoyl, phenyl($C_1$-$C_6$)alkanoyl, pyridyl($C_1$-$C_4$)alkyl, pyrimidyl($C_1$-$C_4$)alkyl, pyridazyl($C_1$-$C_4$)alkyl, pyrazinyl($C_1$-$C_4$)alkyl, thienyl($C_1$-$C_4$)alkyl, oxazolyl($C_1$-$C_4$)alkyl, thiazolyl($C_1$-$C_4$)alkyl, furanyl($C_1$-$C_4$)alkyl, piperidinyl($C_1$-$C_4$)alkyl, —$SO_2$-alkyl, —$SO_2$-phenyl, —$SO_2$-pyridyl, —$SO_2$-pyrimidyl, —$SO_2$-pyridazyl, —$SO_2$-pyrazinyl, —$SO_2$-thienyl, —$SO_2$-oxazolyl, —$SO_2$-thiazolyl, —$SO_2$-furanyl, pyridyl($C_1$-$C_6$)alkanoyl, pyrimidyl($C_1$-$C_6$) alkanoyl, pyridazyl($C_1$-$C_6$)alkanoyl, pyrazinyl($C_1$-$C_6$)alkanoyl, thienyl($C_1$-$C_6$)alkanoyl, oxazolyl($C_1$-$C_6$)alkanoyl, thiazolyl($C_1$-$C_6$)alkanoyl, or furanyl($C_1$-$C_6$)alkanoyl, wherein the alkyl portion of the alkyl and alkanoyl groups are optionally substituted with halogen or $C_1$-$C_6$ alkoxy, wherein the aryl, and heteroaryl groups are optionally substituted with alkyl, alkoxy, halogen, haloalkyl, haloalkoxy, and R" is H, or $C_1$-$C_6$ alkyl, wherein the alkyl group is optionally substituted with halogen.

In another aspect, the invention provides compounds of formula I-ii5, i.e., compounds of formula I-ii4, wherein R' is H, $C_1$-$C_6$ alkyl, $C_3$-$C_6$ cycloalkyl, phenyl, phenyl($C_1$-$C_4$) alkyl, $C_1$-$C_4$ alkanoyl, phenyl($C_1$-$C_4$)alkanoyl, pyridyl($C_1$-$C_4$)alkyl, pyrimidyl($C_1$-$C_4$)alkyl, pyridazyl($C_1$-$C_4$)alkyl, pyrazinyl($C_1$-$C_4$)alkyl, thienyl($C_1$-$C_4$)alkyl, oxazolyl($C_1$-$C_4$)alkyl, thiazolyl($C_1$-$C_4$)alkyl, furanyl($C_1$-$C_4$)alkyl, piperidinyl($C_1$-$C_4$)alkyl, —$SO_2$-alkyl, —$SO_2$-phenyl, pyridyl($C_1$-$C_6$)alkanoyl, thienyl($C_1$-$C_4$)alkanoyl, oxazolyl($C_1$-$C_4$) alkanoyl, thiazolyl($C_1$-$C_4$)alkanoyl, or furanyl($C_1$-$C_4$) alkanoyl, wherein the alkyl portion of the alkyl and alkanoyl groups are optionally substituted with halogen or $C_1$-$C_4$ alkoxy, wherein the aryl, and heteroaryl groups are optionally substituted with alkyl, alkoxy, halogen, $CF_3$, $OCF_3$, and R" is H, or $C_1$-$C_4$ alkyl, wherein the alkyl group is optionally substituted with halogen.

In another aspect, the invention provides compounds of formula I-ii5, i.e., compounds of formula I-ii4, wherein R' is H, $C_1$-$C_6$ alkyl, cyclopropyl, cyclohexyl, phenyl, benzyl, $C_1$-$C_4$ alkanoyl, phenyl($C_1$-$C_4$)alkanoyl, pyridyl($C_1$-$C_4$) alkyl, pyrimidyl($C_1$-$C_4$)alkyl, pyrazinyl($C_1$-$C_4$)alkyl, thienyl($C_1$-$C_4$)alkyl, oxazolyl($C_1$-$C_4$)alkyl, thiazolyl($C_1$-$C_4$)alkyl, furanyl($C_1$-$C_4$)alkyl, piperidinyl($C_1$-$C_4$)alkyl, —$SO_2$-alkyl, —$SO_2$-phenyl, pyridyl($C_1$-$C_4$)alkanoyl, thienyl($C_1$-$C_4$)alkanoyl, wherein the alkyl portion of the alkyl and alkanoyl groups are optionally substituted with halogen or $C_1$-$C_4$ alkoxy, wherein the aryl, and heteroaryl groups are optionally substituted with alkyl, alkoxy, halogen, $CF_3$, $OCF_3$, and R" is H, or $C_1$-$C_4$ alkyl.

In another aspect, the invention provides compounds of formula I-ii6, i.e., compounds of formula I-ii5, wherein R' is R' is H, $C_1$-$C_6$ alkyl, cyclopropyl, cyclohexyl, phenyl, or benzyl, wherein the alkyl portion of the alkyl group is optionally substituted with halogen or $C_1$-$C_4$ alkoxy, and wherein the groups are optionally substituted with $C_1$-$C_4$ alkyl, $C_1$-$C_4$ alkoxy, halogen, $CF_3$, or $OCF_3$ and R" is H, or $C_1$-$C_4$ alkyl.

In another aspect, the invention provides compounds of formula I-ii7, i.e., compounds of formula I-ii5, wherein R' is $C_1$-$C_4$ alkanoyl, phenyl($C_1$-$C_4$)alkanoyl, pyridyl($C_1$-$C_4$) alkyl, pyrimidyl($C_1$-$C_4$)alkyl, pyrazinyl($C_1$-$C_4$)alkyl, thienyl($C_1$-$C_4$)alkyl, oxazolyl($C_1$-$C_4$)alkyl, thiazolyl($C_1$-$C_4$)alkyl, furanyl($C_1$-$C_4$)alkyl, piperidinyl($C_1$-$C_4$)alkyl, —$SO_2$-alkyl, —$SO_2$-phenyl, pyridyl($C_1$-$C_4$)alkanoyl, thienyl($C_1$-$C_4$)alkanoyl, wherein the alkyl portion of the alkyl and alkanoyl groups are optionally substituted with halogen or $C_1$-$C_4$ alkoxy, wherein the aryl, and heteroaryl groups are optionally substituted with alkyl, alkoxy, halogen, $CF_3$, $OCF_3$, and R" is H, or $C_1$-$C_4$ alkyl.

In another aspect, the invention provides compounds of formula I-ii8, i.e., compounds of formula I-ii5, wherein R' is H, $C_1$-$C_4$ alkyl, $C_1$-$C_4$ alkanoyl, phenyl($C_1$-$C_4$)alkanoyl, —$SO_2$-alkyl, —$SO_2$-phenyl, pyridyl($C_1$-$C_4$)alkanoyl, or thienyl($C_1$-$C_4$)alkanoyl, wherein the alkyl portion of the alkyl and alkanoyl groups are optionally substituted with halogen or $C_1$-$C_4$ alkoxy, wherein the aryl, and heteroaryl groups are optionally substituted with alkyl, alkoxy, halogen, $CF_3$, $OCF_3$, and R" is H, or $C_1$-$C_4$ alkyl.

In another aspect, the invention provides compounds of formula I-ii9, i.e., compounds of formula I-ii5, wherein R' is R' is H, $C_1$-$C_4$ alkyl, pyridyl($C_1$-$C_4$)alkyl, pyrimidyl($C_1$-$C_4$) alkyl, pyrazinyl($C_1$-$C_4$)alkyl, thienyl($C_1$-$C_4$)alkyl, oxazolyl ($C_1$-$C_4$)alkyl, thiazolyl($C_1$-$C_4$)alkyl, furanyl($C_1$-$C_4$)alkyl, piperidinyl($C_1$-$C_4$)alkyl, —$SO_2$-alkyl, —$SO_2$-phenyl, pyridyl($C_1$-$C_4$)alkanoyl, thienyl($C_1$-$C_4$)alkanoyl, wherein the alkyl portion of the alkyl and alkanoyl groups are optionally substituted with halogen or $C_1$-$C_4$ alkoxy, wherein the aryl, and heteroaryl groups are optionally substituted with alkyl, alkoxy, halogen, $CF_3$, $OCF_3$, and R" is H, or $C_1$-$C_4$ alkyl.

In another aspect, the invention provides compounds of formula I-ii10, i.e., compounds according to any one of formulas I-ii1, I-ii2, I-ii3, I-ii4, I-ii5, I-ii6, I-ii7, I-ii8, or I-ii9, wherein $R_{10}$, $R_{11}$, and $R_3$, are all H. Preferably, at least one of $R_3$ and $R_4$ is halogen. More preferably, n is 2 or 3. Still more preferably, n is 3.

In another aspect, the invention provides a pharmaceutical composition comprising a compound of formula I and at least one pharmaceutically acceptable carrier, solvent, adjuvant and/or excipient.

Other preferred compounds of formula II, include those of formula X:

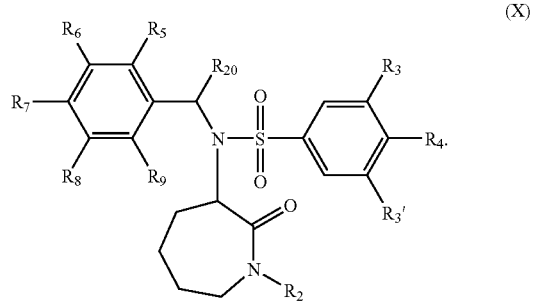

(X)

In one aspect, the invention provides compounds of formula X-a, i.e., compounds of formula X, wherein $R_6$ and $R_5$ together with the carbon atoms to which they are attached form a benzo group; or $R_6$ and $R_7$ together represent —O—$CH_2$—O—, or —O—$CH_2CH_2$—O—; or $R_7$ and $R_8$ together with the carbon atoms to which they are attached form a benzo group; or $R_5$ is H, $C_1$-$C_4$ alkyl optionally substituted with —$SO_2$-phenyl, halogen, $CF_3$, $C_1$-$C_4$ alkoxy (in one aspect, methoxy or ethoxy), morpholin-4-yl, phenyl, —O—($CH_2$)—C(O)O—($CH_2CH_3$), or cyano;

$R_6$ is H, F, Cl, Br, I, $CF_3$, $C_1$-$C_4$ alkoxy, $C_1$-$C_4$ alkoxycarbonyl, CN, $OCF_3$, $C_1$-$C_4$ alkyl (in one aspect, methyl or tert-butyl), —O-phenyl wherein the phenyl group is optionally substituted with F, $C_2$-$C_3$ alkenyl, methoxycarbonyl, or benzyloxy;

$R_7$ is H, methoxycarbonyl, methoxy, ethoxy, isopropoxy, ethoxy substituted with thiazol-5-yl, wherein the thiazolyl ring is substituted with methyl, —$SCH_3$, methyl, isopropyl, tert-butyl, isobutyl, F, Br, Cl, $CF_3$, $OCF_3$, cyano, $N(CH_3)_2$, $N(C_2$ alkyl substituted with Cl) ($C_2$ alkyl substituted with Cl), phenyl, phenyl substituted with methyl, benzyloxy, $NO_2$, —S(O)—$C_1$-$C_6$ alkyl, —$SO_2$—$C_1$-$C_6$ alkyl, $NH_2$, NH($C_1$-$C_6$ alkyl), N($C_1$-$C_6$ alkyl) ($C_1$-$C_6$ alkyl), —N($R_{16}$)C(O)$R_{17}$, —C(O)N$R_{30}R_{31}$, $C_1$-$C_2$ haloalkyl, phenyloxy, —O—$SO_2$-(4-chlorophenyl), —NH—C(O)—$CH_3$, —O—C(O)—$CH_3$, thiazolyl substituted with tert-butyl, or OH;

$R_8$ is H, halogen, $C_1$-$C_6$ alkoxy, $C_1$-$C_6$ alkyl;

$R_9$ is H, $C_1$-$C_4$ alkyl, $C_1$-$C_4$ alkoxy, halogen, or CN; and $R_{20}$ is H or methyl.

In another aspect, the invention provides compounds of formula X-a1, i.e., compounds of formula X wherein $R_4$ and $R_3$ together form a phenyl group; and $R_6$ is selected from H, F, Cl, Br, I, $CF_3$, methoxycarbonyl, methoxy, cyano, $OCF_3$, methyl, tert-butyl;

$R_7$ is H, methoxycarbonyl, methoxy, ethoxy, isopropoxy, ethoxy substituted with thiazol-5-yl, wherein the thiazolyl ring is substituted with methyl, —$SCH_3$, methyl, isopropyl, tert-butyl, isobutyl, F, Br, Cl, $CF_3$, $OCF_3$, cyano, $N(CH_3)_2$, $N(C_2$ alkyl substituted with Cl) ($C_2$ alkyl substituted with Cl), phenyl, phenyl substituted with methyl, benzyloxy, $NO_2$, —S(O)—$C_1$-$C_6$ alkyl, —$SO_2$—$C_1$-$C_6$ alkyl, $NH_2$, NH($C_1$-$C_6$ alkyl), N($C_1$-$C_6$ alkyl) ($C_1$-$C_6$ alkyl), —N($R_{16}$)C(O)$R_{17}$, —C(O)N$R_{30}R_{31}$, phenyloxy, —O—$SO_2$-(4-chlorophenyl), —NH—C(O)—$CH_3$, —O—C(O)—$CH_3$, thiazolyl substituted with tert-butyl, —S(O)—$C_1$-$C_6$ alkyl, —$SO_2$—$C_1$-$C_6$ alkyl, $NH_2$, NH($C_1$-$C_6$ alkyl), N($C_1$-$C_6$ alkyl) ($C_1$-$C_6$ alkyl), —N($R_{16}$)C(O)$R_{17}$, —C(O)N$R_{30}R_{31}$, $C_1$-$C_2$ haloalkyl, or OH.

In another aspect, the invention provides compounds of formula X-b, i.e., compounds of formula X-a wherein $R_4$ is H, F, Cl, Br, I, methoxy, tert-butyl, cyano, or —O-phenyl wherein the phenyl group is optionally substituted with F, $C_2$ alkenyl, methoxycarbonyl, or benzyloxy.

In another aspect, the invention provides compounds of formula X-c, i.e., compounds according to any one of formulas X-a or X-b wherein $R_6$, $R_7$ together are —O—$CH_2$—O—, or —O—$CH_2CH_2$—O—; or $R_5$ and $R_6$ together form a phenyl group.

In another aspect, the invention provides compounds of formula X-d, i.e., compounds of formula X-c wherein $R_6$, $R_7$ together are —O—$CH_2$—O—, or —O—$CH_2CH_2$—O—.

In another aspect, the invention provides compounds of formula X-e, i.e., compounds of formula X-c wherein $R_5$ and $R_6$ together form a phenyl group.

In another aspect, the invention provides compounds of formula X-f, i.e., compounds of formula X wherein $R_5$ is H, methyl, Cl, $CF_3$, methoxy, ethoxy, morpholin-4-yl, or —O—($CH_2$)—C(O))—($CH_2CH_3$);

$R_6$ is H, F, Cl, Br, I, $CF_3$, methoxycarbonyl, methoxy, cyano, $OCF_3$, methyl, or tert-butyl;

$R_7$ is H, methoxycarbonyl, methoxy, ethoxy, isopropoxy, ethoxy substituted with thiazol-5-yl, wherein the thiazolyl ring is substituted with methyl, —$SCH_3$, methyl, isopropyl, tert-butyl, isobutyl, F, Br, Cl, $CF_3$, $OCF_3$, cyano, $N(CH_3)_2$, $N(C_2$ alkyl substituted with Cl) ($C_2$ alkyl substituted with Cl), phenyl, phenyl substituted with methyl, benzyloxy, phenyloxy, —O—$SO_2$-(4-chlorophenyl), —NH—C(O)—$CH_3$, —O—C(O)—$CH_3$, thiazolyl substituted with tert-butyl, or OH;

$R_8$ is H, F, Cl, Br, methoxy, tert-butyl, cyano, —O-phenyl wherein the phenyl group is optionally substituted with halogen, $C_2$-$C_4$ alkenyl, $C_1$-$C_4$ alkoxycarbonyl, benzyloxy;

$R_9$ is H, F, Cl, Br, methyl, —$CH_2$—$SO_2$-phenyl, cyano, methoxy, and phenyl;

In another aspect, the invention provides compounds of formula X-g, i.e., compounds according to any one of formulas X, X-a, X-b, X-c, X-d, X-e, or X-f wherein $R_4$ is methyl, F, Cl or CF$_3$. In another aspect, R$_3$ is H. In still another aspect, R$_{3'}$ is also H. In yet another aspect, R$_4$ is F or Cl. In still another aspect, R$_4$ is Cl.

In another aspect, the invention provides compounds of formula X-h, i.e., compounds according to any one of formulas X, X-a, X-b, X-c, X-d, X-e, or X-f wherein R$_4$ is H. In another aspect, at least one of R$_3$ and R$_{3'}$ is not H. In another aspect, neither R$_3$ nor R$_{3'}$ is H.

In another aspect, the invention provides compounds of formula X-i, i.e., compounds according to any one of formulas X, X-a, X-b, X-c, X-d, X-e, or X-f wherein R$_2$ is H.

In another aspect, the invention provides compounds of formula X-j, i.e., compounds according to any one of formulas X, X-a, X-b, X-c, X-d, X-e, or X-f wherein R$_2$ is methyl.

In another aspect, the invention provides compounds of formula X-k, i.e., compounds of formula X wherein R$_5$, R$_6$, R$_8$, and R$_9$ are H;

R$_7$ is selected from methoxycarbonyl, methoxy, ethoxy, isopropoxy, —SCH$_3$, methyl, isopropyl, tert-butyl, isobutyl, F, Br, Cl, CF$_3$, OCF$_3$, cyano, N(CH$_3$)$_2$, N(C$_2$ alkyl substituted with Cl) (C$_2$ alkyl substituted with Cl), phenyl, phenyl substituted with methyl, benzyloxy, phenyloxy, —NH—C(O)—CH$_3$, —O—C(O)—CH$_3$, and thiazol-2-yl substituted with tert-butyl.

In another aspect, the invention provides compounds of formula X-l, i.e., compounds of formula X-k wherein R$_4$ is methyl, F, Cl or CF$_3$. In another aspect, R$_3$ is H. In still another aspect, R$_{3'}$ is also H. In yet still another aspect, R$_{20}$, and R$_2$ are also H. In yet another aspect, R$_4$ is F or Cl. In still another aspect, R$_4$ is Cl.

In another aspect, the invention provides compounds of formula X-m, i.e., compounds of formula X wherein R$_4$ is H. In another aspect, at least one of R$_3$ and R$_{3'}$ is not H. In another aspect, neither of R$_3$ nor R$_{3'}$ is H.

In another aspect, the invention provides compounds of formula X-n, i.e., compounds according to any one of formulas X-k, X-l, or X-m wherein R$_7$ is methoxycarbonyl, methoxy, ethoxy, isopropoxy, —SCH$_3$, methyl, isopropyl, tert-butyl, isobutyl, F, Br, Cl, CF$_3$, OCF$_3$, or cyano.

In another aspect, the invention provides compounds of formula X-o, i.e., compounds according to any one of formulas X-k, X-l, or X-m wherein R$_7$ is N(CH$_3$)$_2$, N(C$_2$ alkyl substituted with Cl) (C$_2$ alkyl substituted with Cl), phenyl, phenyl substituted with methyl, benzyloxy, phenyloxy, —NH—C(O)—CH$_3$, —O—C(O)—CH$_3$, or thiazol-2-yl substituted with tert-butyl.

In another aspect, the invention provides compounds of formula X-p, i.e., compounds according to formula X wherein R$_5$, R$_6$, R$_7$, and R$_8$ are H; R$_9$ is selected from F, Cl, Br, methyl, methyl substituted with —SO$_2$-phenyl, cyano, methoxy, and phenyl.

In another aspect, the invention provides compounds of formula X-q, i.e., compounds according to formula X-p wherein R$_4$ is methyl, F, Cl or CF$_3$. In another aspect, R$_3$ is H. In still another aspect, R$_{3'}$ is also H. In yet still another aspect, R$_2$ is also H. In yet another aspect, R$_4$ is F or Cl. In still another aspect, R$_4$ is Cl.

In another aspect, the invention provides compounds of formula X-r, i.e., compounds according to formula X-p wherein R$_4$ is H. In another aspect, at least one of R$_3$ and R$_{3'}$ is not H. In another aspect, neither of R$_3$ nor R$_{3'}$ is H.

In another aspect, the invention provides compounds of formula X-s, i.e., compounds according to any one of formulas X-p, X-q, or X-r wherein R$_5$ is F, Cl, Br, methyl, or methoxy.

In another aspect, the invention provides compounds of formula X-t, i.e., compounds according to any one of formulas X-p, X-q, or X-r wherein R$_5$ is methyl substituted with —SO$_2$-phenyl, cyano, or phenyl.

In another aspect, the invention provides compounds of formula X-u, i.e., compounds of formula X wherein R$_6$, R$_7$, R$_8$, and R$_9$ are H; and R$_5$ is ethoxy, morpholin-4-yl, or —O—(CH$_2$)—C(O)O—(CH$_2$CH$_3$).

In another aspect, the invention provides compounds of formula X-v, i.e., compounds of formula X-u wherein R$_4$ is methyl, F, Cl or CF$_3$. In another aspect, R$_3$ is H. In still another aspect, R$_{3'}$ is also H. In yet still another aspect, R$_2$, and R$_{20}$, are also H. In yet another aspect, R$_4$ is F or Cl. In still another aspect, R$_4$ is Cl.

In another aspect, the invention provides compounds of formula X-w, i.e., compounds of formula X-u wherein R$_4$ is H. In another aspect, at least one of R$_3$ and R$_{3'}$ is not H. In another aspect, neither of R$_3$ nor R$_{3'}$ is H.

In another aspect, the invention provides compounds of formula X-x, i.e., compounds of formula X wherein R$_5$, R$_7$, R, and R$_9$ are H;

R$_6$ is Cl, Br, I, CF$_3$, methoxycarbonyl, methoxy, cyano, OCF$_3$, or methyl.

In another aspect, the invention provides compounds of formula X-y, i.e., compounds of formula X-x wherein R$_4$ is methyl, F, Cl or CF$_3$. In another aspect, R$_3$ is H. In still another aspect, R$_{3'}$ is also H. In yet still another aspect, R$_2$, and R$_{20}$, are also H. In yet another aspect, R$_4$ is F or Cl. In still another aspect, R$_4$ is Cl.

In another aspect, the invention provides compounds of formula X-z, i.e., compounds of formula X-x wherein R$_4$ is H. In another aspect, at least one of R$_3$ and R$_{3'}$ is not H. In another aspect, neither of R$_3$ nor R$_{3'}$ is H.

In another aspect, the invention provides compounds of formula X-aa, i.e., compounds according to any one of formulas X-p, X-q, or X-r wherein R$_6$ is Cl, Br, I, CF$_3$, or OCF$_3$.

In another aspect, the invention provides compounds of formula X-bb, i.e., compounds according to any one of formulas X-p, X-q, or X-r wherein R$_6$ is methoxycarbonyl, methoxy, cyano, or methyl.

In another aspect, the invention provides compounds of formula X-cc, i.e., compounds of formula X wherein R$_5$, R$_6$, R$_7$, and R$_9$ are H;

R$_8$ is —O-phenyl wherein the phenyl group is substituted with F, C$_2$ alkenyl, or benzyloxy.

In another aspect, the invention provides compounds of formula X-dd, i.e., compounds of formula X-cc wherein R$_4$ is methyl, F, Cl or CF$_3$. In another aspect, R$_3$ is H. In still another aspect, R$_{3'}$ is also H. In yet another aspect, R$_2$, R$_{20}$ are also H. In yet another aspect, R$_4$ is F or Cl. In still another aspect, R$_4$ is Cl.

In another aspect, the invention provides compounds of formula X-ee, i.e., compounds of formula X-cc wherein R$_4$ is H. In another aspect, at least one of R$_3$ and R$_{3'}$ is not H. In another aspect, neither of R$_3$ nor R$_{3'}$ is H.

Preferred compounds of formula X include those of formula XI:

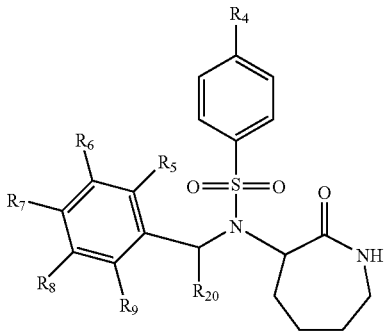

(XI)

wherein $R_4$ is methyl, F, Cl or $CF_3$.

Other preferred compounds of formula X include those of formula

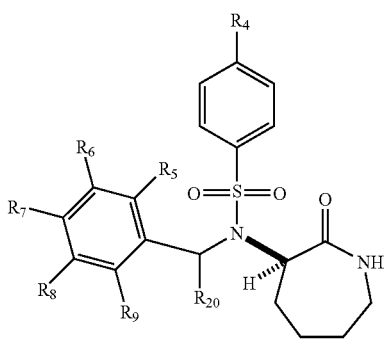

(XII)

wherein $R_4$ is methyl, F, Cl or $CF_3$.

In yet another aspect, the invention provides compounds of formula X-ff, i.e., compounds according to any one of formulas X-a, XI, or XII, wherein at least two of $R_5$, $R_6$, $R_7$, $R_8$ and $R_9$ are hydrogen.

In another aspect, the invention provides compounds of formula X-gg, i.e., compounds of formula X-ff, wherein one of $R_5$, $R_6$, $R_7$, $R_8$ and $R_9$ is —$SCH_3$, —$S(O)CH_3$, or —$SO_2CH_3$. More preferably, one of $R_5$, $R_6$, $R_7$, $R_8$, and $R_9$ is —$SCH_3$, —$S(O)CH_3$, or —$SO_2CH_3$ while the other four variables are all H.

In another aspect, the invention provides compounds of formula X-hh, i.e., compounds of formula X-ff, wherein one of $R_5$, $R_6$, $R_7$, $R_8$ and $R_9$ is

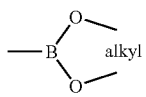

m wherein the alkyl is a divalent $C_2$-$C_8$ alkyl. Still more preferably one of $R_5$, $R_6$, $R_7$, $R_8$ and $R_9$ is

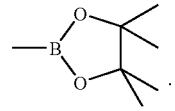

More preferably, four of $R_5$, $R_6$, $R_7$, $R_8$ and $R_9$ are H.

In another aspect, the invention provides compounds of formula X-ii, i.e., compounds of formula X-ff, wherein one of $R_5$, $R_6$, $R_7$, $R_8$ and $R_9$ is CN, —$CO_2H$, or mono halo $C_1$-$C_2$ alkyl (preferably —$CH_2Cl$). Still more preferably, four of $R_5$, $R_6$, $R_7$, $R_8$ and $R_9$ are H.

In another aspect, the invention provides compounds of formula X-jj, i.e., compounds of formula X-ff, wherein one of $R_5$, $R_6$, $R_7$, $R_8$ and $R_9$ is —$N(R_{16})C(O)R_{17}$. More preferably, three of $R_5$, $R_6$, $R_8$ and $R_9$ are H. Still more preferably, $R_7$ is —$N(R_{16})C(O)R_{17}$.

In another aspect, the invention provides compounds of formula X-kk, i.e., compounds of formula X-jj, wherein $R_{16}$ is H or $C_1$-$C_4$ alkyl (when $R_{16}$ is alkyl, it is preferably methyl or ethyl, more preferably it is methyl.)

In another aspect, the invention provides compounds of formula X-ll, i.e., compounds of formula X-kk, wherein $R_{17}$ is $C_1$-$C_4$ alkoxy, phenyloxy, phenyl $C_1$-$C_4$ alkyl, phenyl, $C_3$-$C_6$ cycloalkyl, $C_1$-$C_4$ alkyl, pyridyl, pyrazinyl, pyrimidinyl, or —$NR_{18}R_{19}$, wherein $R_{18}$, and $R_{19}$ are independently H, $C_1$-$C_6$ alkyl, phenyl, naphthyl, pyridyl, pyrrolyl, piperazinyl, pyrimidinyl, furanyl, thienyl, pyrazolyl, imidazolyl, isoxazolyl, piperidinyl, morpholinyl, piperazinyl, pyrrolidinyl, imidazolidinyl, or phenyl($C_1$-$C_6$)alkyl, wherein the cyclic portions of each are optionally substituted with 1, 2, or 3 groups that are independently $C_1$-$C_4$ alkyl, $C_1$-$C_4$ alkoxy, halogen, hydroxyl, $CF_3$, or $OCF_3$.

In another aspect, the invention provides compounds of formula X-mm, i.e., compounds of formula X-ll, wherein $R_{17}$ is $C_1$-$C_4$ alkoxy, cyclohexyl, or $C_1$-$C_4$ alkyl.

In another aspect, the invention provides compounds of formula X-nn, i.e., compounds of formula X-ll, wherein $R_{17}$ is $C_1$-$C_4$ alkoxy.

In another aspect, the invention provides compounds of formula X-oo, i.e., compounds of formula X-ll, wherein $R_{17}$ is cyclohexyl, or $C_1$-$C_4$ alkyl.

In another aspect, the invention provides compounds of formula X-pp, i.e., compounds of formula X-ll, wherein $R_{17}$ is phenyloxy, phenyl $C_1$-$C_4$ alkyl (preferably benzyl or phenethyl, more preferably, benzyl), or phenyl.

In another aspect, the invention provides compounds of formula X-qq, i.e., compounds of formula X-ll, wherein $R_{17}$ is pyridyl, pyrazinyl, or pyrimidinyl.

In another aspect, the invention provides compounds of formula X-qq, i.e., compounds of formula X-ll, wherein $R_{17}$ is —$NR_{18}R_{19}$, and $R_{18}$ is H.

In another aspect, the invention provides compounds of formula X-rr, i.e., compounds of formula X-qq, wherein $R_{19}$ is H, $C_1$-$C_6$ alkyl, phenyl, naphthyl, pyridyl, pyrrolyl, piperazinyl, pyrimidinyl, furanyl, thienyl, pyrazolyl, imidazolyl, isoxazolyl, piperidinyl, morpholinyl, piperazinyl, pyrrolidinyl, imidazolidinyl, or phenyl($C_1$-$C_6$)alkyl, wherein the cyclic portions of each are optionally substituted with 1, 2, or 3 groups that are independently $C_1$-$C_4$ alkyl, $C_1$-$C_4$ alkoxy, halogen, hydroxyl, $CF_3$, or $OCF_3$.

In another aspect, the invention provides compounds of formula X-ss, i.e., compounds of formula X-ff, wherein $R_7$ is —($C_1$-$C_4$ alkyl)-C(O)$NR_{30}R_{31}$, —O—($C_1$-$C_4$ alkyl)-C(O)$NR_{30}R_{31}$, —C(O)$NR_{30}R_{31}$. In another aspect, $R_7$ is —($C_1$-$C_2$ alkyl)-C(O)$NR_{30}R_{31}$, —O—($C_1$-$C_2$ alkyl)-C(O)$NR_{30}R_{31}$, or —C(O)NR$_{30}$R$_{31}$. In still another aspect, R$_7$ is —(C$_1$-C$_2$ alkyl)-C(O)NR$_{30}$R$_{31}$ (where the C$_1$-C$_2$ alkyl is —CH$_2$—, —CH$_2$CH$_2$—, or —CH(CH$_3$)—.) In yet still another aspect, R$_7$ is —O—(C$_1$-C$_2$ alkyl)-C(O)NR$_{30}$R$_{31}$ (where the —O—(C$_1$-C$_2$ alkyl) is —O—CH$_2$—, —O—CH$_2$CH$_2$—, or —O—CH(CH$_3$)—.) In still yet another aspect, R$_7$ is —C(O)NR$_{30}$R$_{31}$.

In another aspect, the invention provides compounds of formula X-tt, i.e., compounds of formula X-ss, wherein R$_{30}$, R$_{31}$, and the nitrogen to which they are attached form a heterocycloalkyl ring that is pyrrolidinyl, piperidinyl, morpholinyl, dihydro 1H-indolyl, tetrahydroisoquinolinyl, tetrahydroquinolinyl, or piperazinyl, wherein the heterocyclic ring is optionally substituted with 1, 2, or 3 groups that are independently C$_1$-C$_4$ alkyl, C$_1$-C$_4$ alkoxy, halo, C$_1$-C$_4$ thioalkoxy, OH, NH$_2$, NH(C$_1$-C$_4$ alkyl), N(C$_1$-C$_4$ alkyl) (C$_1$-C$_4$ alkyl), CF$_3$, OCF$_3$, phenyl, 4-halophenyl, —(C$_1$-C$_4$ alkyl)-N(H or C$_1$-C$_4$ alkyl)-phenyl, C$_1$-C$_4$ hydroxyalkyl, phenyl C$_1$-C$_4$ alkoxy, phenyl C$_1$-C$_4$ alkyl, phenyl C$_1$-C$_4$ alkanoyl, —CH$_2$-pyrrolidinyl, C(O)NH$_2$, C(O)NH(C$_1$-C$_6$ alkyl), C(O)N(C$_1$-C$_6$ alkyl) (C$_1$-C$_6$ alkyl), C$_1$-C$_6$ alkoxycarbonyl, C$_2$-C$_6$ alkanoyl, pyrazolyl, pyrrolyl, pyridyl, furanyl, morpholinyl, or —SO$_2$—(C$_1$-C$_4$ alkyl).

In another aspect, the invention provides compounds of formula X-uu, i.e., compounds of formula X-tt, wherein R$_{30}$, R$_{31}$, and the nitrogen to which they are attached form a heterocycloalkyl ring that is optionally substituted with 1 or 2 groups that are independently C$_1$-C$_4$ alkyl, C$_1$-C$_4$ alkoxy, halo, C$_1$-C$_4$ thioalkoxy, OH, NH$_2$, NH(C$_1$-C$_4$ alkyl), N(C$_1$-C$_4$ alkyl) (C$_1$-C$_4$ alkyl), —CH$_2$-pyrrolidinyl, —C(O)NH$_2$, —C(O)NH(C$_1$-C$_4$ alkyl), or —C(O)N(C$_1$-C$_4$ alkyl) (C$_1$-C$_4$ alkyl), CF$_3$, OCF$_3$, phenyl, 4-halophenyl, or —(C$_1$-C$_4$ alkyl)-N(H or C$_1$-C$_4$ alkyl)-phenyl.

In another aspect, the invention provides compounds of formula X-vv, i.e., compounds of formula X-tt, wherein R$_{30}$, R$_{31}$, and the nitrogen to which they are attached form a heterocycloalkyl ring that is optionally substituted with 1 or 2 groups that are independently C(O)NH$_2$, C(O)NH(C$_1$-C$_4$ alkyl), C(O)N(C$_1$-C$_4$ alkyl) (C$_1$-C$_4$ alkyl), C$_1$-C$_4$ alkoxycarbonyl, C$_2$-C$_6$ alkanoyl, pyrazolyl, pyrrolyl, pyridyl, or —SO$_2$—(C$_1$-C$_4$ alkyl).

In another aspect, the invention provides compounds of formula X-vv1, i.e., compounds of formula X-tt, wherein R$_{30}$, R$_{31}$, and the nitrogen to which they are attached form a pyrrolidinyl ring that is optionally substituted with phenyl, methyl, ethyl, —CH$_2$OH, —CH$_2$NH-phenyl, —CH$_2$-pyrrolidinyl, —C(O)NH$_2$, —C(O)NH(C$_1$-C$_4$ alkyl), or —C(O)N(C$_1$-C$_4$ alkyl) (C$_1$-C$_4$ alkyl).

In another aspect, the invention provides compounds of formula X-vv2, i.e., compounds of formula X-tt, wherein R$_{30}$, R$_{31}$, and the nitrogen to which they are attached form dihydro 1H-indolyl.

In another aspect, the invention provides compounds of formula X-ww, i.e., compounds of formula X-ss, wherein R$_{31}$ is H, C$_1$-C$_4$ alkyl (in another aspect, methyl or ethyl), C$_2$-C$_6$ alkenyl (in another aspect, allyl), C$_3$-C$_6$ cycloalkyl (in another aspect, cyclopropyl, cyclohexyl, tetrahydronaphthyl, or indanyl), hydroxy C$_1$-C$_4$ alkyl (in another aspect, C$_2$ hydroxyalkyl), phenyl C$_1$-C$_4$ alkyl (in another aspect, benzyl, phenethyl or phenpropyl), or pyridyl C$_1$-C$_4$ alkyl (in another aspect, —CH$_2$-pyridyl).

In another aspect, the invention provides compounds of formula X-ww1, i.e., compounds of formula X-ww, wherein R$_{31}$ is H.

In another aspect, the invention provides compounds of formula X-xx, i.e., compounds of either formula X-ww or formula X-ww1, wherein R$_{30}$ is H or C$_1$-C$_6$ alkyl, wherein the alkyl group is optionally substituted with 1, 2, or 3 groups that are independently halogen, OH, phenyl, or alkoxy optionally substituted with OH or phenyl.

In another aspect, the invention provides compounds of formula X-yy, i.e., compounds of either formula X-ww or formula X-ww1, wherein R$_{30}$ is phenyl, —CH$_2$CH$_2$-phenyl, —CH(CH$_3$)-phenyl, —C(CH$_3$)$_2$-phenyl, benzyl, naphthyl C$_1$-C$_6$ alkyl, or phenyl C$_1$-C$_4$ alkanoyl, wherein the phenyl portions of the above are optionally substituted with 1, 2, or 3 groups that are C$_1$-C$_4$ alkyl, C$_1$-C$_4$ alkoxy, halo, C$_1$-C$_4$ thioalkoxy, OH, NH$_2$, NH(C$_1$-C$_4$ alkyl), N(C$_1$-C$_4$ alkyl) (C$_1$-C$_4$ alkyl), CF$_3$, OCF$_3$, phenyl, 4-halophenyl, —(C$_1$-C$_4$ alkyl)-N(H or C$_1$-C$_4$ alkyl)-phenyl, C$_1$-C$_4$ hydroxyalkyl, phenyl C$_1$-C$_4$ alkoxy, phenyl C$_1$-C$_4$ alkyl, phenyl C$_1$-C$_4$ alkanoyl, C(O)NH$_2$, C(O)NH(C$_1$-C$_4$ alkyl), C(O)N(C$_1$-C$_4$ alkyl) (C$_1$-C$_4$ alkyl), C$_1$-C$_4$ alkoxycarbonyl, C$_2$-C$_4$ alkanoyl, pyrazolyl, pyrrolyl, pyridyl, furanyl, morpholinyl, or —SO$_2$—(C$_1$-C$_4$ alkyl).

In another aspect, the invention provides compounds of formula X-zz, i.e., compounds of formula X-yy, wherein the cyclic portions are optionally substituted with 1, 2, or 3 groups that are C$_1$-C$_4$ alkyl, C$_1$-C$_4$ alkoxy, halo, C$_1$-C$_4$ thioalkoxy, OH, CF$_3$, OCF$_3$, phenyl, 4-halophenyl, C$_1$-C$_4$ hydroxyalkyl, or —SO$_2$—(C$_1$-C$_4$ alkyl).

In another aspect, the invention provides compounds of formula X-aaa, i.e., compounds of formula X-zz, wherein the phenyl portions are optionally substituted with 1 or 2 groups that are independently halogen, methyl, methoxy, CF$_3$ or OCF$_3$.

In another aspect, the invention provides compounds of formula X-aa1, i.e., compounds of either formula X-ww or formula X-ww1, wherein R$_{30}$ is phenyl, —CH(CH$_3$)-phenyl, or benzyl, wherein the phenyl portions of the above are optionally substituted with 1, 2, or 3 groups that are C$_1$-C$_4$ alkyl, C$_1$-C$_4$ alkoxy, halo, C$_1$-C$_4$ thioalkoxy, OH, NH$_2$, NH(C$_1$-C$_4$ alkyl), N(C$_1$-C$_4$ alkyl) (C$_1$-C$_4$ alkyl), CF$_3$, OCF$_3$, phenyl, 4-halophenyl, —(C$_1$-C$_4$ alkyl)-N(H or C$_1$-C$_4$ alkyl)-phenyl, C$_1$-C$_4$ hydroxyalkyl, phenyl C$_1$-C$_4$ alkoxy, phenyl C$_1$-C$_4$ alkyl, phenyl C$_1$-C$_4$ alkanoyl, C(O)NH$_2$, C(O)NH(C$_1$-C$_4$ alkyl), C(O)N(C$_1$-C$_4$ alkyl) (C$_1$-C$_4$ alkyl), C$_1$-C$_4$ alkoxycarbonyl, C$_2$-C$_4$ alkanoyl, pyrazolyl, pyrrolyl, pyridyl, furanyl, morpholinyl, or —SO$_2$—(C$_1$-C$_4$ alkyl).

In another aspect, the invention provides compounds of formula X-bbb, i.e., compounds of formula X-zz, wherein the phenyl portions are substituted with 2 groups, one of which is a halogen and the other is either a halogen, a methyl or methoxy group.

In another aspect, the invention provides compounds of formula X-ccc, i.e., compounds of either formula X-ww or formula X-ww1, wherein R$_{30}$ is C$_2$-C$_6$ alkenyl (in one aspect C$_3$-C$_4$ alkenyl), or C$_2$-C$_4$ alkynyl (in one aspect, C$_3$ alkynyl.)

In another aspect, the invention provides compounds of formula X-ddd, i.e., compounds of either formula X-ww or formula X-ww1, wherein R$_{30}$ is C$_3$-C$_6$ cycloalkyl, or cyclohexenyl, each of which is optionally substituted with 1 or 2, groups that are independently C$_1$-C$_4$ alkyl, C$_1$-C$_4$ alkoxy, —CH$_2$OH, —O—benzyl, halo, OH, —C(O)NH$_2$, —C(O)NH(C$_1$-C$_6$ alkyl), or —C(O)N(C$_1$-C$_6$ alkyl) (C$_1$-C$_6$ alkyl). In another aspect, the cycloalkyl and cyclohexenyl groups are not substituted.

In another aspect, the invention provides compounds of formula X-eee, i.e., compounds of either formula X-ww or formula X-ww1, wherein R$_{30}$ is piperidinyl optionally substituted with C$_1$-C$_4$ alkyl, C$_1$-C$_4$ alkoxycarbonyl, or C$_2$-C$_6$ alkanoyl, tetrahydronaphthyl, tetrahydrofuranyl, pyrrolidinyl, pyrazolyl, dihydrofuranonyl, naphthyl, quinuclidinyl, 4H-pyranonyl (preferably 3-hydroxy 4H-pyranonyl), 1,4-dioxanyl, pyridyl, imidazolyl, thiazolyl, oxazolyl, or indolyl, each of which is optionally substituted with 1, 2, or 3 groups that are independently $C_1$-$C_4$ alkyl, $C_1$-$C_4$ alkoxy, halo, $C_1$-$C_4$ thioalkoxy, OH, $NH_2$, $NH(C_1$-$C_4$ alkyl), $N(C_1$-$C_4$ alkyl)($C_1$-$C_4$ alkyl), $CF_3$, $OCF_3$, phenyl, 4-(chloro or fluoro)phenyl, —($C_1$-$C_4$ alkyl)-N(H or $C_1$-$C_4$ alkyl)-phenyl, $C_1$-$C_4$ hydroxyalkyl, phenyl $C_1$-$C_4$ alkoxy, phenyl $C_1$-$C_4$ alkyl, phenyl $C_1$-$C_4$ alkanoyl, $C(O)NH_2$, $C(O)NH(C_1$-$C_6$ alkyl), $C(O)N(C_1$-$C_4$ alkyl)($C_1$-$C_4$ alkyl), $C_1$-$C_4$ alkoxycarbonyl, $C_2$-$C_4$ alkanoyl, pyrazolyl, pyrrolyl, pyridyl, furanyl, or —$SO_2$—($C_1$-$C_4$ alkyl). In another aspect, $R_{30}$ is not substituted.

In another aspect, the invention provides compounds of formula X-fff, i.e., compounds of either formula X-ww or formula X-ww1, wherein $R_{30}$ is tetrahydronaphthyl $C_1$-$C_4$ alkyl, tetrahydrofuranyl $C_1$-$C_4$ alkyl, pyridyl $C_1$-$C_4$ alkyl, pyrazolyl $C_1$-$C_4$ alkyl, cyclohexenyl $C_1$-$C_4$ alkyl, pyrrolidinyl $C_1$-$C_4$ alkyl, pyrazolyl $C_1$-$C_4$ alkyl, quinuclidinyl $C_1$-$C_4$ alkyl, 4H-pyranonyl $C_1$-$C_4$ alkyl (preferably 3-hydroxy 4H-pyranonyl $C_1$-$C_4$ alkyl), pyrazinyl $C_1$-$C_4$ alkyl, pyrrolidinyl $C_1$-$C_4$ alkyl, furanyl $C_1$-$C_4$ alkyl, thienyl $C_1$-$C_4$ alkyl, pyrrolyl $C_1$-$C_4$ alkyl, 2,5-dihydro-1H-pyrrolyl $C_1$-$C_4$ alkyl, thiazolyl $C_1$-$C_4$ alkyl, biphenyl $C_1$-$C_4$ alkyl, benzothienyl $C_1$-$C_4$ alkyl, furanyl $C_1$-$C_4$ alkyl, isoxazolyl $C_1$-$C_4$ alkyl, or 1,4-dioxanyl $C_1$-$C_4$ alkyl, wherein the alkyl portions of the above are optionally substituted with 1 or 2 groups that are independently $NH_2$, $NH(C_1$-$C_4$ alkyl), $N(C_1$-$C_4$ alkyl)($C_1$-$C_4$ alkyl), OH, $C_1$-$C_4$ thioalkoxy, CN, halogen, or $C_1$-$C_4$ alkoxy optionally substituted with OH or phenyl; and wherein the cyclic portion of $R_{30}$ is optionally substituted with 1, 2, or 3 groups that are independently $C_1$-$C_4$ alkyl, $C_1$-$C_4$ alkoxy, halo, $C_1$-$C_4$ thioalkoxy, OH, $NH_2$, $NH(C_1$-$C_4$ alkyl), $N(C_1$-$C_4$ alkyl)($C_1$-$C_4$ alkyl), $CF_3$, $OCF_3$, phenyl, 4-(chloro or fluoro) phenyl, —($C_1$-$C_4$ alkyl)-N(H or $C_1$-$C_4$ alkyl)-phenyl, $C_1$-$C_4$ hydroxyalkyl, phenyl $C_1$-$C_4$ alkoxy, phenyl $C_1$-$C_4$ alkyl, phenyl $C_1$-$C_4$ alkanoyl, $C(O)NH_2$, $C(O)NH(C_1$-$C_4$ alkyl), $C(O)N(C_1$-$C_4$ alkyl)($C_1$-$C_4$ alkyl), $C_1$-$C_4$ alkoxycarbonyl, $C_2$-$C_4$ alkanoyl, pyrazolyl, pyrrolyl, pyridyl, or —$SO_2$—($C_1$-$C_4$ alkyl).

In another aspect, the invention provides compounds of formula X-ggg, i.e., compounds of formula fff, wherein $R_{30}$ is —$CH_2$-tetrahydronaphthyl, —$CH_2$-tetrahydrofuranyl, —$CH_2$-pyridyl, —$CH_2$-pyrazolyl, —$CH_2$-cyclohexenyl, —$CH_2$-pyrrolidinyl, —$CH_2$-pyrazolyl, —$CH_2$-quinuclidinyl, —$CH_2$-(4H-pyranonyl) (preferably —$CH_2$-(3-hydroxy 4H-pyranonyl), —$CH_2$-pyrazinyl, —$CH_2$-pyrrolidinyl, —$CH_2$-furanyl, —$CH_2$-thienyl, —$CH_2$-pyrrolyl, —$CH_2$-(2, 5-dihydro-1H-pyrrolyl), —$CH_2$-thiazolyl,

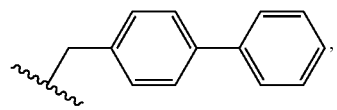
,

—$CH_2$-benzothienyl, —$CH_2$-furanyl, —$CH_2$-isoxazolyl, or —$CH_2$-(1,4-dioxanyl), wherein the alkyl portions of the above are optionally substituted with OH, and wherein the cyclic portion of $R_{30}$ is optionally substituted with 1, or 2, or 3 groups that are independently $C_1$-$C_4$ alkyl, $C_1$-$C_4$ alkoxy, halo, $C_1$-$C_4$ thioalkoxy, OH, $NH_2$, $NH(C_1$-$C_4$ alkyl), $N(C_1$-$C_4$ alkyl)($C_1$-$C_4$ alkyl), $CF_3$, $OCF_3$, phenyl, 4-(chloro or fluoro) phenyl, —($C_1$-$C_4$ alkyl)-N(H or $C_1$-$C_4$ alkyl)-phenyl, $C_1$-$C_4$ hydroxyalkyl, benzyloxy, benzyl, phenyl $C_1$-$C_4$ alkanoyl, $C(O)NH_2$, $C(O)NH(C_1$-$C_4$ alkyl), $C(O)N(C_1$-$C_4$ alkyl)($C_1$-$C_4$ alkyl), $C_1$-$C_4$ alkoxycarbonyl, $C_2$-$C_4$ alkanoyl, pyrazolyl, pyrrolyl, pyridyl, or —$SO_2CH_3$.

In another aspect, the invention provides compounds of formula X-hhh, i.e., compounds of formula ff, wherein $R_7$ is triazolyl, tetrazolyl, pyridyl, oxazolyl, or oxadiazolyl, each of which is optionally substituted with 1, 2, or 3 groups that are independently $C_1$-$C_6$ alkyl, $C_1$-$C_6$ alkoxy, $C_1$-$C_4$ alkoxy $C_1$-$C_4$ alkyl, pyridyl, pyrrolyl, imidazolyl, furanyl, thienyl optionally substituted with 1 or 2 methyls, halogen, $C_3$-$C_6$ cycloalkyl (in one aspect, cyclohexyl) or phenyl optionally substituted with 1, 2, 3, 4 or 5 groups that are independently halogen, OH, $C_1$-$C_6$ alkyl, $C_1$-$C_4$ alkoxy, $CF_3$, $OCF_3$, CN, or $C_1$-$C_6$ thioalkoxy.

In another aspect, the invention provides compounds of formula X-iii, i.e., compounds of formula hhh, wherein $R_7$ is oxadiazolyl, which is optionally substituted with 1 group that is independently $C_1$-$C_4$ alkyl, $C_1$-$C_4$ alkoxy, $C_1$-$C_4$ alkoxy $C_1$-$C_4$ alkyl, pyridyl, pyrrolyl, imidazolyl, furanyl, thienyl optionally substituted with 1 or 2 methyls, halogen, $C_3$-$C_6$ cycloalkyl (in one aspect, cyclohexyl) or phenyl optionally substituted with 1, 2, 3, 4 or 5 groups that are independently halogen, OH, $C_1$-$C_4$ alkyl, $C_1$-$C_4$ alkoxy, $CF_3$, $OCF_3$, CN, or $C_1$-$C_4$ thioalkoxy.

In another aspect, the invention provides compounds of formula X-jjj, i.e., compounds of formula iii, wherein $R_7$ is oxadiazolyl, which is substituted with 1 group that is $C_1$-$C_4$ alkyl, $C_1$-$C_4$ alkoxy, $C_1$-$C_4$ alkoxy $C_1$-$C_4$ alkyl, or halogen.

In another aspect, the invention provides compounds of formula X-kkk, i.e., compounds of formula iii, wherein $R_7$ is oxadiazolyl, which is substituted with 1 group that is pyridyl, pyrrolyl, imidazolyl, furanyl, thienyl optionally substituted with 1 or 2 methyls, $C_3$-$C_6$ cycloalkyl (in one aspect, cyclohexyl) or phenyl optionally substituted with 1, 2, 3, 4 or 5 groups that are independently halogen, OH, $C_1$-$C_4$ alkyl, $C_1$-$C_4$ alkoxy, $CF_3$, $OCF_3$, CN, or $C_1$-$C_4$ thioalkoxy.

In another aspect, the invention provides compounds of formula X-lll, i.e., compounds of formula kkk, wherein $R_7$ is oxadiazolyl, which is substituted with 1 group that is pyridyl, or phenyl, wherein the phenyl is optionally substituted with 1, 2, or 3 groups that are independently halogen, OH, $C_1$-$C_4$ alkyl, $C_1$-$C_4$ alkoxy, $CF_3$, $OCF_3$, CN, or $C_1$-$C_4$ thioalkoxy. In another aspect, the phenyl group is unsubstituted or mono-substituted. In still another aspect, when the phenyl group is mono-substituted, it is substituted at the 3 or 4 position.

In another aspect, the invention provides compounds of formula X-mmm, i.e., compounds of formula kkk, wherein $R_7$ is oxadiazolyl, which is substituted with 1 group that is pyrrolyl, imidazolyl, furanyl, thienyl optionally substituted with 1 or 2 methyls, $C_3$-$C_6$ cycloalkyl (in one aspect, cyclohexyl)

In another aspect, the invention provides compounds of formula X-nnn, i.e., compounds of formula hhh, wherein $R_7$ is tetrazolyl.

DEFINITIONS

The definitions and explanations below are for the terms as used throughout this entire document including both the specification and the claims.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Where multiple substituents are indicated as being attached to a structure, it is to be understood that the substituents can be the same or different. Thus for example "$R_m$ optionally substituted with 1, 2 or 3 $R_q$ groups" indicates that $R_m$ is substituted with 1, 2, or 3 $R_q$ groups where the $R_q$ groups can be the same or different.

APP, amyloid precursor protein, is defined as any APP polypeptide, including APP variants, mutations, and isoforms, for example, as disclosed in U.S. Pat. No. 5,766,846. A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Pharmaceutically acceptable refers to those properties and/or substances that are acceptable to the patient from a toxicological and/or safety point of view.

A therapeutically effective amount is defined as an amount effective to reduce or lessen at least one symptom of the disease being treated or to reduce or delay onset of one or more clinical markers or symptoms of the disease.

By "alkyl" and "$C_1$-$C_6$ alkyl" in the present invention is meant straight or branched chain alkyl groups having 1-6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$-$C_{10}$" indicates a maximum of 10 carbons.

By "alkoxy" and "$C_1$-$C_6$ alkoxy" in the present invention is meant straight or branched chain alkyl groups having 1-6 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy.

By the term "halogen" in the present invention is meant fluorine, bromine, chlorine, and/or iodine.

"Alkenyl" and "$C_2$-$C_6$ alkenyl" means straight and branched hydrocarbon radicals having from 2 to 6 carbon atoms and from one to three double bonds and includes, for example, ethenyl, propenyl, 1-but-3-enyl, 1-pent-3-enyl, 1-hex-5-enyl and the like.

"Alkynyl" and "$C_2$-$C_6$ alkynyl" means straight and branched hydrocarbon radicals having from 2 to 6 carbon atoms and one or two triple bonds and includes ethynyl, propynyl, butynyl, pentyn-2-yl and the like.

As used herein, the term "cycloalkyl" refers to saturated carbocyclic radicals having three to twelve carbon atoms. The cycloalkyl can be monocyclic, a polycyclic fused system, or a bi or polycyclic bridged system, such as adamantyl or bicyclo[2.2.1]heptyl. Cycloalkyl groups can also be fused to a phenyl group. Examples of such cycloalkyl groups include 1,2,3,4-tetrahydronaphthyl, indanyl, cyclopropyl, cyclobutyl, cyclopentyl and cyclohexyl. Preferred cycloalkyl groups are cyclopentyl, cyclohexyl, and cycloheptyl. The cycloalkyl groups herein are unsubstituted or, as specified, substituted in one or more substitutable positions with various groups. For example, such cycloalkyl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "aryl" is meant an aromatic carbocyclic group having a single ring (e.g., phenyl) or multiple condensed rings in which at least one is aromatic, (e.g., 1,2,3,4-tetrahydronaphthyl, naphthyl), which is optionally mono-, di-, or trisubstituted. Preferred aryl groups of the present invention are phenyl, 1-naphthyl, 2-naphthyl, indanyl, indenyl, dihydronaphthyl, fluorenyl, tetralinyl or 6,7,8,9-tetrahydro-5H-benzo[a]cycloheptenyl. The aryl groups herein are unsubstituted or, as specified, substituted in one or more substitutable positions with various groups. For example, such aryl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "heteroaryl" is mean at least one or more aromatic ring systems of 5-, 6-, or 7-membered rings which includes fused ring systems of 9-11 atoms containing at least one and up to four heteroatoms selected from nitrogen, oxygen, or sulfur. Preferred heteroaryl groups of the present invention include pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. The heteroaryl groups herein are unsubstituted or, as specified, substituted in one or more substitutable positions with various groups. For example, such heteroaryl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "heterocycle", "heterocycloalkyl" or "heterocyclyl" is meant one or more carbocyclic ring systems of 4-, 5-, 6-, or 7-membered rings which includes fused ring systems of 9-11 atoms containing at least one and up to four heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide and homothiomorpholinyl S-oxide. The heterocycle groups herein are unsubstituted or, as specified, substituted in one or more substitutable positions with various groups. For example, such heterocycle groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$)alkyl or =O.

Structures were named using Name Pro IUPAC Naming Software, version 5.09, available from Advanced Chemical Development, Inc., 90 Adelaide Street West, Toronto, Ontario, M5H 3V9, Canada or using ChemDraw v. 6.02 or ChemDraw v. 8.03, both of which are available from Cambridgesoft at 100 Cambridge Park Drive, Cambridge, Mass. 02140 (www.cambridgesoft.com).

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The invention also encompasses prodrugs of the compounds of Formula I.

The invention also encompasses the acylated prodrugs of the compounds of Formula I. Those skilled in the art will recognize various synthetic methodologies, which may be employed to prepare non-toxic pharmaceutically acceptable addition salts and acylated prodrugs of the compounds encompassed by Formula I.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

The invention also encompasses the prodrugs of the compounds of Formula I. Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvates, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of the invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The anti-inflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

The disclosures in this document of all articles and references, including patents, are incorporated herein by reference in their entirety.

The invention is illustrated further by the following examples, which are not to be construed as limiting the invention in scope or spirit to the specific procedures described in them.

The starting materials and various intermediates may be obtained from commercial sources, prepared from commercially available compounds, or prepared using known synthetic methods.

General Synthetic Procedures

The compounds of the invention can be prepared using methods well known in the art of organic synthesis. Representative procedures for preparing compounds of the invention are outlined in the following schemes.

Compounds of the invention can be prepared by various methods known to those skilled in the art. For example, the compounds of the invention, as well as all intermediates, can be synthesized by known processes using either solution or solid phase techniques, as shown below.

Scheme 1:

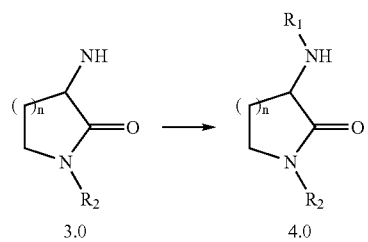

$R_1$, $R_2$, and n are as defined in the specification.

Using standard methods familiar to those skilled in the art, primary amine 3.0 is converted into secondary amine 4.0. Possible methods include, but are not limited to, reductive alkylations using a ketone or aldehyde, and a reducing agent, such as $NaCNBH_3$, $NaBH_4$, polystyrene bound borohydride, or $H_2$ and a transition metal catalyst, in a suitable solvent, such as methanol.

Scheme 2:
Compounds of Formula Ib

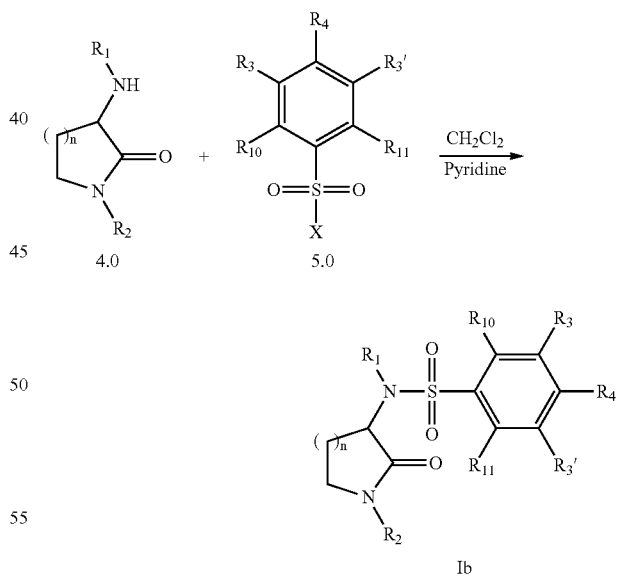

All of the variables are as defined in the specification.

Sulfonylation of secondary amines 4.0 with an appropriate sulfonylhalide 5.0 in a suitable solvent such as dichloromethane, chloroform, or tetrahydrofuran, in the presence of a base, such as pyridine, triethylamine, lutidine, or diisopropylethylamine, at a decreased temperature, affords compounds of formula Ib.

Scheme 3

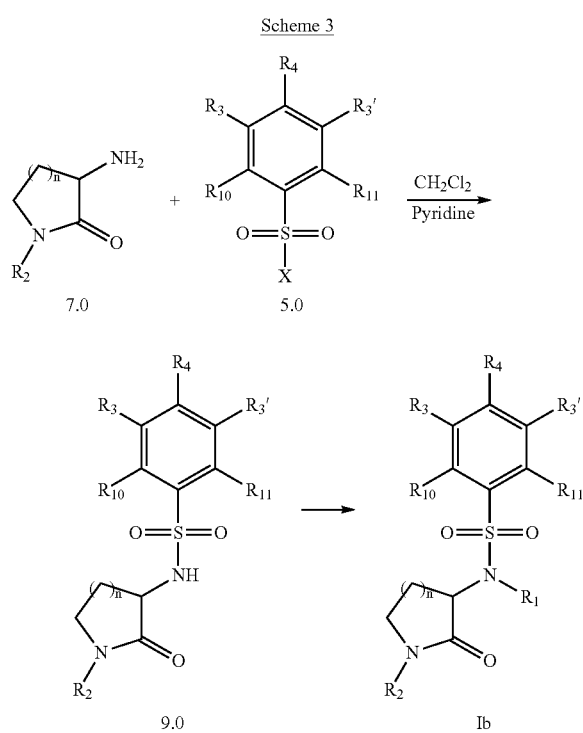

All of the variables are as defined in the specification.

One possible method for preparing the compounds of the invention is illustrated in scheme 3. Sulfonylation of primary amines 7.0 with an appropriate sulfonylhalide 5.0 in a suitable solvent such as dichloromethane, chloroform, tetrahydrofuran, in the presence of a base such as diisopropylethylamine or triethylamine at a decreased temperature generate sulfonamides 9.0. Sulfonamides 9.0 are further functionalized by treatment with an alkyl or arylalkyl halide via nucleophilic displacement, in a solvent such as DMF, dimethylacetamide, dioxane, tetrahydrofuran, with a base such as cesium carbonate, to afford compounds of formula Ib. Alternatively, sulfonamides 9.0 can be converted into compounds of formula Ib by reacting 9.0 with a primary or secondary alcohol via a Mitsunobu reaction.

Certain compounds of this invention are prepared from other compounds listed in this invention via well-known functional group transformations. Such transformations include ester hydrolysis, amide formation, reductive alkylation, with examples of such described in the preparations. Starting materials are prepared by known methods and are described in the examples below.

Compounds included in this invention are exemplified by the following examples, which should not be construed as limiting the scope of this disclosure. Analogous structures and alternative mechanistic pathways within the scope of the invention may be apparent to those skilled in the art.

Example 1

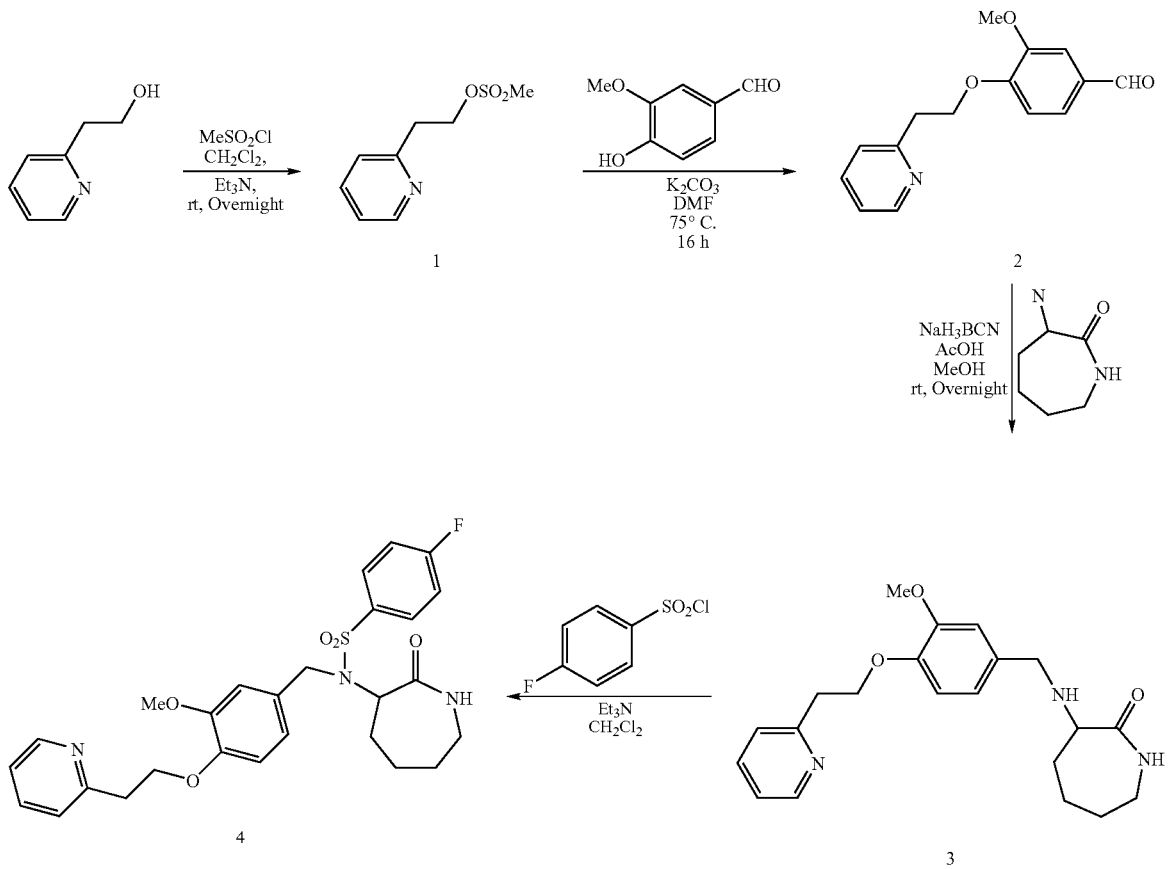

2-(2-Methanesulfonyl-ethyl)-pyridine (1)

To a 0.2 M solution of 2-(2-hydroxyethyl)pyridine (4.5 mmol) in methylene chloride is added triethylamine (24 mmol), followed by methanesulfonyl chloride (4.8 mmol.) The resulting mixture is stirred at room temperature overnight. The mixture is then poured into water and extracted with methylene chloride. The organic extracts are combined, washed with NaHCO$_3$ (sat), and then 1M aq. HCl. The acidic aqueous extracts are neutralized with NaHCO$_3$ (sat) and then extracted with methylene chloride. The organic extracts were combined, dried (MgSO$_4$), filtered, and concentrated to afford the desired product (1).

3-Methoxy-4-(2-pyridin-2-yl-ethyl)-benzaldehyde (2)

Vanillin (2.5 mmol) is added to mixture of K$_2$CO$_3$ (12.5 mmol) and 2-(2-Methanesulfonyl-ethyl)-pyridine (1) (2.5 mmol) in DMF (0.2 M), and the resulting reaction mixture is heated to 75° C. for 16 h. After cooling to approximately room temperature, water is added and the aqueous mixture is extracted 5 times with methylene chloride. The methylene chloride layers are combined and concentrated to afford a residue, which is recrystallized in diethyl ether.

3-[3-Methoxy-4-(2-pyridin-2-yl-ethoxy)-benzylamino]-azepan-2-one (3)

Acetic acid (1.8 mmol) is added to 3-Methoxy-4-(2-pyridin-2-yl-ethyl)-benzaldehyde (2) (0.45 mmol) and DL-α-amino-ε-caprolactam (0.45 mmol) in a minimal amount of methanol. The resulting reaction mixture is stirred for 3 hours, and then MeOH (0.2 M) is added, followed by NaH$_3$BCN (0.45 mmol), which is added in three portions over 19 hours. The product (3) is obtained by purification using reverse phase HPLC.

4-Fluoro-N-[3-methoxy-4-(2-pyridin-2-yl-ethoxy)-benzyl]-N-(2-oxo-azepan-3-yl)-benzenesulfonamide (4)

4-fluorobenzenesulfonyl chloride (0.22 mmol) is added to a room temperature solution of triethylamine (0.9 mmol) and 3-[3-Methoxy-4-(2-pyridin-2-yl-ethoxy)-benzylamino]-azepan-2-one (3) (0.22 mmol) in methylene chloride (0.2 M). After stirring for 48 hours, the reaction mixture is concentrated and the resulting residue is purified by reverse phase HPLC, to afford the desired product (4).

Example 2

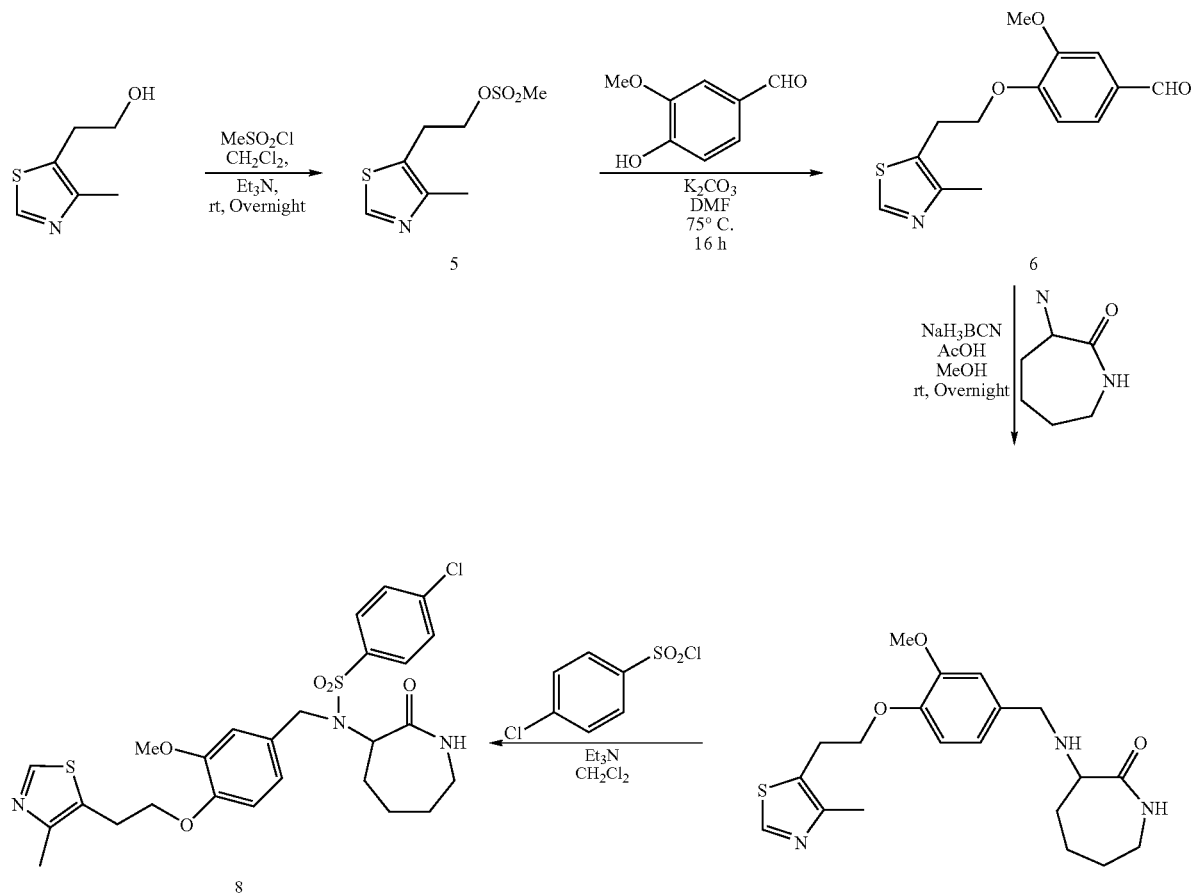

5-(2-Methanesulfonyl-ethyl)-4-methyl-thiazole (5)

Methanesulfonyl chloride (5.4 mmol) was added to a methylene chloride (0.2 M) solution of 5-(2-hydroxyethyl)-4-methyl-thiazole (4.5 mmol) and triethylamine (23 mmol), and stirred at room temperature overnight. The mixture was poured into water and extracted with methylene chloride. The organic extracts were washed with $NaHCO_3$ (sat), and the product was extracted with 1M aq. HCl. The aqueous extracts were neutralized with $NaHCO_3$ (sat) and then extracted with methylene chloride. The organic extracts were dried ($MgSO_4$) and filtered. Solvent removal afforded product (5).

3-Methoxy-4-[2-(4-methyl-thiazol-5-yl)-ethoxy]-benzaldehyde (6)

Vanillin (2.9 mmol) was added to mixture of $K_2CO_3$ (14.5 mmol) and 5-(2-Methanesulfonyl-ethyl)-4-methyl-thiazole (5) (2.9 mmol) in DMF (0.2 M), and heated to 75° C. for 16 h. After cooling, water was added and aqueous mixture extracted 5 times with methylene chloride. The methylene chloride layers were combined and concentrated to afford the product (6).

3-{3-Methoxy-4-[2-(4-methyl-thiazol-5-yl)-ethoxy]-benzylamino}-azepan-2-one (7)

Acetic acid (9.4 mmol) was added to 3-Methoxy-4-[2-(4-methyl-thiazol-5-yl)-ethoxy]-benzaldehyde (6) (2.3 mmol) and DL-α-amino-ε-caprolactam (2.3 mmol) in minimal amount of methanol and stirred for 2 h. MeOH (0.2 M) was added followed by $NaH_3BCN$ (2.3 mmol), and the reaction was stirred for 19 h. The product (7) was obtained by purification upon reverse phase HPLC.

4-Chloro-N-{3-methoxy-4-[2-(4-methyl-thiazol-5-yl)-ethoxy]-benzyl}-N-(2-oxo-azepan-3-yl)-benzenesulfonamide (8)

4-chlorobenzenesulfonylchloride (0.26 mmol) was added to a methylene chloride (0.2 M) solution of triethylamine (1.0 mmol) and 3-{3-Methoxy-4-[2-(4-methyl-thiazol-5-yl)-ethoxy]-benzylamino}-azepan-2-one (7) (0.26 mmol), and stirred at room temperature for 12 h. The product (8) was obtained by purification upon reverse phase HPLC.

In the following examples, MH+ refers to the mass as determined by LC/MS carried out on a ThermoHypersil-Keystone BDS Hypersil C18 column (50 mm×3 mm, 5 micron particle size). MNa+ is used to identify the product based on it sodium adduct. Elution conditions for LC/MS are as follows: Solvents: A. Water with 0.05% TFA (v/v); B. Acetonitrile with 0.05% TFA (v/v); Flow rate: 3 mL/min

| Gradient Method | |
|---|---|
| Time (min) | % B Conc |
| 0 | 5 |
| 0.25 | 5 |
| 2.75 | 95 |
| 3.5 | 95 |
| 3.6 | 5 |
| 4.0 | STOP |

In isolating the following examples, a Varian reverse-phase preparative HPLC, utilizing a Phenomenex Aqua $C_{18}$ column (60 mm×21.2 mm, 5 micron particle size) was used. Elution conditions for the HPLC are as follows: Solvents: A. Water with 0.1% TFA (v/v); B. Acetonitrile with 0.1% TFA (v/v); Flow rate: 25 mL/min.

| Gradient Method | |
|---|---|
| Time (min) | % B Conc |
| 0 | 5 |
| 0.75 | 5 |
| 9.5 | 100 |
| 10.5 | 100 |
| 11.5 | 5 |
| 12.0 | STOP |

Example 3

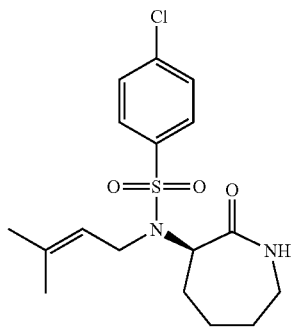

Step 1

4-chlorobenzenesulfonyl chloride (7.08 g; 30.54 mmol) was added to a 0° C. solution of D-α-amino-ε-caprolactam hydrochloride (5.0 g; 30.49 mmol) and triethylamine (25 ml; 244 mmol) in $CH_2Cl_2$ and was allowed to stir for 4 h at 0° C. An aqueous workup was performed, partitioning $CH_2Cl_2$ and water, followed by $CH_2Cl_2$ and 3N HCl. The organic layer was then dried with $MgSO_4$, filtered and concentrated. The sample was then dissolved in hot methanol (100 ml), followed by the addition of water (20 ml) and allowed to crystallize in a refrigerator over 48 h. The solution was then filtered and dried, isolating the desired product (5.42 g).

Step 2

The newly formed sulfonamide from Step 1 (60 mg, 0.2 mmol) was dissolved in DMF (1 ml) and added to a mixture of 4-bromo-2-methyl-2-butene (30 mg; 0.2 mmol) and cesium carbonate (130 mg; 0.4 mmol). The solution was sonicated and stirred for 39 h at 50° C. The crude reaction mixture was then placed on a Varian reverse-phase preparative HPLC to isolate the desired product.

Example 4

Synthesis of D-Boc-α-amino-ε-caprolactam

In a 1 L round bottom flask under a nitrogen atmosphere is placed 20 g (80 mmol) of N-α-Boc-D-lysine with 300 mL of DMF and a magnetic stir bar. 36 g of BOP is added to the room temperature slurry. The reaction is stirred for 15 minutes until clear. Then 36 g of $NaHCO_3$ and 100 mL of DMF are added. After 20 hours, the reaction mixture is concentrated under vacuum. The concentrated mixture is diluted with water and aqueous NaHCO₃ solution (1:1) and extracted three times with ethyl acetate. The combined organic extracts are washed with water, saturated aqueous NaHCO₃ solution, saturated aqueous NaCl solution, dried (Na₂SO₄), filtered and concentrated to afford a residue. The residue is triturated with ether (20 mL) and filtered. Washing the precipitate with hexanes led to another crop in the filtrate. A final crop is obtained by concentrating of the second filtrate and treatment with hexanes. Combining all crops affords the desired cyclized product. MS: 229 (M+H).

Procedure for Synthesis of D-α-amino-ε-caprolactam HCl

The D-Boc-α-amino-ε-caprolactam (12 g, 52 mmol) is mixed with 130 mL of dioxane to form a cloudy solution. 30 mL of 4N HCl in dioxane is added and gas evolution is noted. After 2 hours, HPLC-MS shows incomplete reaction. Methanol (20 mL) and an additional 20 mL of 4N HCl in dioxane solution are added and stirring continued overnight. The resulting solid was filtered and dried in a vacuum oven to yield 8.85 g of the desired product. Chiral HPLC analysis showed no racemization. MS: 129 (M+H).

Example 5

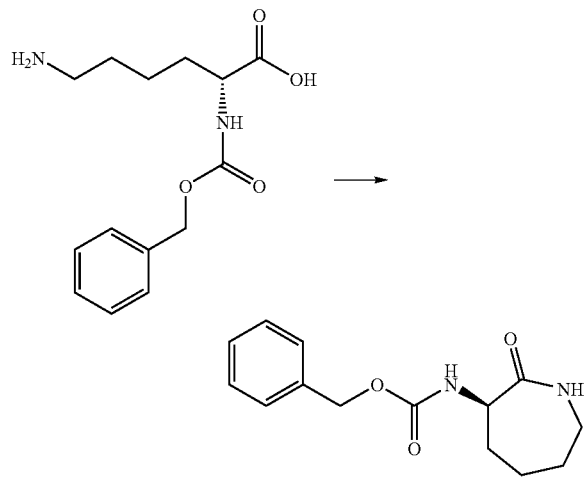

Step 1

D-Z-α-amino-ε-caprolactam.

A mixture of 5.0 grams of N-α-Z-D-lysine, 4.4 grams of HOBt, 5.5 mL of N-methylmorpholine, 200 mL of dichloromethane, and 200 mL of dimethylformamide are treated with 3.8 grams of EDC. After 18 hours the mixture is partitioned between ethyl acetate and distilled water. (The two phase mixture was filtered to remove some insoluble material prior to separating the phases.) The aqueous phase is washed with ethyl acetate, and the combined organic extracts are washed with aqueous potassium carbonate, aqueous sodium bisulfate, and finally with brine. The solution is dried over magnesium sulfate, filtered, and concentrated to afford 3.2 grams of a white solid, having m/z=285.1.

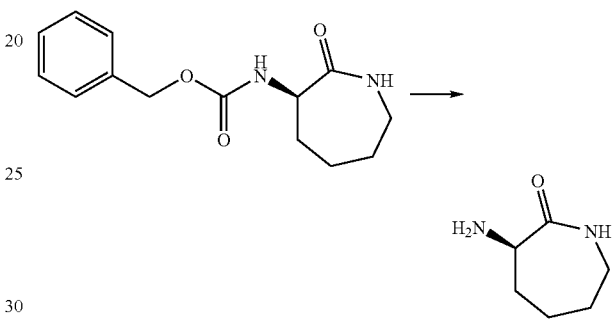

D-α-amino-ε-caprolactam. All of the product from Step 1 is dissolved in 65 mL of methanol and treated with 100 mg of 10% palladium on carbon. The mixture is agitated for 36 hours under 30 psi of hydrogen, and then filtered. Mass spectral analysis shows m/z=129.

D-α-Amino-δ-valerlactam and D-α-amino-γ-butyrlactam were made by the same procedure from N-α-Z-D-ornithine and N-α-Z-D-diaminobutyric acid respectively.

The following compounds are prepared essentially according to the methods and procedures described above. The mass spectra data in the following tables is experimentally derived and not calculated.

| Ex. No. | Name | M + H⁺ | M + Na⁺ |
|---|---|---|---|
| 1 | 4-Chloro-N-(4-hydroxy-3-methoxy-benzyl)-N-(2-oxo-azepan-3-yl)-benzenesulfonamide | 439.1 | |
| 2 | 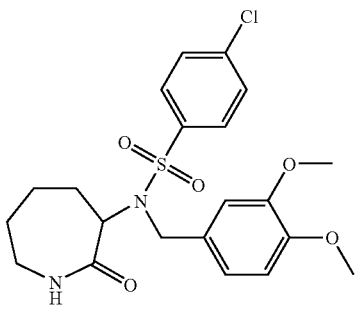 | | 475.1 |

-continued

| Ex. No. | Name | M + H+ | M + Na+ |
|---|---|---|---|
|  | 4-Chloro-N-(3,4-dimethoxy-benzyl)-N-(2-oxo-azepan-3-yl)-benzenesulfonamide | | |
| 3 | 4-Chloro-benzenesulfonic acid 4-{[(4-chloro-benzenesulfonyl)-(2-oxo-azepan-3-yl)-amino]-methyl-56 -2-methoxy-phenyl ester | 613.8 | |
| 4 | 4-chloro-N-(4-chlorobenzyl)-N-[(3R)-2-oxoazepan-3-yl]benzenesulfonamide | 427.0 | |
| 5 | 4-Butyl-N-(3,4-dimethoxy-benzyl)-N-(2-oxo-azepan-3-yl)-benzenesulfonamide | | 497.2 |
| 6 | N-(3,4-Dimethoxy-benzyl)-4-methoxy-N-(2-oxo-azepan-3-yl)-benzenesulfonamide | | 471.1 |
| 7 | 7-Chloro-benzo[1,2,5]oxadiazole-4-sulfonic acid (3,4-dimethoxy-benzyl)-(2-oxo-azepan-3-yl)-amide | | 517.0 |
| 8 | 4-Chloro-benzene-1,3-disulfonic acid 3-amide 1-[(3,4-dimethoxy-benzyl)-(2-oxo-azepan-3-yl)-amide] | | 554.1 |
| 9 | 4-Cyano-N-(3,4-dimethoxy-benzyl)-N-(2-oxo-azepan-3-yl)-benzenesulfonamide | | 466.1 |
| 10 | 4-Bromo-N-(3,4-dimethoxy-benzyl)-N-(2-oxo-azepan-3-yl)-benzenesulfonamide | | 519.0 |
| 11 | N-(3,4-Dimethoxy-benzyl)-N-(2-oxo-azepan-3-yl)-4-phenoxy-benzenesulfonamide | | 533.2 |
| 12 | 1-Oxa-2,3-diaza-cyclopenta[a]naphthalene-5-sulfonic acid (3,4-dimethoxy-benzyl)-(2-oxo-azepan-3-yl)-amide | | 533.2 |
| 13 | N-(3,4-Dimethoxy-benzyl)-3-methyl-N-(2-oxo-azepan-3-yl)-benzenesulfonamide | | 455.1 |
| 14 | 4-tert-Butyl-N-(3,4-dimethoxy-benzyl)-N-(2-oxo-azepan-3-yl)-benzenesulfonamide | | 497.1 |
| 15 | N-(3,4-Dimethoxy-benzyl)-4-iodo-N-(2-oxo-azepan-3-yl)-benzenesulfonamide | | 567.1 |
| 16 | N-(3,4-Dimethoxy-benzyl)-4-isocyanato-N-(2-oxo-azepan-3-yl)-benzenesulfonamide | | 460.1 |
| 17 | 3-Bromo-N-(3,4-dimethoxy-benzyl)-N-(2-oxo-azepan-3-yl)-benzenesulfonamide | | 520.0 |
| 18 | Naphthalanene-2-sulfonic acid (3,4-dimethoxy-benzyl)-(2-oxo-azepan-3-yl)-amide | | 491.1 |
| 19 | 3-Chloro-N-(3,4-dimethoxy-benzyl)-4-fluoro-N-(2-oxo-azepan-3-yl)-benzenesulfonamide | | 493.0 |
| 20 | N-(3,4-Dimethoxy-benzyl)-3-fluoro-4-methyl-N-(2-oxo-azepan-3-yl)-benzenesulfonamide | | 473.0 |
| 21 | 3,4-Dichloro-N-(3,4-dimethoxy-benzyl)-N-(2-oxo-azepan-3-yl)-benzenesulfonamide | | 509.0 |
| 22 | 3-Chloro-N-(3,4-dimethoxy-benzyl)-N-(2-oxo-azepan-3-yl)-benzenesulfonamide | | 475.1 |
| 23 | N-(3,4-Dimethoxy-benzyl)-N-(2-oxo-azepan-3-yl)-benzenesulfonamide | | 441.1 |
| 24 | 3,5-Dichloro-N-(3,4-ddimethoxy-benzyl)-N-(2-oxo-azepan-3-yl)-benzenesulfonamide | | 510.1 |
| 25 | N-(3,4-Dimethoxy-benzyl)-3,4-dimethoxy-N-(2-oxo-azepan-33-yl)-benzenesulfonamide | | 501.2 |
| 26 | N-(3,4-Dimethoxy-benzyl)-4-methyl-N-(2-oxo-azepan-3-yl)-benzenesulfonamide | | 455.1 |
| 27 | N-(3,4-Dimethoxy-benzyl)-4-methanesulfonyl-N-(2-oxo-azepan-3-yl)-benzenesulfonamide | | 519.2 |
| 28 | 3-{4-[(3,4-Dimethoxy-benzyl)-(2-oxo-azepan-3-yl)-sulfamoyl]-phenyl}-propionic acid methyl ester | | 527.1 |
| 29 | N-{4-[(3,4-Dimethoxy-benzyl)-(2-oxo-azepan-3-yl)-sulfamoyl]-phenyl}-acetamide | | 498.1 |
| 30 | 3-Chloro-N-(3,4-dimethoxy-benzyl)-4-methyl-N-(2-oxo-azepan-3-yl)-benzenesulfonamide | | 489.0 |
| 31 | N-(3,4-Dimethoxy-benzyl)-N-(2-oxo-azepan-3-yl)-4-trifluoromethoxy-benzenesulfonamide | | 525.1 |
| 32 | 4-Acetyl-N-(3,4-dimethoxy-benzyl)-N-(2-oxo-azepan-3-yl)-benzenesulfonamide | | 483.1 |

-continued

| Ex. No. | Name | M + H⁺ | M + Na⁺ |
|---|---|---|---|
| 33 | N-{2-Chloro-4-[(3,4-dimethoxy-benzyl)-(2-oxo-azepan-3-yl)-sulfamoyl]-phenyl}-acetamide | | 532.1 |
| 34 | N-(3,4-Dimethoxy-benzyl)-N-(2-oxo-azepan-3-yl)-3-trifluoromethyl-benzenesulfonamide | | 509.1 |
| 35 | 2-(2,2,2-Trifluoro-acetyl)-1,2,3,4-tetrahydro-issoquinoline-7-sulfonic acid (3,4-dimethoxy-benzyl)-(2-oxo-azepan-3-yl)amide | | 592.2 |
| 36 | 3-Cyano-N-(3,4-dimethoxy-benzyl)-N-(2-oxo-azepan-3-yl)-benzenesulfonamide | | 466.1 |
| 37 | N-(3,4-Dimethoxy-benzyl)-4-fluoro-N-(2-oxo-azepan-3-yl)-benzenesulfonamide | | 459.1 |
| 38 | N-(3,4-Dimethoxy-benzyl)-3,4-difluoro-N-(2-oxo-azepan-3-yl)-benzenesulfonamide | | 477.0 |
| 39 | N-(3,4-Dimethoxy-benzyl)-4-(1,1-dimethyl-propyl)-N-(2-oxo-azepan-3-yl)-benzenesulfonamide | | 511.2 |
| 40 | N-(3,4-Dimethoxy-benzyl)-4-issopropoxy-N-(2-oxo-azepan-3-yl)-benzenesulfonamide | | 499.1 |
| 41 | N-(3,4-Dimethoxy-benzyl)-N-(2-oxo-azepan-3-yl)-4-propyl-benzenesulfonamide | | 483.2 |
| 42 | N-(3,4-Dimethoxy-benzyl)-4-oxazol-5-yl-N-2-oxo-azepan-3-yl)-benzenesulfonamide | | 486.2 |
| 43 | N-(3,4-Dimethoxy-benzyl)-N-(2-oxo-azepan-3-yl)-4-pyrazol-1-yl-benzenesulfonamide | | 507.1 |
| 44 | 4-Bromo-N-(3,4-dimethoxy-benzyl)-3-fluoro-N-(2-oxo-azepan-3-yl)-benzenesulfonamide | | 538.1 |
| 45 | 4-Chloro-N-(3,4-dimethoxy-benzyl)-2,5-difluoro-N-(2-oxo-azepan-3-yl)-benzenesulfonamide | | 511.0 |
| 46 | N-(3,4-Dimethoxy-benzyl)-3,5-difluoro-N-(2-oxo-azepan-3-yl)-benzenesulfonamide | | 477.1 |
| 47 | Biphenyl-3-sulfonic acid (3,4-dimethoxy-benzyl)-(2-oxo-azepan-3-yl)-amide | | 517.1 |
| 48 | N-(3,4-Dimethoxy-benzyl)-2,3,4-trifluoro-N-(2-oxo-azepan-3-yl)-benzenesulfonamide | | 495.1 |
| 49 | N-(3,4-Dimethoxy-benzyl)-2,4,5-trifluoro-N-(2-oxo-azepan-3-yl)-benzenesulfonamide | | 495.1 |
| 50 | N-(3,4-Dimethoxy-benzyl)-2,3,4,5,6-pentafluoro-N-(2-oxo-azepan-3-yl)-benzenesulfonamide | | 531.0 |
| 51 | N-(3,4-Dimethoxy-benzyl)-4-isopropyl-N-(2-oxo-azepan-3-yl)-benzenesulfonamide | | 483.2 |
| 52 | 4-Chloro-N-cyclopropylmethyl-N-(2-oxo-azepan-3-yl)-beenzenesulfonamide | | 380 |
| 53 | N-But-2-enyl-4-chloro-N-(2-oxo-azepan-3-yl)-benzenesulfonamide | 358 | |
| 54 | 4-Chloro-N-(2-oxo-azepan-3-yl)-N-pentyl-benzenesulfonamide | 374.1 | |
| 55 | 4-Chloro-N-(2-ethyl-butyl)-N-(2-oxo-azepan-3-yl)-benzenesulfonamide | 388.1 | |
| 56 | 4-Chloro-N-hexyl-N-(2-oxo-azepan-3-yl)-benzenesulfonamide | 388.1 | |
| 57 | 4-Chloro-N-(3-methylsulfanyl-propyl)-N-(2-oxo-azepan-3-yl)-benzenesulfonamide | 392 | |
| 58 | 4-Chloro-N-heptyl-N-(2-oxo-azepan-3-yl)-benzenesulfonamide | 402.1 | |
| 59 | 4-Chloro-N-(2-oxo-azepan-3-yl)-N-(3-phenyl-allyl)-benzenesulfonamide | | 442 |
| 60 | 4-Chloro-N-nonyl-N-(2-oxo-azepan-3-yl)-benzenesulfonamide | 430.2 | |
| 61 | 6-[(4-Chloro-beenzenesulfonyl)-(2-oxo-azepan-3-yl)-amino]hexanoic acid methyl ester | 432.2 | |
| 62 | 4-Chloro-N-(2-methyl-3-phenyl-allyl)-N-(2-oxo-azepan-3-yl)-benzenesulfonamide | | 457 |
| 63 | N-(2-Benzyloxy-ethyl)-4-chloro-N-(2-oxo-azepan-3-yl)-benzenesulfonamide | 438.1 | |

-continued

| Ex. No. | Name | M + H+ | M + Na+ |
|---|---|---|---|
| 64 | N-(2-Bromo-3-phenyl-allyl)-4-chloro-N-(2-oxo-azepan-3-yl)-benzenesulfonamide | 498.9 | |
| 65 | 4-[(4-Chloro-benzenesulfonyl)-(2-oxo-azepan -3-yl)-amino]-3-methyl-but-2-enoic acid ethyl ester | 430.1 | |
| 66 | 4-Chloro-N-(2-ethyl-allyl)-N-(2-oxo-azepan-3-yl)-benzenesulfonamide | 372 | |
| 67 | 4-Chloro-N-(2,2-dimethyl-propyl)-N-(2-oxo-azepan-3-yl)-benzenesulfonamide | 374.1 | |
| 68 | 4-Chloro-N-isobutyl-N-(2-oxo-azepan-3-yl)-benzenesulfonamide | 359.8 | |
| 69 | methyl (2-{[(4-chlorophenyl)sulfonyl][(3R)-2-oxoazepan-3-yl]amino}ethyl)carbamate | | 427.1 |
| 70 | N-Butyl-4-chloro-N-(2-oxo-azepan-3-yl)-benzenesulfonamide | 360 | |
| 71 | 4-Chloro-N-(3-methyl-but-2-enyl)-N-(2-oxo-azepan-3-yl)-benzenesulfonamide | | 394.1 |
| 72 | 4-Chloro-N-(3-methyl-butyl)-N-(2-oxo-azepan-3-yl)-benzenesulfonamide | 374.1 | |
| 73 | 4-Chloro-N-(2-oxo-azepan-3-yl)-N-phenethyl-benzenesulfonamide | 408 | |
| 74 | N-(1,3-benzodioxol-5-ylmethyl)-4-chloro-N-[(3R)-2-oxoazepan-3-yl]benzenesulfonamide | 437.0 | |
| 75 | 4-Chloro-N-(3-fluoro-4-methoxybenzyl)-N-[(3R)-2-oxoazepan-3-yl]benzenesulfonamide | | 463.1 |
| 76 | 4-chloro-N-(3,4-dimethylbenzyl)-N-[(3R)-2-oxoazepan-3-yl]benzenesulfonamide | 421.0 | |
| 77 | 4-chloro-N-(2,3-dihydro-1,4-benzodioxin-6-ylmethyl)-N-[(3R)-2-oxoazepan-3-yl]benzenesulfonamide | | 473.0 |
| 78 | 4-chloro-N-(4-methoxybenzyl)-N-[(3R)-2-oxoazepan-3-yl]benzenesulfonamide | | 445.1 |
| 79 | 4-Chloro-N-naphthalen-2-ylmethyl-N-(2-oxo-azepan-3-yl)-benzenesulfonamide | 444 | |
| 80 | 4-Chloro-N-(3-iodo-benzyl)-N-(2-oxo-azepan-3-yl)-benzenesulfonamide | 520.1 | |
| 81 | 4-chloro-N-(cyclohexylmethyl)-N-[(3R)-2-oxoazepan-3-yl]benzenesulfonamide | 399.8 | |
| 82 | 4-chloro-N-[(3R)-2-oxoazepan-3-yl]-N-(4-phenoxybutyl)benzenesulfonamide | 451.8 | |
| 83 | N-[4-(benzyloxybutyl]-4-chloro-N-[(3R)-2-oxoazepan-3-yl]benzenesulfonamide | 465.8 | |
| 84 | 4-chloro-N-[(3R)-2-oxoazepan-3-yl]-N-(3-phenylpropyl)benzenesulfonamide | 421.1 | |
| 85 | 4-chloro-N-[(2E)-2-methyl-3-phenylprop-2-en-1-yl]-N-[(3R)-oxoazepan-3-yl]benzenesulfonamide | | 455.1 |
| 86 | 4-chloro-N-[(3R)-2-oxoazepan-3-yl]-N-[(2E)-3-phenylprop-2-en-1-yl]benzenesulfonamide | | 441.1 |
| 87 | 4-chloro-N-[(3R)-2-oxoazepan-3-yl]benzenesulfonamide | 303.0 | |
| 88 | | 421.8 | |
| | 4-chloro-N-[(3R)-2-oxoazepan-3-yl]-N-(3-phenylpropyl)benzenesulfonamide | | |
| 89 | N-[3-(benzyloxy)propyl]-4-chloro-N-[(3R)-2-oxoazepan-3-yl]benzenesulfonamide | 451.9 | |
| 90 | N-sec-Butyl-4-chloro-N-(2-oxo-azepan-3-yl)-benzenesulfonamide | 360 | |

| Ex. No. | Name | M + H+ | M + Na+ |
|---|---|---|---|
| 91 | tert-butyl ((1S)-1-benzyl-2-{[(4-chlorophenyl)sulfonyl][(3R)-2-oxoazepan-3-yl]amine}ethyl)carbamate | | 559.1 |
| 92 | tert-butyl ((1S)-2-{[(4-chlorophenyl)sulfonyl][(3R)-2-oxoazepan-3-yl]amino}-1-methylethyl)carbamate | | 483.2 |
| 93 | {2-[(4-Chloro-benzenesulfonyl)-(2-oxo-azepan-3-yl)-amino]-ethyl}-carbamic acid tert-butyl ester | | 469.1 |
| 94 | 4-Chloro-N-(2,2-diphenyl-ethyl)-N-(2-oxo-azepan-3-yl)-benzenesulfonamide | | 506 |
| 95 | N-[3-(4-tert-Butyl-phenyl)-2-methyl-propyl]-3-chloro-N-(2-oxo-azepan-3-yl)-benzenesulfonamide | 491.9 | |
| 96 | 4-Chloro-N-(2-methyl-4-phenyl-pentyl)-N-(2-oxo-azepan-3-yl)-benzenesulfonamide | 463.8 | |
| 97 | 4-Chloro-N-[3-(4-methoxy-phenyl)-allyl]-N-(2-oxo-azepan-3-yl)-benzenesulfonamide | | 472 |
| 98 | 4-chloro-N-(3-methylbut-2-en-1-yl)-N-[(3R)-2-oxoazepan-3-yl]benzenesulfonamide | | 393.8 |
| 99 | 4-chloro-N-[(3R)-2-oxoazepan-3-yl]-N-prop-2-yl-1-ylbenzenesulfonamide | 341.8 | |
| 100 | 4-chloro-N-isobutyl-N-[(3R)-2-oxoazepan-3-yl]benzenesulfonamide | 359.8 | |
| 101 | 4-chloro-N-[2-(1,3-dioxo-2,3-dihydro-1H-inden-2-yl)ethyl]-N-[(3R)-2-oxoazepan-3-yl]benzenesulfonamide | 476.9 | |
| 102 | 4-chloro-N-(8-hydroxyoxtyl)-N-[(3R)-2-oxoazepan-3-yl]benzenesulfonamide | 431.9 | |
| 103 | 4-chloro-N-[3-(1,3-dioxo-2,3-dihydro-1H-inden-2-yl)propyl]-N-[(3R)-2-oxoazepan-3-yl]benzenesulfonamide | 490.9 | |
| 104 | 4-chloro-N-[(3R)-2-oxoazepan-3-yl]-N-(tetrahydro-2H-pyran-2-ylmethyl)benzenesulfonamide | 401.8 | |
| 105 | 4-chloro-N-decyl-N-[(3R)-2-oxoazepan-3-yl]benzenesulfonamide | 443.9 | |
| 106 | 4-chloro-N-(1,3-dioxolan-2-ylmethyl)-N-[(3R)-2-oxoazepan-3-yl]benzenesulfonamide | 389.6 | |
| 107 | N2-[(4-chlorophenyl)sulfonyl]-N2-[(3R)-2-oxoazepan-3-yl]glycinamide | 360.7 | |
| 108 | 4-chloro-N-[4-(1,3-dioxo-2,3-dihydro-1H-inden-2-yl)butyl]-N-[(3R)-2-oxoazepan-3-yl]benzenesulfonamide | 504.9 | |
| 109 | 4-chloro-N-(6-methylheptyl)-N-[(3R)-2-oxoazepan-3-yl]benzenesulfonamide | 415.9 | |
| 110 | N-butyl-4-chloro-N-[(3R)-2-oxoazepan-3-yl]benzenesulfonamide | 359.8 | |
| 111 | 4-chloro-N-[3-(4-methoxyphenyl)propyl]-N-[(3R)-2-oxoazepan-3-yl]benzenesulfonamide | 451.9 | |
| 112 | ethyl 6-{[(4-chlorophenyl)sulfonyl][(3R)-2-oxoazepan-3-yl]amino}hexanoate | 445.8 | |
| 113 | 4-Chloro-N-{3-methoxy-4-[2-(4-methyl-thiazol-5-yl)-ethoxy]-benzyl}-N-(2-oxo-azepan-3-yl)-benzene sulfonamide | 565.6 | |
| 114 | 4-Fluoro-N-[3-methoxy-4-(2-pyridin-2-yl-ethoxy)-beenzyl]-N-(2-oxo-azepan-3-yl)-benzenesulfonamide | 528.6 | |
| 115 | N-[3-Methoxy-4-(2-pyridin-2-yl-ethoxy)-benzyl]-4-methyl-N-(2-oxo-azepan-3-yl)-benzenesulfonamide | 524.6 | |
| 116 | 3,4-Difluoro-N-{3-methoxy-4-[2-(4-methyl-thiazol-5-yl)-ethoxy]-benzyl}-N-(2-oxo-azepan-3-yl)-benzenesulfonamide | 566.6 | |
| 117 | N-{3-Methoxy-4-[2-(4-methyl-thiazol-5-yl)-ethoxy]-benzyl}-N-(2-oxo-azepan-3-yl)-4-trifluoromethyl-benzenesulfonamide | 598.6 | |
| 118 | 3-Fluoro-N-{3-methoxy-4-[2-(4-methyl-thiazol-5-yl)-ethoxy]-benzyl}-N-(2-oxo-azepan-3-yl)-benzenesulfonamide | 548.6 | |
| 119 | 4-Fluoro-N-{3-methoxy-4-[2-(4-methyl-thiazol-5-yl)-ethoxy]-benzyl}-N-(2-oxo-azepan-3-yl)-benzenesulfonamide | 548.5 | |

-continued

| Ex. No. | Name | M + H+ | M + Na+ |
|---|---|---|---|
| 120 | 4-chloro-N-{3-methoxy-4-[2-(4-methyl-1,3-thiazol-5-yl)ethoxy]benzyl}-N-[(3R)-2-oxoazepan-3-yl]benzenesulfonamide | 565.6 | |
| 121 | N-Benzyl-4-chloro-N-(2-oxo-azepan-3-yl)-benzenesulfonamide | | 415.2 |
| 122 | 4-Chloro-N-(3,4-dimethoxy-benzyl)-N-(2-oxo-azepan-3-yl)-benzenesulfonamide | | 475.1 |
| 123 | 4-chloro-N-[(3R)-2-oxopyrrolidin-3-yl]-N-(3-phenylpropyl)benzenesulfonamide | 393 | |
| 124 | 4-chloro-N-[(2E)-2-methyl-3-phenylprop-2-en-1-yl]-N-[(3R)-2-oxopyrrolidin-3-yl]benzenesulfonamide | | 428 |
| 125 | 4-chloro-N-dodecyl-N-[(3R)-2-oxoazepan-3-yl]benzenesulfonamide | 471.9 | |
| 126 | 4-chloro-N-[(3R)-2-oxoazepan-3-yl]-N-(2-phenylethyl)benzenesulfonamide | 407.8 | |
| 127 | ethyl 5-{[(4-chlorophenyl)sulfonyl][(3R)-2-oxoazepan-3-yl]amino}pentanoate | 431.8 | |
| 128 | 4-chloro-N-(4-methylpeentyl)-N-[(3R)-2-oxoazepan-3-yl]benzenesulfonamide | 387.8 | |
| 129 | 4-chloro-N-(2-methoxyethyl)-N-[(3R)-2-oxoazepan-3-yl]benzenesulfonamide | 361.8 | |
| 130 | ethyl 4-{[(4-chlorophenyl)sulfonyl][(3R)-2-oxoazepan-3-yl]amino}butanoate | 417.8 | |
| 131 | 4-chloro-N-(6,7-dihydroxy-3,7-dimethyloctyl)-N-[(3R)-2-oxoazepan-3-yl]benzenesulfonamide | 475.6 | |
| 132 | 4-chloro-N-((S)-3,7-dimethyloct-6-enyl)-N-((R)-2-oxoazepan-3-yl)benzenesulfonamide | 441.8 | |
| 133 | N-but-3-en-1-yl-4-chloro-N-[(3R)-2-oxoazepan-3-yl]benzenesulfonamide | 357.7 | |
| 134 | (R)-3-(4-chloro-N-(2-oxoazepan-3-yl)phenylsulfonamido)propanoic acid | 375.8 | |
| 135 | 4-chloro-N-[(3R)-2-oxoazepan-3-yl]-N-[(2E,6E)-3,7,11-trimethyldodeca-2,6,10-trien-1-yl]benzenesulfonamide | | 530.1 |
| 136 | N-benzyl-4-chloro-N-[(3R)-2-oxoazepan-3-yl]benzenesulfonamide | | 415.2 |
| 137 | 44-chlorro-N-(3,4-dimethoxybenzyl)-N-[(3R)-2-oxoazepan-3-yl]benzenesulfonamide | | 475.1 |
| 138 | 4-Chloro-N-(2-oxo-azepan-3-yl)-N-(3-phenyl-propyl)-benzenesulfonamide | 422.2 | |
| 139 | 4-chloro-N-[(3R)-2-oxopiperidin-3-yl]-N-(3-phenylpropyl)-benzenesulfonamide | 428 | |
| 140 | 4-chloro-N-[(2E)-2-methyl-3-phenylprop-2-en-1-yl]-N-[(3R)-2-oxopiperidin-3-yl]benzenesulfonamide | 416 | |
| 141 | 4-chloro-N-(3,4-dimethoxybenzyl)-N-[(3R)-2-oxo-piperidin-3-yl]benzenesulfonamide | | 428 |
| 142 | N-(4-bromobenzyl)-4-chloro-N-[(3R)-2-oxopiperidin-3-yl]benzenesulfonamide | | 432 |
| 143 | 4-chloro-N-[(3R)-2-oxopiperidin-3-yl]-N-[(2E)-3-phenylprop-2-en-1-yl]benzenesulfonamide | | 462 |
| 144 | 4-chloro-N-(4-methoxybenzyl)-N-[(3R)-2-oxopiepridin-3-yl]benzenesulfonamide | | 459 |

-continued

| Ex. No. | Name | M + H⁺ | M + Na⁺ |
|---|---|---|---|
| 145 | 4-chloro-N-(3-fluoro-4-methoxybenzyl)-N-[(3R)-2-oxopiperidin-3-yl]benzenesulfonamide | 408 | |
| 146 | 4-chloro-N-(2,4-difluorobenzyl)-N-[(3R)-2-oxopiperidin-3-yl]benzenesulfonamide | | 442 |
| 147 | 4-chloro-N-(3-fluoro-4-methoxybenzyl)-N-[(3R)-2-oxopyrrolidin-3-yl]benzenesulfonamide | | 436 |
| 148 | 4-chloro-N-(2,4-difluorobenzyl)-N-[(3R)-2-oxopyrrolidin-3-yl]benzenesulfonamide | 401 | |
| 149 | 4-chloro-N-[(3R)-2-oxopyrrolidin-3-yl]-[(2E)-3-phenylprop-2-en-1-yl]benzenesulfonamide | | 414 |
| 150 | 4-chloro-N-(4-methoxybenzyl)-N-[(3R)-2-oxopyrrolidin-3-yl]benzenesulfonamide | | 418 |
| 151 | 4-chloro-N-(3,4-dimethoxybenzyl)-N-[(3R)-2-oxopyrrolidin-3-yl]benzenesulfonamide | | 448 |
| 152 | N-(4-bromobenzyl)-4-chloro-N-[(3R)-2-oxopyrrolidin-3-yl]benzenesulfonamide | 444 | |
| 153 | 4-Chloro-N-(3,4-dichloro-benzyl)-N-(2-oxo-azepan-3-yl)-benzenesulfonamide | 462.8 | |
| 154 | 4-Chloro-(6-methoxy-naphthalen-2-ylmethyl)-N-(2-oxo-azepan-3-yl)-benzenesulfonamide | | 496.1 |
| 155 | 4-Chloro-N-(2-methoxy-benzyl)-N-(2-oxo-azepan-3-yl)-benzenesulfonamide | 423.7 | |
| 156 | 4-Chloro-N-(3-methoxy-benzyl)-N-(2-oxo-azepan-3-yl)-benzenesulfonamide | 423.8 | |
| 157 | 4-Chloro-N-94methoxy-benzyl)-N-(2-oxo-azepan-3-yl)-benzenesulfonamide | 423.5 | |
| 158 | 4-Chloro-N-(2-oxo-azepan-3-yl)-N-(3-trifluoromethyl-benzyl)-benzenesulfonamide | 461.8 | |
| 159 | 4-Chloro-N-(4-isopropoxy)-N-(2-oxo-azepan-3-yl)-benzenesulfonamide | 451.3 | |
| 160 | N-(5-Bromo-thiophen-2-ylmethyl)-4-chloro-N-(2-oxo-azepan-3-yl)-benzenesulfonamide | 478.4 | |
| 161 | 4-Chloro-N-(2-oxo-azepan-3-yl)-N-pyridin-3-ylmethyl-benzenesulfonamide | 395 | |
| 162 | 4-Chloro-N-(2-oxo-azepan-3-yl)-N-pyridin-2-ylmethyl-benzenesulfonamide | 394.8 | |
| 163 | 4-Chloro-N-(2-oxo-azepan-3-yl)-N-(4-trifluoromethyl-benzyl)-benzenesulfonamide | 461.8 | |
| 164 | 4-Chloro-N-(5,7-dimethyl-4-oxo-4H-chromen-3-ylmethyl)-N-(2-oxo-azepan-3-yl)-benzenesulfonamide | 490.2 | |
| 165 | 4-Chloro-N-(4-chloro-6-fluoro-2H-chromen-3-ylmethyl)-N-(2-oxo-azepan-3-yl)-benzenesulfonamide | | 521.9 |
| 166 | 4-Chloro-N-[5-(2,4-difluoro-phenyl)-furan-2-ylmethyl]-N-(2-oxo-azepan-3-yl)-benzenesulfonamide | | 516.9 |
| 167 | 4-Chloro-N-(5-chloro-1,3-dimethyl-1H-pyrazol-4-ylmethyl)-N-(2-oxo-azepan-3-yl)-benzenesulfonamide | 446.7 | |
| 168 | 4-Chloro-N-[5-(2-methyl-5-trifluoromethyl-2H-pyrazol-3-yl)-thiophen-2-ylmethyl]-N-(2-oxo-azepan-3-yl)-benzenesulfonamide | | 569.8 |
| 169 | N-(3-Benzyloxy-benzyl)-4-chloro-N-(2-oxo-azepan-3-yl)-benzenesulfonamide | 499.8 | |
| 170 | 4-Chloro-N-(2-oxo-azepan-3-yl)-N-(3-phenoxy-benzyl)-benzenesulfonamide | 485.8 | |
| 171 | 4-Chloro-N-(2-oxo-azepan-3-yl)-N-(4-phenoxy-benzyl)-benzenesulfonamide | | 508.1 |
| 172 | 4-{[(4-Chloro-benzenesulfonyl)-(2-oxo-azepan-3-yl)-amino]-methyl}-benzoic acid methyl ester | 451.8 | |
| 173 | N-(4-Bromo-benzyl)-4-chloro-N-(2-oxo-azepan-3-yl)-benzenesulfonamide | 472.7 | |
| 174 | 4-Chloro-N-(3,5-dichloro-benzyl)-N-(2-oxo-azepan-3-yl)-benzenesulfonamide | 463 | |

-continued

| Ex. No. | Name | M + H⁺ | M + Na⁺ |
|---|---|---|---|
| 175 | N-[4-(4-tert-Butyl-thiazol-2-yl)-benzyl]-4-chlorro-N-(2-oxo-azepan-3-yl)-benzenesulfonamide | 532.7 | |
| 176 | 4-Chloro-N-(1-methyl-1H-pyrazol-2-ylmethyl)-N-(2-oxo-azepan-3-yl)-benzenesulfonamide | | 419 |
| 177 | 4-Chloro-N-(2-oxo-azepan-3-yl)-N-(2-trifluoromethyl-benzyl)-benzenesulfonamide | 462.1 | |
| 178 | 4-Chloro-N-(2,3-dihydro-benzo[1,4]dioxin-6-ylmethyl)-N-(2-oxo-azepan-3-yl)-benzenesulfonamide | | 474 |
| 179 | 4-Chloro-N-(2-meethoxy-naphthalen-1-ylmethyl)-N-(2-oxo-azepan-3-yl)-benzenesulfonamide | | 496 |
| 180 | 4-Chloro-N-(4-isobutyl-benzyl)-N-(2-oxo-azepan-3-yl)-benzenesulfonamide | 449.7 | |
| 181 | 4-Chloro-N-(2,4-dimethoxy-benzyl)-N-(2-oxo-azepan-3-yl)-benzenesulfonamide | | 476.2 |
| 182 | N-(4-{[(4-Chloro-benzenesulfonyl)-(2-oxo-azepan-3-yl)-amino]-methyl}-phenyl)-acetamide | | 472.7 |
| 183 | 4-Chloro-N-(3-chloro-4-methoxy-benzyl)-N-(2-oxo-azepan-3-yl)-benzenesulfonamide | | 480 |
| 184 | N-{4-[Bis(2-chloro-ethyl)-amino]-benzyl}-4-chloro-N-(2-oxo-azepan-3-yl)-benzenesulfonamide | 534.1 | |
| 185 | 3-{[(4-Chloro-benzenesulfonyl)-(2-oxo-azepan-3-yl)-amino]-methyl}-benzoic acid methyl ester | 451.7 | |
| 186 | 4-Chloro-N-(2-morpholin-4-yl-benzyl)-N-(2-oxo-azepan-3-yl)-benzenesulfonamide | 478.9 | |
| 187 | 4-Chloro-N-(4,6-dichloro-2H-chromen-3-ylmethyl)-N-(2-oxo-azepan-3-yl)-benzenesulfonamide | | 538.9 |
| 188 | 4-Chloro-N-(2-oxxo-azepan-3-yl)-N-thiophen-2-ylmethyl-benzenesulfonamide | 399.6 | |
| 189 | 4-Chloro-N-(2,6-dichloro-benzyl)-N-(2-oxo-azepan-3-yl)-benzenesulfonamide | 463.7 | |
| 190 | 4-Chloro-N-(2-oxoazepan-3-yl)-N-thiophen-3-ylmethyl-benzenesulfonamide | 399.7 | |
| 191 | N-(3-Bromo-4-fluoro-benzyl)-4-chloro-N-(2-oxo-azepan-3-yl)-benzenesulfonamide | 490.8 | |
| 192 | N-(5-Bromo-2-fluoro-benzyl)-4-chloro-N-(2-oxo-azepan-3-yl)-benzenesulfonamide | 490.7 | |
| 193 | 4-Chloro-N-(2-oxo-azepan-3-yl)-N-thiazol-2-ylmethyl-benzenesulfonamide | 401 | |
| 194 | 4-Chloro-N-(2'-meethyl-biphenyl-4-ylmethyl)-N-(2-oxo-azepan-3-yl)-benzenesulfonamide | 483.8 | |
| 195 | 4-Chloro-N-(4-iodo-benzyl)-N-(2-oxo-azepan-3-yl)-benzenesulfonamide | 519.7 | |
| 196 | N-(3-Bromo-benzyl)-4-chloro-N-(2-oxo-azepan-3-yl)-benzenesulfonamide | 472.7 | |
| 197 | 4-Chloro-N-(2,6-dimethoxy-benzyl)-N-(2-oxo-azepan-3-yl)-benzenesulfonamide | 453.5 | |
| 198 | 4-Chloro-N-(2,3-dichloro-benzyl)-N-(2-oxo-azepan-3-yl)-benzenesulfonamide | 463.1 | |
| 199 | N-Biphenyl-4-ylmethyl-4-chloro-N-(2-oxo-azepan-3-yl)-benzenesulfonamide | 470.5 | |
| 200 | N-(4-tert-Butyl-benzyl)-4-chloro-N-(2-oxo-azepan-3-yl)-benzenesulfonamide | 449.7 | |
| 201 | N-(4-Benzyloxy-benzyl)-4-chloro-N-(2-oxo-azepan-3-yl)-benzenesulfonamide | | 522.3 |
| 202 | 4-Chloro-N-(2-oxo-azepan-3-yl)-N-[1,2,3]thiadiazol-4-ylmethyl-benzenesulfonamide | 402 | |
| 203 | 4-Chloro-N-(1-methyl-1H-indol-3-ylmethyl)-N-(2-oxo-azepan-3-yl)-benzenesulfonamide | | 469 |
| 204 | N-(1-Benzyl-1H-indol-3-ylmethyl)-4-chloro-N-(2-oxo-azepan-3-yl)-benzenesulfonamide | | 544.9 |
| 205 | 4-Chloro-N-(2-methyl-beenzyl)-N-(2-oxo-azepan-3-yl)-benzenesulfonamide | 407.8 | |

-continued

| Ex. No. | Name | M + H+ | M + Na+ |
|---|---|---|---|
| 206 | N-(1-Benzenesulfonyl-1H-pyrrol-2-ylmethyl)-4-chloro-N-(2-oxo-azepan-3-yl)-benzenesulfonamide | | 545.1 |
| 207 | 4-Chloro-N-(2-oxo-azepan-3-yl)-N-(1-phenyl-1H-[1,2,3]triazol-4-ylmethyl)-benzenesulfonamide | 460.8 | |
| 208 | 4-Chloro-N-(5-ethyl-furan-2-ylmethyl)-N-(2-oxo-azepan-3-yl)-benzenesulfonamide | | 433.9 |
| 209 | 4-Chloro-N-(2,5-dimethyl-2H-pyrazol-3-ylmethyl)-N-(2-oxo-azepan-3-yl)-benzenesulfonamide | 411.8 | |
| 210 | 4-Chloro-N-(4,5-dimethyl-furan-2-ylmethyl)-N-(2-oxo-azepan-3-yl)-benzenesulfonamide | | 433.8 |
| 211 | 4-Chloro-N-(5-cyano-6-methylsulfanyl-pyridin-2-ylmethyl)-N-(2-oxo-azepan-3-yl)-benzenesulfonamide | 465.8 | |
| 212 | 4-Chloro-N-(4-methyl-benzyl)-N-(2-oxo-azepan-3-yl)-benzenesulfonamide | 407.9 | |
| 213 | 5-{[(4-Chloro-benzenesulfonyl)-(2-oxo-azepan-3-yl)-amino]-methyl}-1-methyl-1H-pyrrole-2-carboxylic acid methyl ester | | 475.9 |
| 214 | N-(2-Bromo-benzyl)-4-chloro-N-(2-oxo-azepan-3-yl)-benzenesulfonamide | 472.8 | |
| 215 | 4-Chloro-N-(3-methyl-benzo[b]thiophen-2-ylmethyl)-N-(2-oxo-azepan-3-yl)-benzenesulfonamide | 463.3 | |
| 216 | 4-Chloro-N-(3-methyl-benzyl)-N-(2-oxo-azepan-3-yl)-benzenesulfonamide | 407.8 | |
| 217 | 4-chloro-N-(2,4-difluorobenzyl)-N-[(3R)-2-oxoazepan-3-yl]benzenesulfonamide | 429.8 | |
| 218 | N-(biphenbyl-2-ylmethyl)-4-chloro-N-[(3R)-2-oxoazepan-3-yl]benzenesulfonamide | 469.7 | |
| 219 | 4-chloro-N-(3-iodobenzyl)-N-[(3R)-2-oxoazepan-3-yl]benzenesulfonamide | 519.8 | |
| 220 | 4-chloro-N-[3-(4-fluorophenoxy)benzyl]-N[(3R)-2-oxoazepan-3-yl]benzenesulfonamide | 503.8 | |
| 221 | 4-chloro-N-(3,5-difluorobenzyl)-N-[(3R)-2-oxoazepan-3-yl]benzenesulfonamide | 429.8 | |
| 222 | 4-chloro-N-(3,5-dimethoxybenzyl)-N-[(3R)-2-oxoazepan-3-yl]benzenesulfonamide | 453.7 | |
| 223 | 4-chloro-N-(2-cyanobenzyl)-N-[(3R)-2-oxoazepan-3-yl]benzenesulfonamide | | 440.9 |
| 224 | 4-chloro-N-(3,4-difluorobenzyl)-N-[(3R)-2-oxoazepan-33-yl]benzenesulfonamide | 429.9 | |
| 225 | 44-chloro-N-[(3R)-2-oxoazepan-3-yl]-N-{2-[(phenylsulfonyl)methyl]benzyl}benzenesulfonamide | 547.7 | |
| 226 | 4-chloro-N-[(3R)-2-oxoazepan-3-yl]-N-[4-(trifluoromethoxy)benzyl]benzenesulfonamide | 477.7 | |
| 227 | 4-chloro-N-(2-naphthylmethyl)-N-[(3R)-2-oxoazepan-3-yl]benzenesulfonamide | 443.7 | |
| 228 | N-Biphenyl-2-ylmethyl-4-chloro-N-(2-oxo-azepan-3-yl)-benzenesulfonamide | 469.7 | |
| 229 | 4-chloro-N-(3-chlorobenzyl)-N-[(3R)-2-oxoazepan-3-yl]benzenesulfonamide | 427.8 | |
| 230 | 4-chloro-N-(3-cyanobenzyl)-N-[(3R)-2-oxoazepan-3-yl]benzenesulfonamide | 418.8 | |
| 231 | 4-chloro-N-[(3R)-2-oxoazepan-3-yl]-N-[3-(trifluoromethoxy)benzyl]benzenesulfonamide | 477.8 | |
| 232 | 4-chloro-N-(4-fluorobenzyl)-N-[(3R)-2-oxoazepan-3-yl]benzenesulfonamide | 411.7 | |
| 233 | 4-chloro-N-(2-chlorobenzyl)-N-[(3R)-2-oxoazepan-3-yl]benzenesulfonamide | 427.8 | |
| 234 | 4-chloro-N-[(2E)-3,7-dimethylocta-2,6-dien-1-yl]-N-[(3R)-oxoazepan-3-yl]benzenesulfonamide | | 462 |
| 235 | 4-Chloro-N-furan-2-ylmethyl-N-(2-oxo-azepan-3-yl)-benzenesulfonamide | 384.1 | |
| 236 | 4-Chloro-N-furan-3-ylmethyl-N-(2-oxo-azepan-3-yl)-benzenesulfonamide | 384 | |
| 237 | 4-Chloro-N-(4-cyano-benzyl)-N-(2-oxo-azepan-3-yl)-benzenesulfonamide | 419.1 | |

-continued

| Ex. No. | Name | M + H⁺ | M + Na⁺ |
|---|---|---|---|
| 238 | 4-Chloro-N-(3,4-dimethyl-benzyl)-N-(2-oxo-azepan-3-yl)-benzenesulfonamide | 422.1 | |
| 239 | 4-Chloro-N-(2,5-dimethyl-benzyl)-N-(2-oxo-azepan-3-yl)-benzenesulfonamide | 422.1 | |
| 240 | 4-Chloro-N-(1-dimethylamino-1H-pyrrol-2-ylmethyl)-N-(2-oxo-azepan-3-yl)-benzenesulfonamide | | 448.1 |
| 241 | 4-Chloro-N-(4-chloro-1-methyl-1H-pyrazol-3-ylmethyl)-N-(2-oxo-azepan-3-yl)-benzenesulfonamide | 432 | |
| 242 | N-Benzofuran-2-ylmethyl-4-chloro-N-(2-oxo-azepan-3-yl)-benzenesulfonamide | 435.2 | |
| 243 | 4-Chloro-N-(5-chloro-thiophen-2-ylmethyl)-N-(2-oxo-azepan-3-yl)-benzenesulfonamide | 434 | |
| 244 | 4-Chloro-N-(2-oxo-azepan-3-yl)-N-(2,4,5-trimethyl-benzyl)-benzenesulfonamide | | 457.1 |
| 245 | 4-Chloro-N-(4-isopropyl-benzyl)-N-(2-oxo-azepan-3-yl)-benzenesulfonamide | | 457.9 |
| 246 | 4-Chloro-N-(2-oxo-azepan-3-yl)-N-(2,4,6-trimethyl-benzyl)-benzenesulfonamide | | 458.2 |
| 247 | 4-Chloro-N-(3-cyano-4-fluoro-benzyl)-N-(2-oxo-azepan-3-yl)-benzenesulfonamide | | 459.1 |
| 248 | 4-Chloro-N-(4-dimethylamino-benzyl)-N-(2-oxo-azepan-3-yl)-benzenesulfonamide | 437.1 | |
| 249 | N-Benzo[1,3]dioxol-5-ylmethyl-4-chloro-N-(2-oxo-azepan-3-yl)-benzenesulfonamide | | 460.1 |
| 250 | 4-Chloro-N-(4-ethoxy-benzyl)-N-(2-oxo-azepan-3-yl)-benzenesulfonamide | | 460.1 |
| 251 | 4-Chloro-N-(2-ethoxy-benzyl)-N-(2-oxo-azepan-3-yl)-benzenesulfonamide | | 460.1 |
| 252 | 4-Chloro-N-(4-methoxy-2-methyl-benzyl)-N-(2-oxo-azepan-3-yl)-benzenesulfonamide | | 460 |
| 253 | 4-Chloro-N-(3-fluoro-4-methoxy-benzyl(-N-(2-oxo-azepan-3-yl)-benzenesulfonamide | | 464.1 |
| 254 | 4-Chloro-N-naphthalen-1-ylmethyl-N-(2-oxo-azepan-3-yl)-benzenesulfonamide | 444.1 | |
| 255 | 4-Chloro-N-(2-oxo-azepan-3-yl)-N-quinolin-2-ylmethyl-benzenesulfonamide | 445.1 | |
| 256 | 4-Chloro-N-(2-oxo-azepan-3-yl)-N-quinolin-3-ylmethyl-benzenesulfonamide | 445.1 | |
| 257 | 4-Chloro-N-(2-oxo-azepan-3-yl)-N-(4-oxo-4H-chromen-3-ylmethyl)-benzenesulfonamide | 462 | |
| 258 | N-(4-Bromo-thiophen-2-ylmethyl)-4-chloro-N-(2-oxo-azepan-3-yl)-benzenesulfonamide | 478.9 | |
| 259 | 4-Chloro-N-(2-oxo-azepan-3-yl)-N-(2-piperidin-1-yl-thiazol-5-ylmethyl)-benzenesulfonamide | 484.1 | |
| 260 | 44-Chloro-N-(3,5-dimethyl-1-phenyl-1H-pyrazol-4-ylmethyl)-N-(2-oxo-azepan-3-yl)-benzenesulfonamide | 488.1 | |
| 261 | 4-Chloro-N-(2-oxo-azepan-3-yl)-N-(3-phenoxy-thiophen-2-ylmethyl)-benzenesulfonamide | | 514 |

| Ex. No. | Name | M + H+ | M + Na+ |
|---|---|---|---|
| 262 | 4-Chloro-N-(5-chloro-3-methyl-1-phenyl-1H-pyrazol-4-ylmethyl)-N-(2-oxo-azepan-3-yl)-benzenesulfonamide | 508.1 | |
| 263 | 4-Chloro-N-(3,5-di-tert-butyl-4-hydroxy-benzyl)-N-(2-oxo-azepan-3-yl)-benzenesulfonamide | | 544.2 |
| 264 | 4-Chloro-N-(2-oxo-azepan-3-yl)-N-[1-(toluene-4-sulfonyl)-1H-indol-3-ylmethyl]-benzenesulfonamide | | 609 |
| 265 | 4-Chloro-N-(3,5-dibromo-benzyl)-N-(2-oxo-azepan-3-yl)-benzenesulfonamide | 552 | |
| 266 | 4-Chloro-N-(2,3-dimethoxy-benzyl)-N-(2-oxo-azepan-3-yl)-benzenesulfonamide | 454.2 | |
| 267 | 4-Chloro-N-(3-fluoro-5-trifluoromethyl-benzyl)-N-92-oxo-azepan-3-yl)-benzenesulfonamide | 479.9 | |
| 268 | 4-Chloro-N-(6-chloro-imidazo[2,1-b]thiazol-5-ylmethyl)-N-(2-oxo-azepan-3-yl)-benzenesulfonamide | 474 | |
| 269 | 4-Chloro-N-(4-methylsulfanyl-benzyl)-N-(2-oxo-azepan-3-yl)-benzenesulfonamide | | 462 |
| 270 | 4-Chloro-N-92,3-difluoro-benzyl)-N-(2-oxo-azepan-3-yl)-benzenesulfonamide | 430.1 | |
| 270 | 4-Chloro-N-(5-ethyl-thiophen-2-ylmethyl)-N-(2-oxo-azepan-3-yl)-benzenesulfonamide | | 450.1 |
| 271 | 4-Chloro-N-(2-oxo-azepan-3-yl)-N-(3-vinyl-benzyl)-benzenesulfonamide | 420.1 | |
| 272 | 4-Chloro-N-(2-fluoro-benzyl)-N-(2-oxo-azepan-3-yl)-benzenesulfonamide | 412.1 | |
| 273 | 4-chloro-N-(3-methylbutyl)-N-[(3R)-2-oxoazepan-3-yl]benzenesulfonamide | 373.8 | |
| 274 | 4-chloro-N-[(3R)-2-oxoazepan-3-yl]-N-(3-phenoxypropyl)benzenesulfonamide | 437.8 | |
| 275 | methyl 4-({[(4-chlorophenyl)sulfonyl][(3R)-2-oxoazepan-3-yl]amino}methyl)benzoate | 451.8 | |
| 276 | N-(2-bromobeenzyl)-4-chloro-N-[(3R)-2-oxoazepan-3-yl]benzenesulfonamide | 472.7 | |
| 277 | N-(4-bromobenzyl)-4-chloro-N-[(3R)-2-oxoazepan-3-yl]benzenesulfonamide | 472.7 | |
| 278 | methyl 3-({[(4-chlorophenyl)sulfonyl][(3R)-2-oxoazepan-3-yl]amino}methyl)benzoate | 451.8 | |
| 279 | 4-chloro-N-(2-methylbenzyl)-N-[(3R)-2-oxoazepan-3-yl]benzenesulfonamide | 407.8 | |
| 280 | 4-Chloro-N-(4-fluoro-benzyl)-N-(2-oxo-azepan-3-yl)-benzenesulfonamide | 412.1 | |
| 281 | 4-Chloro-N-(3-cyano-benzyl)-N-(2-oxo-azepan-3-yl)-benzenesulfonamide | 419.1 | |
| 282 | 4-Chloro-N-(2-chloro-benzyl)-N-(2-oxo-azepan-3-yl)-benzenesulfonamide | 428 | |
| 283 | 4-Chloro-N-(3-chloro-benzyl)-N-(2-oxo-azepan-3-yl)-benzenesulfonamide | 428 | |
| 284 | 4-Chloro-N-(4-chloro-benzyl)-N-(2-oxo-azepan-3-yl)-benzenesulfonamide | 428.1 | |
| 285 | 4-Chloro-N-(3,4-difluoro-benzyl)-N-(2-oxo-azepan-3-yl)-benzenesulfonamide | 430.1 | |
| 286 | 4-Chloro-N-(2,4-difluoro-benzyl)-N-(2-oxo-azepan-3-yl)-benzenesulfonamide | 430.2 | |
| 287 | 4-Chloro-N-92-oxo-piperidin-3-yl)-N-(3-phenyl-propyl)-benzenesulfonamide | 428 | |
| 288 | 4-Chloro-N-(2-methyl-3-phenyl-allyl)-N-(2-oxo-piperidin-3-yl)-benzenesulfonamide | 416 | |
| 289 | 4-Chloro-N-(3,4-dimethoxy-benzyl)-N-(2-oxo-piperidin-3-yl)-benzenesulfonamide | | 428 |
| 290 | N-(4-Bromo-benzyl)-4-chloro-N-(2-oxo-piperidin-3-yl)-benzenesulfonamide | | 432 |
| 291 | 4-Chloro-N-(2-oxo-piperidin-3-yl)-N-(3-phenyl-allyl)-benzenesulfonamide | | 462 |
| 292 | 4-Chloro-N-(4-methoxy-benzyl)-N-(2-oxo-piperidin-3-yl)-benzenesulfonamide | 459 | |
| 293 | 4-Chloro-N-(3-fluoro-4-methoxy-benzyl)-N-92-oxo-piperidin-3-yl)-benzenesulfonamide | 408 | |

-continued

| Ex. No. | Name | M + H+ | M + Na+ |
|---|---|---|---|
| 294 | 4-Chloro-N-(2,4-difluoro-benzyl)-N-(2-oxo-piperidin-3-yl)-benzenesulfonamide | | 442 |
| 295 | 4-Chloro-N-(3-fluoro-4-methoxy-benzyl)-N-(2-oxo-pyrrolidin-3-yl)-benzenesulfonamide | | 436 |
| 296 | 4-Chloro-N-(2,4-difluoro-beenzyl)-N-(2-oxo-pyrrolidin-3-yl)-benzenesulfonamide | 401 | |
| 297 | 4-Chloro-N-(2-oxo-pyrrolidin-3-yl)-N-(3-phenyl-allyl)-benzenesulfonamide | | 414 |
| 298 | 4-Chloro-N-(4-methoxy-benzyl)-N-(2-oxo-pyrrolidin-3-yl)-benzenesulfonamide | | 418 |
| 299 | 4-Chloro-N-(3,4-dimethoxy-benzyl)-N-(2-oxo-pyrrolidin-3-yl)-benzenesulfonamide | | 448 |
| 300 | N-(4-Bromo-benzyl)-4-chloro-N-(2-oxo-pyrrolidin-3-yl)-benzenesulfonamide | 444 | |
| 301 | 4-Chloro-N-(2-oxo-pyrrolidin-3-yl)-N-(3-phenyl-propyl)-benzenesulfonamide | 393 | |
| 302 | 4-Chloro-N-(2-methyl-3-phenyl-allyl)-N-(2-oxo-pyrrolidin-3-yl)-benzenesulfonamide | | 428 |
| 303 | N-(3-Benzyloxy-propyl)-4-chloro-N-(2-oxo-azepan-3-yl)-benzenesulfonamide | 451.9 | |
| 304 | 4-Chloro-N-(2-oxo-azepan-3-yl)-N-(4-trifluoromethoxy-benzyl)-benzenesulfonamide | 477.7 | |
| 305 | 4-Chloro-N-(3,5-difluoro-benzyl)-N-(2-oxo-azepan-3-yl)-benzenesulfonamide | 429.8 | |
| 306 | 4-Chloro-N-[3-(4-fluoro-phenoxy)-benzyl]-N-(2-oxo-azepan-3-yl)-benzenesulfonamide | 503.8 | |
| 307 | 4-Chloro-N-(8-hydroxy-octyl)-N-(2-oxo-azepan-3-yl)-benzenesulfonamide | 431.9 | |
| 308 | 4-Chloro-N-(6-methyl-heptyl)-N-(2-oxo-azepan-3-yl)-benzenesulfonamide | 415.9 | |
| 309 | 4-Chloro-N-(4-methyl-pentyl)-N-(2-oxo-azepan-3-yl)-benzenesulfonamide | 387.8 | |
| 310 | 4-Chloro-N-[4-(1,3-dioxo-1,3-dihydro-isoindol-2-yl)-butyl]-N-(2-oxo-azepan-3-yl)-benzenesulfonamide | 504.9 | |
| 311 | N-But-3-enyl-4-chloro-N-(2-oxo-azepan-3-yl)-benzenesulfonamide | 357.7 | |
| 312 | 4-Chloro-N-(2-oxo-azepan-3-yl)-N-prop-2-ynyl-benzenesulfonamide | 341.8 | |
| 313 | 4-Chloro-N-[3-(1,3-dioxo-1,3-dihydro-isoindol-2-yl)-propyl]-N-(2-oxo-azepan-3-yl)-benzenesulfonamide | 490.9 | |
| 314 | 4-Chloro-N-(3,5-dimethoxy-benzyl)-N-(2-oxo-azepan-3-yl)-benzenesulfonamide | 453.7 | |
| 315 | 4-Chloro-N-(2-oxo-azepan-3-yl)-N-(3-phenoxy-propyl)-benzenesulfonamide | 437.8 | |
| 316 | 4-Chloro-N-(6,7-dihydroxy-3,7-dimethyl-octyl)-N-(2-oxo-azepan-3-yl)-benzenesulfonamide | 475.6 | |
| 317 | 6-[(4-Chloro-benzenesulfonyl)-(2-oxo-azepan-3-yl)-amino]-hexanoic acid ethyl ester | 445.8 | |

-continued

| Ex. No. | Name | M + H⁺ | M + Na⁺ |
|---|---|---|---|
| 318 | 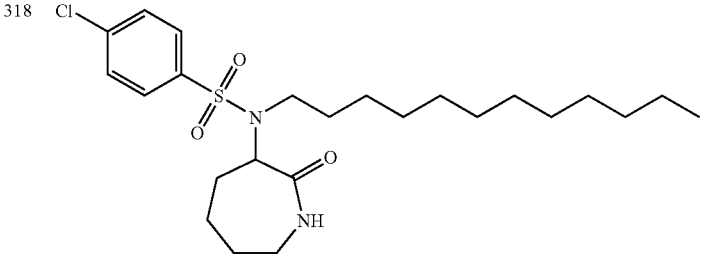

4-Chloro-N-dodcecyl-N-(2-oxo-azepan-3-yl)-benzenesulfonamide | 471.9 | |
| 319 | 4-[(4-Chloro-benzenesulfonyl)-(2-oxo-azepan-3-yl)-amino]-butyric acid ethyl ester | 417.8 | |
| 320 | 4-Chloro-N-[1,3]dioxolan-2-ylmethyl-N-(2-oxo-azepan-3-yl)-benzenesulfonamide | 389.6 | |
| 321 | 4-Chloro-N-(2-oxo-azepan-3-yl)-N-(3-trifluoromethoxy-benzyl)-benzenesulfonamide | 477.8 | |
| 322 | N-(2-Benzenesulfonylmethyl-benzyl)-4-chloro-N-(2-oxo-azepan-3-yl)-benzenesulfonamide | 547.7 | |
| 323 | 4-Chloro-N-(2-oxo-azepan-3-yl)-N-(tetrahydro-pyran-2-ylmethyl)-benzenesulfonamide | 401.8 | |
| 324 | 4-Chloro-N-(2-methoxy-ethyl)-N-(2-oxo-azepan-3-yl)-benzenesulfonamide | 361.8 | |
| 325 | 4-Chloro-N-(2-oxo-azepan-3-yl)-N-(4-phenoxy-butyl)-benzenesulfonamide | 451.8 | |
| 326 | N-(4-Benzyloxy-butyl)-4-chloro-N-(2-oxo-azepan-3-yl)-benzenesulfonamide | 465.8 | |
| 327 | 4-Chloro-N-{3-methoxy-4-[2-(4-methyl-thiazol-5-yl)-ethoxy]-benzyl}-N-(2-oxo-azepan-3-yl)-benzenesulfonamide | 565.6 | |
| 328 | 5-[(4-Chloro-benzenesulfonyl)-(2-oxo-azepan-3-yl)-amino]-pentanoic acid ethyl ester | 431.8 | |
| 329 | 4-Chloro-N-[2-(1,3-dioxo-1,3-dihydro-isoindol-2-yl)-ethyl]-N-(2-oxo-azepan-3-yl)-benzenesulfonamide | 476.9 | |
| 330 | 4-Chloro-N-(3,7-dimethyl-oct-6-enyl)-N-(2-oxo-azepan-3-yl)-benzenesulfonamide | 441.8 | |
| 331 | 4-Chloro-N-(2-oxo-azepan-3-yl)-N-(3,7,11-trimethyl-dodeca-2,6,10-trienyl)-benzenesulfonamide | | 530.1 |
| 332 | 4-Chloro-N-decyl-N-92-oxo-azepan-3-yl)-benzenesulfonamide | 443.9 | |
| 333 | 4-Chloro-N-(3,7-dimethyl-octa-2,6-dienyl)-N-92-oxo-azepan-3-yl)-benzenesulfonamide | | 462 |
| 334 | {2-[(4-Chloro-benzenesulfonyl)-(2-oxo-azepan-3-yl)-amino]-ethyl}-carbamic acid methyl ester | | 427.1 |
| 335 | {2-[(4-Chloro-benzenesulfonyl)-(2-oxo-azepan-3-yl)-amino]-1-methyl-ethyl}-carbamic acid tert-butyl ester | | 483.2 |
| 336 | 4-Chloro-N-(2-cyano-benzyl)-N-(2-oxo-azepan-3-yl)-benzenesulfonamide | | 440.9 |
| 337 | 3-[(4-Chloro-benzenesulfonyl)-(2-oxo-azepan-3-yl)-amino]-propionic acid | 375.8 | |
| 338 | 2-[(4-Chloro-benzenesulfonyl)-(2-oxo-azepan-3-yl)-amino]-acetamide | 360.7 | |

The following compounds can be prepared essentially according to the methods and procedures described above.

| | |
|---|---|
| 339 | 4-chloro-N-[(3R)-2-oxoazepan-3-yl]-N-[(2-oxo-2,3-dihydro-1H-benzimidazol-5-yl)methyl]benzenesulfonamide |
| 340 | 4-chloro-N-[(1,2-dimethyl-1H-benzimidazol-6-yl)methyl]-N-[(3R)-2-oxoazepan-3-yl]benzenesulfonamide |
| 341 | 4-chloro-N-[(3R)-2-oxoazepan-3-yl]-N-[(3-oxo-1,3-dihydro-2,1-benzisoxazol-6-yl)methyl]benzenesulfonamide |
| 342 | 4-chloro-N-[(2,3-dimethyl-2,3-dihydro-1,3-benzoxazol-5-yl)methyl]-N-[(3R)-2-oxoazepan-3-yl]benzenesulfonamide |
| 343 | 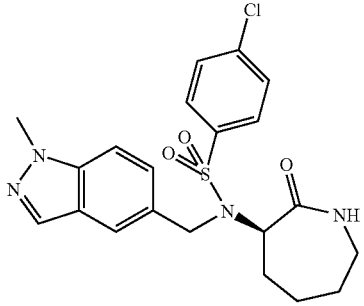 4-chloro-N-[(1-methyl-1H-indazol-5-yl)methyl]-N-[(3R)-2-oxoazepan-3-yl]benzenesulfonamide |
| 344 | 4-chloro-N-(furo[3,2-b]pyridin-5-ylmethyl)-N-[(3R)-2-oxoazepan-3-yl]benzenesulfonamide |
| 345 | N-(2,1,3-benzoxadiazol-5-ylmethyl)-4-chloro-N-[(3R)-2-oxoazepan-3-yl]benzenesulfonamide |
| 346 | 4-chloro-N-[(3,3-dimethyl-3H-indazol-6-yl)methyl]-N-[(3R)-2-oxoazepan-3-yl]benzenesulfonamide |
| 347 | 4-chloro-N-[(1,3-dimethyl-1H-pyrazolo[3,4-c]pyridin-5-yl)methyl]-N-[(3R)-2-oxoazepan-3-yl]benzenesulfonamide |
| 348 | 4-chloro-N-[(3R)-2-oxoazepan-3-yl]-N-(quinoxalin-6-ylmethyl)benzenesulfonamide |
| 349 | 4-chloro-N-[(3-oxido-1,4-dihydro-2,3,1,4-benzoxathiadiazin-6-yl)methyl]-N-[(3R)-2-oxoazepan-3-yl]benzenesulfonamide |
| 350 | 4-chloro-N-[(1-ethoxy-1H-1,2,3-benzotriazol-5-yl)methyl]-N-[(3R)-2-oxoazepan-3-yl]benzenesulfonamide |
| 351 | 4-chloro-N-[(1,3-dimethyl-1H-pyrazolo[3,4-b]pyridin-5-yl)methyl]-N-[(3R)-2-oxoazepan-3-yl]benzenesulfonamide |
| 352 | 4-chloro-N-(isoquinolin-7-ylmethyl)-N-[(3R)-2-oxoazepan-3-yl]benzenesulfonamide |
| 353 | 4-chloro-N-[(3R)-2-oxoazepan-3-yl]-N-(quinolin-6-ylmethyl)benzenesulfonamide |
| 354 | 4-chloro-N-[(3R)-2-oxoazepan-3-yl]-N-(quinolin-7-ylmethyl)benzenesulfonamide |
| 355 | 4-chloro-N-(isoquinolin-6-ylmethyl)-N-[(3R)-2-oxoazepan-3-yl]benzenesulfonamide |

The following compounds can be prepared essentially according to the methods and procedures described above.

| Cmpnd No. | Name | M + H | M + Na |
|---|---|---|---|
| 356 | 4-chloro-N-[(3R)-2-oxoazepan-3-yl]-N-[(1-phenyl-1H-1,2,3-triazol-4-yl)methyl]benzenesulfonamide | 460 | — |
| 357 | 4-chloro-N-[(3R)-2-oxoazepan-3-yl]-N-[(2-piperidin-1-yl-1,3-thiazol-5-yl)methyl]benzenesulfonamide | 483 | — |
| 358 | 4-chloro-N-[(6-methoxypyridin-3-yl)methyl]-N-[(3R)-2-oxoazepan-3-yl]benzenesulfonamide | 424 | — |
| 359 | N-[(6-bromopyridin-2-yl)methyl]-4-chloro-N-[(3R)-2-oxoazepan-3-yl]benzenesulfonamide | 473.9 | — |
| 360 | 4-chloro-N-[(3R)-2-oxoazepan-3-yl]-N-[(2E)-3-pyridin-3-ylprop-2-en-1-yl]benzenesulfonamide | 420 | — |
| 361 | 4-chloro-N-[(1-methyl-1H-indol-4-yl)methyl]-N-[(3R)-2-oxoazepan-3-yl]benzenesulfonamide | — | 468 |
| 362 | 4-chloro-N-[(5-chloro-1,3-dimethyl-1H-pyrazol-4-yl)methyl]-N-[(3R)-2-oxoazepan-3-yl]benzenesulfonamide | 444.9 | — |
| 363 | 4-chloro-N-[(1,3-dimethyl-1H-pyrazol-5-yl)methyl]-N-[(3R)-2-oxoazepan-3-yl]benzenesulfonamide | 410.9 | — |
| 364 | 4-chloro-N-[(6-chloropyridin-3-yl)methyl]-N-[(3R)-2-oxoazepan-3-yl]benzenesulfonamide | 427.9 | — |
| 365 | 4-chloro-N-[(3-methyl-1-benzothien-2-yl)methyl]-N-[(3R)-2-oxoazepan-3-yl]benzenesulfonamide | — | 484.9 |
| 366 | 4-chloro-N-{[5-cyano-6-(methylthio)pyridin-2-yl]methyl}-N-[(3R)-2-oxoazepan-3-yl]benzenesulfonamide | 464.9 | — |
| 367 | N-[(6-bromopyridin-3-yl)methyl]-4-chloro-N-[(3R)-2-oxoazepan-3-yl]benzenesulfonamide | 473.9 | — |
| 368 | 4-chloro-N-[(1-methyl-1H-imidazol-2-yl)methyl]-N-[(3R)-2-oxoazepan-3-yl]benzenesulfonamide | 396.9 | — |
| 369 | methyl 5-({[(4-chlorophenyl)sulfonyl][(3R)-2-oxoazepan-3-yl]amino}methyl)-1-methyl-1H-pyrrole-2-carboxylate | — | 475.9 |
| 370 | 4-chloro-N-[(1-methyl-1H-pyrrol-2-yl)methyl]-N-[(3R)-2-oxoazepan-3-yl]benzenesulfonamide | — | 417.9 |
| 371 | 4-chloro-N-[(6-methylpyridin-2-yl)methyl]-N-[(3R)-2-oxoazepan-3-yl]benzenesulfonamide | 407.9 | — |
| 372 | N-[(1-benzyl-1H-indol-3-yl)methyl]-4-chloro-N-[(3R)-2-oxoazepan-3-yl]benzenesulfonamide | — | 544 |
| 373 | 4-chloro-N-[(3R)-2-oxoazepan-3-yl]-N-(1,3-thiazol-2-ylmethyl)benzenesulfonamide | 399.9 | — |
| 374 | 4-chloro-N-[(5-methyl-2-furyl)methyl]-N-[(3R)-2-oxoazepan-3-yl]benzenesulfonamide | — | 418.9 |
| 375 | 4-chloro-N-[(5-methyl-2-thienyl)methyl]-N-[(3R)-2-oxoazepan-3-yl]benzenesulfonamide | — | 434.9 |
| 376 | 4-chloro-N-[(2-methyl-1H-imidazol-4-yl)methyl]-N-[(3R)-2-oxoazepan-3-yl]benzenesulfonamide | 397 | — |
| 377 | 4-chloro-N-{[5-(methylthio)-2-thienyl]methyl}-N-[(3R)-2-oxoazepan-3-yl]benzenesulfonamide | — | 466.9 |
| 378 | 4-chloro-N-[(5-chloro-2-furyl)methyl]-N-[(3R)-2-oxoazepan-3-yl]benzenesulfonamide | — | 438.9 |
| 379 | N-[(5-bromo-2-furyl)methyl]-4-chloro-N-[(3R)-2-oxoazepan-3-yl]benzenesulfonamide | — | 484.8 |
| 380 | 4-chloro-N-[(3R)-2-oxoazepan-3-yl]-N-[(6-piperidin-1-ylpyridin-3-yl)methyl]benzenesulfonamide | 477 | — |

-continued

| Cmpnd No. | Name | M + H | M + Na |
|---|---|---|---|
| 381 | 4-chloro-N-[(6-morpholin-4-ylpyridin-3-yl)methyl]-N-[(3R)-2-oxoazepan-3-yl]benzenesulfonamide | 479 | — |
| 382 | 4-chloro-N-[(1-methyl-1H-indol-3-yl)methyl]-N-[(3R)-2-oxoazepan-3-yl]benzenesulfonamide | — | 468 |
| 383 | 4-chloro-N-[(2-ethyl-1H-imidazol-5-yl)methyl]-N-[(3R)-2-oxoazepan-3-yl]benzenesulfonamide | 411 | — |
| 384 | 4-chloro-N-[(3R)-2-oxoazepan-3-yl]-N-[(2-phenyl-1H-imidazol-5-yl)methyl]benzenesulfonamide | 459 | — |
| 385 | N-[(2-butyl-1H-imidazol-4-yl)methyl]-4-chloro-N-[(3R)-2-oxoazepan-3-yl]benzenesulfonamide | 439 | — |
| 386 | 4-chloro-N-[(3R)-2-oxoazepan-3-yl]-N-{[6-(trifluoromethyl)pyridin-3-yl]methyl}benzenesulfonamide | 462 | — |
| 387 | 4-chloro-N-(1H-imidazol-5-ylmethyl)-N-[(3R)-2-oxoazepan-3-yl]benzenesulfonamide | 383 | — |
| 388 | 4-chloro-N-[(3R)-2-oxoazepan-3-yl]-N-(1,2,3-thiadiazol-4-ylmethyl)benzenesulfonamide | 400.9 | — |
| 389 | 4-chloro-N-(1H-imidazol-2-ylmethyl)-N-[(3R)-2-oxoazepan-3-yl]benzenesulfonamide | 383 | — |
| 390 | 4-chloro-N-[(3R)-2-oxoazepan-3-yl]-N-(1,3-thiazol-5-ylmethyl)benzenesulfonamide | 399.9 | — |
| 391 | 4-chloro-N-[(3R)-2-oxoazepan-3-yl]-N-(1H-pyrrol-2-ylmethyl)benzenesulfonamide | — | 403.9 |
| 392 | 4-chloro-N-[(2-chloro-1,3-thiazol-5-yl)methyl]-N-[(3R)-2-oxoazepan-3-yl]benzenesulfonamide | 433.9 | — |
| 393 | 4-chloro-N-{[2-(diethylamino)-1,3-thiazol-5-yl]methyl}-N-[(3R)-2-oxoazepan-3-yl]benzenesulfonamide | 471 | — |
| 394 | 4-chloro-N-[(3R)-2-oxoazepan-3-yl]-N-(quinolin-3-ylmethyl)benzenesulfonamide | 444 | — |
| 395 | 4-chloro-N-[(5-chloro-1,2,4-thiadiazol-3-yl)methyl]-N-[(3R)-2-oxoazepan-3-yl]benzenesulfonamide | 435 | — |
| 396 | 4-chloro-N-[(3R)-2-oxoazepan-3-yl]-N-[4-(1H-1,2,4-triazol-1-yl)benzyl]benzenesulfonamide | 460 | — |
| 397 | 4-chloro-N-{[5-(4-methoxyphenyl)-1,3,4-oxadiazol-2-yl]methyl}-N-[(3R)-2-oxoazepan-3-yl]benzenesulfonamide | 491 | — |
| 398 | 4-chloro-N-[2-fluoro-5-(trifluoromethyl)benzyl]-N-[(3R)-2-oxoazepan-3-yl]benzenesulfonamide | 479 | — |
| 399 | 4-chloro-N-{[5-(3,5-dimethylisoxazol-4-yl)-1,2,4-oxadiazol-3-yl]methyl}-N-[(3R)-2-oxoazepan-3-yl]benzenesulfonamide | 480 | — |
| 400 | 4-chloro-N-({4-methyl-2-[4-(trifluoromethyl)phenyl]-1,3-thiazol-5-yl}methyl)-N-[(3R)-2-oxoazepan-3-yl]benzenesulfonamide | 558 | — |
| 401 | 4-chloro-N-({5-[2-(methylthio)pyridin-3-yl]-1,2,4-oxadiazol-3-yl}methyl)-N-[(3R)-2-oxoazepan-3-yl]benzenesulfonamide | 508 | — |
| 402 | 4-chloro-N-(3-fluoro-4-methylbenzyl)-N-[(3R)-2-oxoazepan-3-yl]benzenesulfonamide | 425 | — |
| 403 | 4-chloro-N-[(1-methyl-1H-1,2,3-benzotriazol-5-yl)methyl]-N-[(3R)-2-oxoazepan-3-yl]benzenesulfonamide | 448 | — |
| 404 | 4-chloro-N-[(5-methylisoxazol-3-yl)methyl]-N-[(3R)-2-oxoazepan-3-yl]benzenesulfonamide | 398 | — |
| 405 | 4-chloro-N-[(3R)-2-oxoazepan-3-yl]-N-(pentafluorobenzyl)benzenesulfonamide | 482.9 | — |
| 406 | 4-chloro-N-[(3R)-2-oxoazepan-3-yl]-N-{[(2S)-5-oxopyrrolidin-2-yl]methyl}benzenesulfonamide | 400 | — |
| 407 | 5-({[(4-chlorophenyl)sulfonyl][(3R)-2-oxoazepan-3-yl]amino}methyl)-N-phenylthiophene-2-carboxamide | 518 | — |
| 408 | 5-({[(4-chlorophenyl)sulfonyl][(3R)-2-oxoazepan-3-yl]amino}methyl)-N-(2-furylmethyl)thiophene-2-carboxamide | 522 | — |
| 409 | 5-({[(4-chlorophenyl)sulfonyl][(3R)-2-oxoazepan-3-yl]amino}methyl)-N-(1-methylpiperidin-4-yl)thiophene-2-carboxamide | 539 | — |
| 410 | 5-({[(4-chlorophenyl)sulfonyl][(3R)-2-oxoazepan-3-yl]amino}methyl)-N-[(1R)-1-phenylethyl]thiophene-2-carboxamide | 546 | — |
| 411 | 5-({[(4-chlorophenyl)sulfonyl][(3R)-2-oxoazepan-3-yl]amino}methyl)-N-(2-pyridin-3-ylethyl)thiophene-2-carboxamide | 547 | — |
| 412 | 5-({[(4-chlorophenyl)sulfonyl][(3R)-2-oxoazepan-3-yl]amino}methyl)-N-[(1S)-1-phenylethyl]thiophene-2-carboxamide | 546 | — |
| 413 | N-butyl-5-({[(4-chlorophenyl)sulfonyl][(3R)-2-oxoazepan-3-yl]amino}methyl)thiophene-2-carboxamide | 498 | — |
| 414 | 5-({[(4-chlorophenyl)sulfonyl][(3R)-2-oxoazepan-3-yl]amino}methyl)-N-cyclopropyl-2-furamide | 467 | — |
| 415 | 5-({[(4-chlorophenyl)sulfonyl][(3R)-2-oxoazepan-3-yl]amino}methyl)-N-(2-furylmethyl)-2-furamide | 506 | — |
| 416 | 5-({[(4-chlorophenyl)sulfonyl][(3R)-2-oxoazepan-3-yl]amino}methyl)-N-(1-methylpiperidin-4-yl)-2-furamide | 523 | — |
| 417 | 5-({[(4-chlorophenyl)sulfonyl][(3R)-2-oxoazepan-3-yl]amino}methyl)-N-[(1R)-1-phenylethyl]-2-furamide | 530 | — |
| 418 | 5-({[(4-chlorophenyl)sulfonyl][(3R)-2-oxoazepan-3-yl]amino}methyl)-N-(2-pyridin-3-ylethyl)-2-furamide | 531 | — |
| 419 | N-butyl-5-({[(4-chlorophenyl)sulfonyl][(3R)-2-oxoazepan-3-yl]amino}methyl)-2-furamide | 482 | — |
| 420 | N-benzyl-5-({[(4-chlorophenyl)sulfonyl][(3R)-2-oxoazepan-3-yl]amino}methyl)-2-furamide | 516 | — |
| 421 | N-(4-benzoylbenzyl)-4-chloro-N-[(3R)-2-oxoazepan-3-yl]benzenesulfonamide | 496.8 | — |
| 422 | N-(2-aminoethyl)-4-({[(4-chlorophenyl)sulfonyl][(3R)-2-oxoazepan-3-yl]amino}methyl)benzamide | 479 | — |
| 423 | tert-butyl 4-({[(4-chlorophenyl)sulfonyl][(3R)-2-oxoazepan-3-yl]amino}methyl)piperidine-1-carboxylate | — | 522 |

The following compounds can be prepared essentially according to the methods and procedures described above.

| Cmpnd. No. | Name | M + H | M + Na |
|---|---|---|---|
| 424 | 4-chloro-N-(4-nitrobenzyl)-N-[(3R)-2-oxoazepan-3-yl]benzenesulfonamide | 437.0 | — |
| 425 | ethyl (2E)-4-{[(4-chlorophenyl)sulfonyl][(3R)-2-oxoazepan-3-yl]amino}-3-methylbut-2-enoate | 429.0 | — |
| 426 | ethyl 2-({[(4-chlorophenyl)sulfonyl][(3R)-2-oxoazepan-3-yl]amino}methyl)cyclopropanecarboxylate | 429.0 | — |
| 427 | methyl 6-{[(4-chlorophenyl)sulfonyl][(3R)-2-oxoazepan-3-yl]amino}hexanoate | 431.0 | — |
| 428 | 4-chloro-N-(cyclopropylmethyl)-N-[(3R)-2-oxoazepan-3-yl]benzenesulfonamide | 357.0 | — |
| 429 | 4-chloro-N-[4-(methylthio)benzyl]-N-[(3R)-2-oxoazepan-3-yl]benzenesulfonamide | — | 460.9 |
| 430 | 4-chloro-N-[4-(methylsulfinyl)benzyl]-N-[(3R)-2-oxoazepan-3-yl]benzenesulfonamide | 454.9 | — |
| 431 | 4-chloro-N-[4-(methylsulfonyl)benzyl]-N-[(3R)-2-oxoazepan-3-yl]benzenesulfonamide | 470.9 | — |
| 432 | N-(4-aminobenzyl)-4-chloro-N-[(3R)-2-oxoazepan-3-yl]benzenesulfonamide | — | 429.9 |

-continued

| Cmpnd. No. | Name | M + H | M + Na |
|---|---|---|---|
| 433 | N-[4-({[(4-chlorophenyl)sulfonyl][(3R)-2-oxoazepan-3-yl]amino}methyl)phenyl]benzamide | — | 533.9 |
| 434 | N-[4-({[(4-chlorophenyl)sulfonyl][(3R)-2-oxoazepan-3-yl]amino}methyl)phenyl]butanamide | — | 500.0 |
| 435 | N-[4-({[(4-chlorophenyl)sulfonyl][(3R)-2-oxoazepan-3-yl]amino}methyl)phenyl]cyclohexanecarboxamide | — | 540.0 |
| 436 | N-[4-({[(4-chlorophenyl)sulfonyl][(3R)-2-oxoazepan-3-yl]amino}methyl)phenyl]pyridine-2-carboxamide | — | 535.0 |
| 437 | N-[4-({[(4-chlorophenyl)sulfonyl][(3R)-2-oxoazepan-3-yl]amino}methyl)phenyl]pyrazine-2-carboxamide | — | 536.0 |
| 438 | methyl [4-({[(4-chlorophenyl)sulfonyl][(3R)-2-oxoazepan-3-yl]amino}methyl)phenyl]carbamate | — | 488.0 |
| 439 | phenyl [4-({[(4-chlorophenyl)sulfonyl][(3R)-2-oxoazepan-3-yl]amino}methyl)phenyl]carbamate | — | 550.0 |
| 440 | isopropyl [4-({[(4-chlorophenyl)sulfonyl][(3R)-2-oxoazepan-3-yl]amino}methyl)phenyl]carbamate | — | 515.9 |
| 441 | 4-chloro-N-(4-{[(methylamino)carbonyl]amino}benzyl)-N-[(3R)-2-oxoazepan-3-yl]benzenesulfonamide | — | 487.0 |
| 442 | 4-chloro-N-(4-{[(isopropylamino)carbonyl]amino}benzyl)-N-[(3R)-2-oxoazepan-3-yl]benzenesulfonamide | — | 515.0 |
| 443 | N-{4-[(anilinocarbonyl)amino]benzyl}-4-chloro-N-[(3R)-2-oxoazepan-3-yl]benzenesulfonamide | — | 549.0 |
| 444 | 4-chloro-N-[(3R)-2-oxoazepan-3-yl]-N-[4-({[(2-phenylethyl)amino]carbonyl}amino)benzyl]benzenesulfonamide | — | 577.0 |
| 445 | 4-chloro-N-[4-({[(3,5-dimethylisoxazol-4-yl)amino]carbonyl}amino)benzyl]-N-[(3R)-2-oxoazepan-3-yl]benzenesulfonamide | — | 568.0 |
| 446 | 4-({[(4-chlorophenyl)sulfonyl][(3R)-2-oxoazepan-3-yl]amino}methyl)-N-(2,2-dimethylpropyl)benzamide | 506.1 | — |
| 447 | 4-({[(4-chlorophenyl)sulfonyl][(3R)-2-oxoazepan-3-yl]amino}methyl)-N-(1-methylpiperidin-4-yl)benzamide | 533.0 | — |
| 448 | 4-({[(4-chlorophenyl)sulfonyl][(3R)-2-oxoazepan-3-yl]amino}methyl)-N-(1-methyl-1-phenylethyl)benzamide | 554.0 | — |
| 449 | 4-({[(4-chlorophenyl)sulfonyl][(3R)-2-oxoazepan-3-yl]amino}methyl)-N-(2-pyridin-3-ylethyl)benzamide | 541.0 | — |
| 450 | 4-({[(4-chlorophenyl)sulfonyl][(3R)-2-oxoazepan-3-yl]amino}methyl)-N-[(1,5-dimethyl-1H-pyrazol-3-yl)methyl]benzamide | 544.0 | — |
| 451 | 4-({[(4-chlorophenyl)sulfonyl][(3R)-2-oxoazepan-3-yl]amino}methyl)-N-(2-methylprop-2-en-1-yl)benzamide | 490.0 | — |
| 452 | 4-({[(4-chlorophenyl)sulfonyl][(3R)-2-oxoazepan-3-yl]amino}methyl)-N,N-diethylbenzamide | 492.0 | — |
| 453 | N-[2-(tert-butylthio)ethyl]-4-({[(4-chlorophenyl)sulfonyl][(3R)-2-oxoazepan-3-yl]amino}methyl)benzamide | 552.0 | — |
| 454 | 4-({[(4-chlorophenyl)sulfonyl][(3R)-2-oxoazepan-3-yl]amino}methyl)-N-(4-methylcyclohexyl)benzamide | 532.0 | — |
| 455 | 4-({[(4-chlorophenyl)sulfonyl][(3R)-2-oxoazepan-3-yl]amino}methyl)-N-cyclobutylbenzamide | 490.0 | — |
| 456 | 4-({[(4-chlorophenyl)sulfonyl][(3R)-2-oxoazepan-3-yl]amino}methyl)-N-cyclopentylbenzamide | 504.0 | — |
| 457 | 4-({[(4-chlorophenyl)sulfonyl][(3R)-2-oxoazepan-3-yl]amino}methyl)-N-(2,3-dihydro-1H-inden-2-yl)benzamide | 552.0 | — |
| 458 | 4-({[(4-chlorophenyl)sulfonyl][(3R)-2-oxoazepan-3-yl]amino}methyl)-N-cyclopropylbenzamide | 476.0 | — |
| 459 | 4-({[(4-chlorophenyl)sulfonyl][(3R)-2-oxoazepan-3-yl]amino}methyl)-N-[2-(dimethylamino)-1-methylethyl]benzamide | 521.1 | — |
| 460 | 4-({[(4-chlorophenyl)sulfonyl][(3R)-2-oxoazepan-3-yl]amino}methyl)-N-(2-oxotetrahydrofuran-3-yl)benzamide | 519.9 | — |
| 461 | 4-({[(4-chlorophenyl)sulfonyl][(3R)-2-oxoazepan-3-yl]amino}methyl)-N-(2,3-dihydro-1H-inden-1-yl)benzamide | 552.0 | — |
| 462 | 4-({[(4-chlorophenyl)sulfonyl][(3R)-2-oxoazepan-3-yl]amino}methyl)-N-[4-(diethylamino)-1-methylbutyl]benzamide | 577.0 | — |
| 463 | 4-({[(4-chlorophenyl)sulfonyl][(3R)-2-oxoazepan-3-yl]amino}methyl)-N-(2-pyrrolidin-1-ylethyl)benzamide | 533.1 | — |
| 464 | 4-({[(4-chlorophenyl)sulfonyl][(3R)-2-oxoazepan-3-yl]amino}methyl)-N-(2-methylbutyl)benzamide | 506.0 | — |
| 465 | 4-({[(4-chlorophenyl)sulfonyl][(3R)-2-oxoazepan-3-yl]amino}methyl)-N-(2-isopropoxyethyl)benzamide | 522.0 | — |
| 466 | 4-({[(4-chlorophenyl)sulfonyl][(3R)-2-oxoazepan-3-yl]amino}methyl)-N-cyclohexylbenzamide | 518.0 | — |
| 467 | 4-({[(4-chlorophenyl)sulfonyl][(3R)-2-oxoazepan-3-yl]amino}methyl)-N-[3-(methylthio)propyl]benzamide | 524.0 | — |
| 468 | 4-({[(4-chlorophenyl)sulfonyl][(3R)-2-oxoazepan-3-yl]amino}methyl)-N-(2-furylmethyl)benzamide | 516.0 | — |
| 469 | 4-({[(4-chlorophenyl)sulfonyl][(3R)-2-oxoazepan-3-yl]amino}methyl)-N-(3-phenylpropyl)benzamide | 554.0 | — |
| 470 | 4-({[(4-chlorophenyl)sulfonyl][(3R)-2-oxoazepan-3-yl]amino}methyl)-N-[2-(2-hydroxyethoxy)ethyl]benzamide | 524.1 | — |
| 471 | 4-({[(4-chlorophenyl)sulfonyl][(3R)-2-oxoazepan-3-yl]amino}methyl)-N-pyridin-3-ylbenzamide | 513.0 | — |
| 472 | 4-({[(4-chlorophenyl)sulfonyl][(3R)-2-oxoazepan-3-yl]amino}methyl)-N-propylbenzamide | 478.0 | — |
| 473 | N-butyl-4-({[(4-chlorophenyl)sulfonyl][(3R)-2-oxoazepan-3-yl]amino}methyl)benzamide | 492.0 | — |
| 474 | N-benzyl-4-({[(4-chlorophenyl)sulfonyl][(3R)-2-oxoazepan-3-yl]amino}methyl)benzamide | 526.0 | — |
| 475 | 4-({[(4-chlorophenyl)sulfonyl][(3R)-2-oxoazepan-3-yl]amino}methyl)-N-(3,5-difluorobenzyl)benzamide | 562.0 | — |
| 476 | 4-({[(4-chlorophenyl)sulfonyl][(3R)-2-oxoazepan-3-yl]amino}methyl)-N-(1-phenylethyl)benzamide | 540.0 | — |
| 477 | 4-chloro-N-{4-[(2,5-dimethyl-2,5-dihydro-1H-pyrrol-1-yl)carbonyl]benzyl}-N-[(3R)-2-oxoazepan-3-yl]benzenesulfonamide | 516.0 | — |
| 478 | 4-chloro-N-[(3R)-2-oxoazepan-3-yl]-N-[4-(pyrrolidin-1-ylcarbonyl)benzyl]benzenesulfonamide | 490.0 | — |
| 479 | 4-({[(4-chlorophenyl)sulfonyl][(3R)-2-oxoazepan-3-yl]amino}methyl)-N-isopropylbenzamide | 478.0 | — |
| 480 | N-(tert-butyl)-4-({[(4-chlorophenyl)sulfonyl][(3R)-2-oxoazepan-3-yl]amino}methyl)benzamide | 492.0 | — |
| 481 | 4-({[(4-chlorophenyl)sulfonyl][(3R)-2-oxoazepan-3-yl]amino}methyl)-N-(2-hydroxy-2-phenylethyl)benzamide | 556.0 | — |
| 482 | 4-({[(4-chlorophenyl)sulfonyl][(3R)-2-oxoazepan-3-yl]amino}methyl)-N-cyclohexyl-N-methylbenzamide | 532.1 | — |
| 483 | 4-({[(4-chlorophenyl)sulfonyl][(3R)-2-oxoazepan-3-yl]amino}methyl)-N-(2-phenylethyl)benzamide | 540.0 | — |
| 484 | 4-({[(4-chlorophenyl)sulfonyl][(3R)-2-oxoazepan-3-yl]amino}methyl)-N-1,3-thiazol-2-ylbenzamide | 518.9 | — |
| 485 | 4-({[(4-chlorophenyl)sulfonyl][(3R)-2-oxoazepan-3-yl]amino}methyl)-N-phenylbenzamide | 512.0 | — |
| 486 | 4-({[(4-chlorophenyl)sulfonyl][(3R)-2-oxoazepan-3-yl]amino}methyl)-N-isobutylbenzamide | 492.0 | — |
| 487 | 4-({[(4-chlorophenyl)sulfonyl][(3R)-2-oxoazepan-3-yl]amino}methyl)-N-(2-methylcyclohexyl)benzamide | 532.1 | — |
| 488 | 4-({[(4-chlorophenyl)sulfonyl][(3R)-2-oxoazepan-3-yl]amino}methyl)-N-cyclopentyl-N-methylbenzamide | 518.1 | — |
| 489 | 4-({[(4-chlorophenyl)sulfonyl][(3R)-2-oxoazepan-3-yl]amino}methyl)-N,N-diisopropylbenzamide | 520.1 | — |
| 490 | 4-({[(4-chlorophenyl)sulfonyl][(3R)-2-oxoazepan-3-yl]amino}methyl)-N-[(5-methylpyrazin-2-yl)methyl]benzamide | 542.0 | — |
| 491 | 4-({[(4-chlorophenyl)sulfonyl][(3R)-2-oxoazepan-3-yl]amino}methyl)-N-(4-hydroxycyclohexyl)benzamide | 534.0 | — |
| 492 | 4-chloro-N-(cyanomethyl)-N-[(3R)-2-oxoazepan-3-yl]benzenesulfonamide | 342.0 | — |
| 493 | 4-chloro-N-[(3R)-2-oxoazepan-3-yl]-N-[4-(4,4,5,5-tetramethyl-1,3,2-dioxaborolan-2-yl)benzyl]benzenesulfonamide | 519.0 | — |
| 494 | tert-butyl [4-({[(4-chlorophenyl)sulfonyl][(3R)-2-oxoazepan-3-yl]amino}methyl)-2-fluorophenyl]carbamate | — | 548.0 |
| 495 | N-benzyl-2-[4-({[(4-chlorophenyl)sulfonyl][(3R)-2-oxoazepan-3-yl]amino}methyl)phenyl]acetamide | 540.0 | — |
| 496 | 4-chloro-N-[(3R)-2-oxoazepan-3-yl]-N-[4-(2-oxo-2-pyrrolidin-1-ylethyl)benzyl]benzenesulfonamide | 504.0 | — |
| 497 | 2-[4-({[(4-chlorophenyl)sulfonyl][(3R)-2-oxoazepan-3-yl]amino}methyl)phenyl]-N-(3,5-difluorobenzyl)acetamide | 576.0 | — |
| 498 | 2-[4-({[(4-chlorophenyl)sulfonyl][(3R)-2-oxoazepan-3-yl]amino}methyl)phenyl]-N-cyclohexylpropanamide | — | 568.0 |
| 499 | 2-[4-({[(4-chlorophenyl)sulfonyl][(3R)-2-oxoazepan-3-yl]amino}methyl)phenoxy]-N-cyclohexylacetamide | — | 570.0 |
| 500 | N-benzyl-2-[4-({[(4-chlorophenyl)sulfonyl][(3R)-2-oxoazepan-3-yl]amino}methyl)phenoxy]acetamide | — | 578.0 |
| 501 | N-[4-({[(4-chlorophenyl)sulfonyl][(3R)-2-oxoazepan-3-yl]amino}methyl)-2-fluorophenyl]-2-phenylacetamide | — | 566.0 |
| 502 | N-[4-({[(4-chlorophenyl)sulfonyl][(3R)-2-oxoazepan-3-yl]amino}methyl)-2-fluorophenyl]benzamide | — | 552.0 |
| 503 | N-[4-({[(4-chlorophenyl)sulfonyl][(3R)-2-oxoazepan-3-yl]amino}methyl)-2-fluorophenyl]butanamide | — | 518.0 |
| 504 | N-[4-({[(4-chlorophenyl)sulfonyl][(3R)-2-oxoazepan-3-yl]amino}methyl)-2-fluorophenyl]pyridine-2-carboxamide | — | 553.0 |
| 505 | N-[4-({[(4-chlorophenyl)sulfonyl][(3R)-2-oxoazepan-3-yl]amino}methyl)-2-fluorophenyl]-4-phenylbutanamide | — | 594.0 |
| 506 | 4-({[(4-chlorophenyl)sulfonyl][(3R)-2-oxoazepan-3-yl]amino}methyl)-N-[(1R)-1-(4-methoxyphenyl)ethyl]benzamide | 570.0 | — |
| 507 | 4-({[(4-chlorophenyl)sulfonyl][(3R)-2-oxoazepan-3-yl]amino}methyl)-N-[(1R)-1-(4-fluorophenyl)ethyl]benzamide | 558.0 | — |
| 508 | 4-chloro-N-{4-[(6-fluoro-2-methyl-3,4-dihydroquinolin-1(2H)-yl)carbonyl]benzyl}-N-[(3R)-2-oxoazepan-3-yl]benzenesulfonamide | 584.0 | — |

-continued

| Cmpnd. No. | Name | M + H | M + Na |
|---|---|---|---|
| 509 | 4-({[(4-chlorophenyl)sulfonyl][(3R)-2-oxoazepan-3-yl]amino}methyl)-N-(2-thienylmethyl)benzamide | 532.0 | — |
| 510 | 4-({[(4-chlorophenyl)sulfonyl][(3R)-2-oxoazepan-3-yl]amino}methyl)-N-[1-(methoxymethyl)propyl]benzamide | 522.0 | — |
| 511 | ethyl 4-{[4-({[(4-chlorophenyl)sulfonyl][(3R)-2-oxoazepan-3-yl]amino}methyl)benzoyl]amino}piperidine-1-carboxylate | 591.0 | — |
| 512 | 4-({[(4-chlorophenyl)sulfonyl][(3R)-2-oxoazepan-3-yl]amino}methyl)-N-[(1S,2R)-2-hydroxy-2,3-dihydro-1H-inden-1-yl]benzamide | 568.0 | — |
| 513 | N-[(1S)-2-(benzyloxy)-1-(hydroxymethyl)ethyl]-4-({[(4-chlorophenyl)sulfonyl][(3R)-2-oxoazepan-3-yl]amino}methyl)benzamide | 599.0 | — |
| 514 | 4-({[(4-chlorophenyl)sulfonyl][(3R)-2-oxoazepan-3-yl]amino}methyl)-N-[(1R)-2-hydroxy-1-phenylethyl]benzamide | 556.0 | — |
| 515 | 4-chloro-N-[4-(3,4-dihydroisoquinolin-2(1H)-ylcarbonyl)benzyl]-N-[(3R)-2-oxoazepan-3-yl]benzenesulfonamide | 552.0 | — |
| 516 | N-(4-{[(2S)-2-(anilinomethyl)pyrrolidin-1-yl]carbonyl}benzyl)-4-chloro-N-[(3R)-2-oxoazepan-3-yl]benzenesulfonamide | 595.0 | — |
| 517 | N-(3-tert-butyl-1-methyl-1H-pyrazol-5-yl)-4-({[(4-chlorophenyl)sulfonyl][(3R)-2-oxoazepan-3-yl]amino}methyl)benzamide | 572.0 | — |
| 518 | 4-({[(4-chlorophenyl)sulfonyl][(3R)-2-oxoazepan-3-yl]amino}methyl)-N-[3-(2-furyl)-1H-pyrazol-5-yl]benzamide | 568.0 | — |
| 519 | 4-({[(4-chlorophenyl)sulfonyl][(3R)-2-oxoazepan-3-yl]amino}methyl)-N-[2-morpholin-4-yl-5-(trifluoromethyl)phenyl]benzamide | 665.0 | — |
| 520 | 4-({[(4-chlorophenyl)sulfonyl][(3R)-2-oxoazepan-3-yl]amino}methyl)-N-[2-(1H-pyrrol-1-yl)phenyl]benzamide | 577.0 | — |
| 521 | N-(4-acetylphenyl)-4-({[(4-chlorophenyl)sulfonyl][(3R)-2-oxoazepan-3-yl]amino}methyl)benzamide | 554.0 | — |
| 522 | 4-({[(4-chlorophenyl)sulfonyl][(3R)-2-oxoazepan-3-yl]amino}methyl)-N-(3-phenyl-1H-pyrazol-5-yl)benzamide | 578.0 | — |
| 523 | 4-({[(4-chlorophenyl)sulfonyl][(3R)-2-oxoazepan-3-yl]amino}methyl)-N-(1-phenyl-1H-pyrazol-5-yl)benzamide | 578.0 | — |
| 524 | N-(5-tert-butylisoxazol-3-yl)-4-({[(4-chlorophenyl)sulfonyl][(3R)-2-oxoazepan-3-yl]amino}methyl)benzamide | 559.0 | — |
| 525 | N-(6-bromopyridin-2-yl)-4-({[(4-chlorophenyl)sulfonyl][(3R)-2-oxoazepan-3-yl]amino}methyl)benzamide | 593.0 | — |
| 526 | N-benzyl-4-({[(3,5-difluorophenyl)sulfonyl][(3R)-2-oxoazepan-3-yl]amino}methyl)benzamide | 528.0 | — |
| 527 | N-benzyl-4-({[(3-chlorophenyl)sulfonyl][(3R)-2-oxoazepan-3-yl]amino}methyl)benzamide | 526.0 | — |
| 528 | N-benzyl-4-({[(3,4-difluorophenyl)sulfonyl][(3R)-2-oxoazepan-3-yl]amino}methyl)benzamide | 528.0 | — |
| 529 | N-benzyl-4-({[(3-chloro-4-fluorophenyl)sulfonyl][(3R)-2-oxoazepan-3-yl]amino}methyl)benzamide | 544.0 | — |
| 530 | N-benzyl-4-({[(4-fluorophenyl)sulfonyl][(3R)-2-oxoazepan-3-yl]amino}methyl)benzamide | 510.0 | — |
| 531 | 4-({[(3,5-difluorophenyl)sulfonyl][(3R)-2-oxoazepan-3-yl]amino}methyl)benzamide | 438.0 | — |
| 532 | 4-({[(3-chlorophenyl)sulfonyl][(3R)-2-oxoazepan-3-yl]amino}methyl)benzamide | 436.0 | — |
| 533 | 4-({[(4-chlorophenyl)sulfonyl][(3R)-2-oxoazepan-3-yl]amino}methyl)benzoic acid | 437.0 | — |
| 534 | 4-({[(4-chlorophenyl)sulfonyl][(3R)-2-oxoazepan-3-yl]amino}methyl)benzamide | 436.0 | — |
| 535 | 4-({[(4-chlorophenyl)sulfonyl][(3R)-2-oxoazepan-3-yl]amino}methyl)-N-[(1S)-1-phenylethyl]benzamide | 540.0 | — |
| 536 | 4-({[(4-chlorophenyl)sulfonyl][(3R)-2-oxoazepan-3-yl]amino}methyl)-N-[(1S,2R)-2-hydroxy-1-methyl-2-phenylethyl]benzamide | 570.0 | — |
| 537 | 4-({[(4-chlorophenyl)sulfonyl][(3R)-2-oxoazepan-3-yl]amino}methyl)-N-[(1R)-1-phenylethyl]benzamide | 540.0 | — |
| 538 | N-(3-chloro-2,6-difluorobenzyl)-4-({[(4-chlorophenyl)sulfonyl][(3R)-2-oxoazepan-3-yl]amino}methyl)benzamide | 596.0 | — |
| 539 | 4-({[(4-chlorophenyl)sulfonyl][(3R)-2-oxoazepan-3-yl]amino}methyl)-N-(1-naphthylmethyl)benzamide | 576.0 | — |
| 540 | 4-chloro-N-{4-[(3-methylpiperazin-1-yl)carbonyl]benzyl}-N-[(3R)-2-oxoazepan-3-yl]benzenesulfonamide | 519.0 | — |
| 541 | N-(1-benzylpiperidin-3-yl)-4-({[(4-chlorophenyl)sulfonyl][(3R)-2-oxoazepan-3-yl]amino}methyl)benzamide | 609.2 | — |
| 542 | 4-({[(4-chlorophenyl)sulfonyl][(3R)-2-oxoazepan-3-yl]amino}methyl)-N-(4-isopropylbenzyl)benzamide | 568.0 | — |
| 543 | 4-({[(4-chlorophenyl)sulfonyl][(3R)-2-oxoazepan-3-yl]amino}methyl)-N-(2-hydroxy-1-methylethyl)benzamide | 494.0 | — |
| 544 | 4-({[(4-chlorophenyl)sulfonyl][(3R)-2-oxoazepan-3-yl]amino}methyl)-N-(1-pyridin-4-ylethyl)benzamide | 541.0 | — |
| 545 | 4-({[(4-chlorophenyl)sulfonyl][(3R)-2-oxoazepan-3-yl]amino}methyl)-N-(4-fluorobenzyl)benzamide | 544.0 | — |
| 546 | 4-({[(4-chlorophenyl)sulfonyl][(3R)-2-oxoazepan-3-yl]amino}methyl)-N-(2,5-dimethoxybenzyl)benzamide | 586.0 | — |
| 547 | 4-({[(4-chlorophenyl)sulfonyl][(3R)-2-oxoazepan-3-yl]amino}methyl)-N-piperidin-3-ylbenzamide | 519.0 | — |
| 548 | 4-({[(4-chlorophenyl)sulfonyl][(3R)-2-oxoazepan-3-yl]amino}methyl)-N-(pyrazin-2-ylmethyl)benzamide | 528.0 | — |
| 549 | 4-({[(4-chlorophenyl)sulfonyl][(3R)-2-oxoazepan-3-yl]amino}methyl)-N-(3,5-dimethylbenzyl)benzamide | 554.0 | — |
| 550 | 4-({[(4-chlorophenyl)sulfonyl][(3R)-2-oxoazepan-3-yl]amino}methyl)-N-(2,6-dichlorobenzyl)benzamide | 594.0 | — |
| 551 | N-(5-chloro-2-methylbenzyl)-4-({[(4-chlorophenyl)sulfonyl][(3R)-2-oxoazepan-3-yl]amino}methyl)benzamide | 574.0 | — |
| 552 | 4-({[(4-chlorophenyl)sulfonyl][(3R)-2-oxoazepan-3-yl]amino}methyl)-N-[(1S)-1-phenylpropyl]benzamide | 554.0 | — |
| 553 | 4-({[(4-chlorophenyl)sulfonyl][(3R)-2-oxoazepan-3-yl]amino}methyl)-N-[(1R)-1-phenylpropyl]benzamide | 554.0 | — |
| 554 | 4-({[(4-chlorophenyl)sulfonyl][(3R)-2-oxoazepan-3-yl]amino}methyl)-N-(3-methylbenzyl)benzamide | 540.0 | — |
| 555 | N-[(3R)-1-azabicyclo[2.2.2]oct-3-yl]-4-({[(4-chlorophenyl)sulfonyl][(3R)-2-oxoazepan-3-yl]amino}methyl)benzamide | 545.0 | — |
| 556 | 4-({[(4-chlorophenyl)sulfonyl][(3R)-2-oxoazepan-3-yl]amino}methyl)-N-[3-(trifluoromethoxy)benzyl]benzamide | 610.0 | — |
| 557 | N-(biphenyl-3-ylmethyl)-4-({[(4-chlorophenyl)sulfonyl][(3R)-2-oxoazepan-3-yl]amino}methyl)benzamide | 602.0 | — |
| 558 | 4-({[(4-chlorophenyl)sulfonyl][(3R)-2-oxoazepan-3-yl]amino}methyl)-N-[(5-methyl-2-furyl)methyl]benzamide | 530.0 | — |
| 559 | 4-({[(4-chlorophenyl)sulfonyl][(3R)-2-oxoazepan-3-yl]amino}methyl)-N-[4-(1H-pyrazol-1-yl)benzyl]benzamide | 592.0 | — |
| 560 | 4-({[(4-chlorophenyl)sulfonyl][(3R)-2-oxoazepan-3-yl]amino}methyl)-N-[4-(methylthio)benzyl]benzamide | 572.0 | — |
| 561 | 4-({[(4-chlorophenyl)sulfonyl][(3R)-2-oxoazepan-3-yl]amino}methyl)-N-[(1S)-1,2,3,4-tetrahydronaphthalen-1-yl]benzamide | 566.0 | — |
| 562 | 4-({[(4-chlorophenyl)sulfonyl][(3R)-2-oxoazepan-3-yl]amino}methyl)-N-(2,5-dimethylbenzyl)benzamide | 554.0 | — |
| 563 | N-[(1R)-1-(3-bromophenyl)ethyl]-4-({[(4-chlorophenyl)sulfonyl][(3R)-2-oxoazepan-3-yl]amino}methyl)benzamide | 620.0 | — |
| 564 | 4-({[(4-chlorophenyl)sulfonyl][(3R)-2-oxoazepan-3-yl]amino}methyl)-N-[(1S)-1-(4-methoxyphenyl)ethyl]benzamide | 570.0 | — |
| 565 | 4-({[(4-chlorophenyl)sulfonyl][(3R)-2-oxoazepan-3-yl]amino}methyl)-N-[(1S)-1-(3-methoxyphenyl)ethyl]benzamide | 570.0 | — |

-continued

| Cmpnd. No. | Name | M + H | M + Na |
|---|---|---|---|
| 566 | 4-({[(4-chlorophenyl)sulfonyl][(3R)-2-oxoazepan-3-yl]amino}methyl)-N-[(1S)-2,3-dihydro-1H-inden-1-yl]benzamide | 552.0 | — |
| 567 | 4-({[(4-chlorophenyl)sulfonyl][(3R)-2-oxoazepan-3-yl]amino}methyl)-N-(2-cyanoethyl)-N-cyclopropylbenzamide | 529.0 | — |
| 568 | N-[(3S)-1-azabicyclo[2.2.2]oct-3-yl]-4-({[(4-chlorophenyl)sulfonyl][(3R)-2-oxoazepan-3-yl]amino}methyl)benzamide | 545.0 | — |
| 569 | N-(3-chloro-2-methylbenzyl)-4-({[(4-chlorophenyl)sulfonyl][(3R)-2-oxoazepan-3-yl]amino}methyl)benzamide | 574.0 | — |
| 570 | 4-({[(4-chlorophenyl)sulfonyl][(3R)-2-oxoazepan-3-yl]amino}methyl)-N-(2,6-difluorobenzyl)benzamide | 562.0 | — |
| 571 | 4-({[(4-chlorophenyl)sulfonyl][(3R)-2-oxoazepan-3-yl]amino}methyl)-N-[(5-methylisoxazol-3-yl)methyl]benzamide | 531.0 | — |
| 572 | N-(1-benzothien-3-ylmethyl)-4-({[(4-chlorophenyl)sulfonyl][(3R)-2-oxoazepan-3-yl]amino}methyl)benzamide | 582.0 | — |
| 573 | 4-({[(4-chlorophenyl)sulfonyl][(3R)-2-oxoazepan-3-yl]amino}methyl)-N-(2,3-dichlorobenzyl)benzamide | 594.0 | — |
| 574 | 4-({[(4-chlorophenyl)sulfonyl][(3R)-2-oxoazepan-3-yl]amino}methyl)-N-[3-(1H-pyrrol-1-yl)benzyl]benzamide | 591.0 | — |
| 575 | 4-({[(4-chlorophenyl)sulfonyl][(3R)-2-oxoazepan-3-yl]amino}methyl)-N-(2-ethoxybenzyl)benzamide | 570.0 | — |
| 576 | N-(6-chloro-2-fluoro-3-methylbenzyl)-4-({[(4-chlorophenyl)sulfonyl][(3R)-2-oxoazepan-3-yl]amino}methyl)benzamide | 592.0 | — |
| 577 | 4-({[(4-chlorophenyl)sulfonyl][(3R)-2-oxoazepan-3-yl]amino}methyl)-N-methyl-N-[(1R)-1-phenylethyl]benzamide | 554.0 | — |
| 578 | N-(1-benzylpiperidin-4-yl)-4-({[(4-chlorophenyl)sulfonyl][(3R)-2-oxoazepan-3-yl]amino}methyl)benzamide | 609.0 | — |
| 579 | 4-({[(4-chlorophenyl)sulfonyl][(3R)-2-oxoazepan-3-yl]amino}methyl)-N-[2-(trifluoromethoxy)benzyl]benzamide | 610.0 | — |
| 580 | 4-({[(4-chlorophenyl)sulfonyl][(3R)-2-oxoazepan-3-yl]amino}methyl)-N-(2,3-dimethylbenzyl)benzamide | 554.0 | — |
| 581 | 4-({[(4-chlorophenyl)sulfonyl][(3R)-2-oxoazepan-3-yl]amino}methyl)-N-(2,5-difluorobenzyl)benzamide | 562.0 | — |
| 582 | N-(3-bromo-4-fluorobenzyl)-4-({[(4-chlorophenyl)sulfonyl][(3R)-2-oxoazepan-3-yl]amino}methyl)benzamide | 622.0 | — |
| 583 | 4-({[(4-chlorophenyl)sulfonyl][(3R)-2-oxoazepan-3-yl]amino}methyl)-N-[4-fluoro-3-(trifluoromethyl)benzyl]benzamide | 612.0 | — |
| 584 | N-(3-chloro-4-fluorobenzyl)-4-({[(4-chlorophenyl)sulfonyl][(3R)-2-oxoazepan-3-yl]amino}methyl)benzamide | 578.0 | — |
| 585 | N-[(1S,2S)-2-(benzyloxy)cyclopentyl]-4-({[(4-chlorophenyl)sulfonyl][(3R)-2-oxoazepan-3-yl]amino}methyl)benzamide | 610.0 | — |
| 586 | 4-({[(4-chlorophenyl)sulfonyl][(3R)-2-oxoazepan-3-yl]amino}methyl)-N-methyl-N-(pyridin-3-ylmethyl)benzamide | 541.0 | — |
| 587 | 4-({[(4-chlorophenyl)sulfonyl][(3R)-2-oxoazepan-3-yl]amino}methyl)-N-(3,4-dihydroxybenzyl)benzamide | 558.0 | — |
| 588 | 4-({[(4-chlorophenyl)sulfonyl][(3R)-2-oxoazepan-3-yl]amino}methyl)-N-(4-hydroxy-3-methoxybenzyl)benzamide | 572.0 | — |
| 589 | 4-({[(4-chlorophenyl)sulfonyl][(3R)-2-oxoazepan-3-yl]amino}methyl)-N-{[3-hydroxy-5-(hydroxymethyl)-2-methylpyridin-4-yl]methyl}benzamide | 587.0 | — |
| 590 | 4-({[(4-chlorophenyl)sulfonyl][(3R)-2-oxoazepan-3-yl]amino}methyl)-N-(3-fluorobenzyl)benzamide | 544.0 | — |
| 591 | 4-({[(4-chlorophenyl)sulfonyl][(3R)-2-oxoazepan-3-yl]amino}methyl)-N-[(1S,2S)-2-hydroxycyclohexyl]benzamide | 534.0 | — |
| 592 | 4-({[(4-chlorophenyl)sulfonyl][(3R)-2-oxoazepan-3-yl]amino}methyl)-N-(1,2,3,4-tetrahydronaphthalen-1-yl)benzamide | 566.0 | — |
| 593 | 4-({[(4-chlorophenyl)sulfonyl][(3R)-2-oxoazepan-3-yl]amino}methyl)-N-(pyridin-3-ylmethyl)benzamide | 527.0 | — |
| 594 | 4-({[(4-chlorophenyl)sulfonyl][(3R)-2-oxoazepan-3-yl]amino}methyl)-N-(pyridin-4-ylmethyl)benzamide | 527.0 | — |
| 595 | N-(2-chlorobenzyl)-4-({[(4-chlorophenyl)sulfonyl][(3R)-2-oxoazepan-3-yl]amino}methyl)benzamide | 560.0 | — |
| 596 | 4-({[(4-chlorophenyl)sulfonyl][(3R)-2-oxoazepan-3-yl]amino}methyl)-N-[(1R,2S)-2-hydroxy-2,3-dihydro-1H-inden-1-yl]benzamide | 568.0 | — |
| 597 | 4-({[(4-chlorophenyl)sulfonyl][(3R)-2-oxoazepan-3-yl]amino}methyl)-N-(2-methylbenzyl)benzamide | 540.0 | — |
| 598 | 4-({[(4-chlorophenyl)sulfonyl][(3R)-2-oxoazepan-3-yl]amino}methyl)-N-[(3R)-tetrahydrofuran-3-yl]benzamide | 506.0 | — |
| 599 | 4-({[(4-chlorophenyl)sulfonyl][(3R)-2-oxoazepan-3-yl]amino}methyl)-N-[(1R,6S)-6-(hydroxymethyl)cyclohex-3-en-1-yl]benzamide | 546.0 | — |
| 600 | 4-({[(4-chlorophenyl)sulfonyl][(3R)-2-oxoazepan-3-yl]amino}methyl)-N-[4-(trifluoromethyl)benzyl]benzamide | 594.0 | — |
| 601 | 4-({[(4-chlorophenyl)sulfonyl][(3R)-2-oxoazepan-3-yl]amino}methyl)-N-(3,4-dimethoxybenzyl)benzamide | 586.0 | — |
| 602 | 4-({[(4-chlorophenyl)sulfonyl][(3R)-2-oxoazepan-3-yl]amino}methyl)-N-[cyano(phenyl)methyl]benzamide | 551.0 | — |
| 603 | 4-({[(4-chlorophenyl)sulfonyl][(3R)-2-oxoazepan-3-yl]amino}methyl)-N-(3,5-dichlorobenzyl)benzamide | 594.0 | — |
| 604 | 4-({[(4-chlorophenyl)sulfonyl][(3R)-2-oxoazepan-3-yl]amino}methyl)-N-[4-(trifluoromethoxy)benzyl]benzamide | 610.0 | — |
| 605 | 4-({[(4-chlorophenyl)sulfonyl][(3R)-2-oxoazepan-3-yl]amino}methyl)-N-[4-(methylsulfonyl)benzyl]benzamide | 604.0 | — |
| 606 | 4-({[(4-chlorophenyl)sulfonyl][(3R)-2-oxoazepan-3-yl]amino}methyl)-N-(3,4-dichlorobenzyl)benzamide | 596.0 | — |
| 607 | N-(4-chlorobenzyl)-4-({[(4-chlorophenyl)sulfonyl][(3R)-2-oxoazepan-3-yl]amino}methyl)benzamide | 560.0 | — |
| 608 | 4-chloro-N-(4-{[(2S)-2-(hydroxymethyl)pyrrolidin-1-yl]carbonyl}benzyl)-N-[(3R)-2-oxoazepan-3-yl]benzenesulfonamide | 520.0 | — |
| 609 | 4-({[(4-chlorophenyl)sulfonyl][(3R)-2-oxoazepan-3-yl]amino}methyl)-N-cyclohexyl-N-ethylbenzamide | 546.2 | — |
| 610 | 4-chloro-N-(4-{[2-(hydroxymethyl)piperidin-1-yl]carbonyl}benzyl)-N-[(3R)-2-oxoazepan-3-yl]benzenesulfonamide | 534.0 | — |
| 611 | 4-chloro-N-[(3R)-2-oxoazepan-3-yl]-N-(4-{[(2S)-2-(pyrrolidin-1-ylmethyl)pyrrolidin-1-yl]carbonyl}benzyl)benzenesulfonamide | 573.2 | — |
| 612 | 1-[4-({[(4-chlorophenyl)sulfonyl][(3R)-2-oxoazepan-3-yl]amino}methyl)benzoyl]-L-prolinamide | 533.0 | — |
| 613 | 4-({[(4-chlorophenyl)sulfonyl][(3R)-2-oxoazepan-3-yl]amino}methyl)-N,N-bis(pyridin-3-ylmethyl)benzamide | 618.0 | — |
| 614 | 4-({[(4-chlorophenyl)sulfonyl][(3R)-2-oxoazepan-3-yl]amino}methyl)-N-[(1R,2S)-2-(hydroxymethyl)cyclohexyl]benzamide | 548.0 | — |
| 615 | N-[(1R,2S)-2-(aminocarbonyl)cyclohexyl]-4-({[(4-chlorophenyl)sulfonyl][(3R)-2-oxoazepan-3-yl]amino}methyl)benzamide | 561.0 | — |
| 616 | 3-{[4-({[(4-chlorophenyl)sulfonyl][(3R)-2-oxoazepan-3-yl]amino}methyl)benzoyl]amino}benzamide | 555.0 | — |
| 617 | 4-({[(4-chlorophenyl)sulfonyl][(3R)-2-oxoazepan-3-yl]amino}methyl)-N-(3-iodobenzyl)benzamide | 652.0 | — |
| 618 | 4-({[(4-chlorophenyl)sulfonyl][(3R)-2-oxoazepan-3-yl]amino}methyl)-N-(2-furylmethyl)-N-methylbenzamide | 530.0 | — |
| 619 | N-(1-benzylpyrrolidin-3-yl)-4-({[(4-chlorophenyl)sulfonyl][(3R)-2-oxoazepan-3-yl]amino}methyl)-N-ethylbenzamide | 623.0 | — |
| 620 | 4-({[(4-chlorophenyl)sulfonyl][(3R)-2-oxoazepan-3-yl]amino}methyl)-N-cyclohexyl-N-(2-hydroxyethyl)benzamide | 562.0 | — |
| 621 | 4-({[(4-chlorophenyl)sulfonyl][(3R)-2-oxoazepan-3-yl]amino}methyl)-N-[(5-hydroxy-4-oxo-4H-pyran-2-yl)methyl]benzamide | 560.0 | — |
| 622 | N-{[3-(4-chlorophenyl)isoxazol-5-yl]methyl}-4-({[(4-chlorophenyl)sulfonyl][(3R)-2-oxoazepan-3-yl]amino}methyl)benzamide | 627.0 | — |
| 623 | N-(4-chloro-2-methylbenzyl)-4-({[(4-chlorophenyl)sulfonyl][(3R)-2-oxoazepan-3-yl]amino}methyl)benzamide | — | 596.0 |
| 624 | N-[(1R,2R)-2-(benzyloxy)cyclopentyl]-4-({[(4-chlorophenyl)sulfonyl][(3R)-2-oxoazepan-3-yl]amino}methyl)benzamide | 610.0 | — |
| 625 | N-[(1R,2R)-2-(benzyloxy)cyclohexyl]-4-({[(4-chlorophenyl)sulfonyl][(3R)-2-oxoazepan-3-yl]amino}methyl)benzamide | 624.2 | — |
| 626 | 4-({[(4-chlorophenyl)sulfonyl][(3R)-2-oxoazepan-3-yl]amino}methyl)-N-isopropyl-N-(2-pyridin-4-ylethyl)benzamide | 583.0 | — |
| 627 | 4-({[(4-chlorophenyl)sulfonyl][(3R)-2-oxoazepan-3-yl]amino}methyl)-N-(2,2,2-trifluoroethyl)benzamide | 518.0 | — |
| 628 | 4-({[(4-chlorophenyl)sulfonyl][(3R)-2-oxoazepan-3-yl]amino}methyl)-N-[(1,5-dimethyl-1H-pyrrol-2-yl)methyl]benzamide | 543.0 | — |
| 629 | N-benzyl-4-({[(4-chlorophenyl)sulfonyl][(3R)-2-oxoazepan-3-yl]amino}methyl)-N-methylbenzamide | 540.0 | — |
| 630 | 4-({[(4-chlorophenyl)sulfonyl][(3R)-2-oxoazepan-3-yl]amino}methyl)-N-(2,3-dihydroxypropyl)-N-methylbenzamide | 524.0 | — |
| 631 | 4-({[(4-chlorophenyl)sulfonyl][(3R)-2-oxoazepan-3-yl]amino}methyl)-N-(2-hydroxyethyl)-N-methylbenzamide | 494.0 | — |
| 632 | 4-({[(4-chlorophenyl)sulfonyl][(3R)-2-oxoazepan-3-yl]amino}methyl)-N-(3-hydroxy-3-phenylpropyl)-N-methylbenzamide | 584.0 | — |
| 633 | 4-chloro-N-[4-(morpholin-4-ylcarbonyl)benzyl]-N-[(3R)-2-oxoazepan-3-yl]benzenesulfonamide | 506.0 | — |
| 634 | 4-chloro-N-{4-[(3-hydroxypyrrolidin-1-yl)carbonyl]benzyl}-N-[(3R)-2-oxoazepan-3-yl]benzenesulfonamide | 506.0 | — |
| 635 | N,N-diallyl-4-({[(4-chlorophenyl)sulfonyl][(3R)-2-oxoazepan-3-yl]amino}methyl)benzamide | 516.0 | — |
| 636 | 4-({[(4-chlorophenyl)sulfonyl][(3R)-2-oxoazepan-3-yl]amino}methyl)-N-(1-pyridin-3-ylethyl)benzamide | 541.0 | — |

-continued

| Cmpnd. No. | Name | M + H | M + Na |
|---|---|---|---|
| 637 | 4-({[(4-chlorophenyl)sulfonyl][(3R)-2-oxoazepan-3-yl]amino}methyl)-N-methyl-N-prop-2-yn-1-ylbenzamide | 488.0 | — |
| 638 | 4-({[(4-chlorophenyl)sulfonyl][(3R)-2-oxoazepan-3-yl]amino}methyl)-N-(2-methoxyethyl)-N-propylbenzamide | 536.0 | — |
| 639 | 4-({[(4-chlorophenyl)sulfonyl][(3R)-2-oxoazepan-3-yl]amino}methyl)-N-methyl-N-propylbenzamide | 492.0 | — |
| 640 | 4-({[(4-chlorophenyl)sulfonyl][(3R)-2-oxoazepan-3-yl]amino}methyl)-N-isopropyl-N-methylbenzamide | 492.0 | — |
| 641 | 4-({[(4-chlorophenyl)sulfonyl][(3R)-2-oxoazepan-3-yl]amino}methyl)-N-(1,4-dioxan-2-ylmethyl)benzamide | 536.0 | — |
| 642 | 4-({[(4-chlorophenyl)sulfonyl][(3R)-2-oxoazepan-3-yl]amino}methyl)-N-[(3-methylpyridin-2-yl)methyl]benzamide | 541.0 | — |
| 643 | 4-({[(4-chlorophenyl)sulfonyl][(3R)-2-oxoazepan-3-yl]amino}methyl)-N-{[(2R)-1-ethylpyrrolidin-2-yl]methyl}benzamide | 547.0 | — |
| 644 | 4-({[(4-chlorophenyl)sulfonyl][(3R)-2-oxoazepan-3-yl]amino}methyl)-N-methyl-N-(1-methylpyrrolidin-3-yl)benzamide | 533.0 | — |
| 645 | 4-({[(4-chlorophenyl)sulfonyl][(3R)-2-oxoazepan-3-yl]amino}methyl)-N-[(3-methyl-2-thienyl)methyl]benzamide | 546.0 | — |
| 646 | 4-({[(4-chlorophenyl)sulfonyl][(3R)-2-oxoazepan-3-yl]amino}methyl)-N-[(1,3,5-trimethyl-1H-pyrazol-4-yl)methyl]benzamide | 558.0 | — |
| 647 | 4-({[(4-chlorophenyl)sulfonyl][(3R)-2-oxoazepan-3-yl]amino}methyl)-N-[(2,5-dimethyl-3-furyl)methyl]benzamide | 544.0 | — |
| 648 | 4-({[(4-chlorophenyl)sulfonyl][(3R)-2-oxoazepan-3-yl]amino}methyl)-N-(3-furylmethyl)benzamide | 516.0 | — |
| 649 | 4-chloro-N-(4-fluoro-3-nitrobenzyl)-N-[(3R)-2-oxoazepan-3-yl]benzenesulfonamide | 456.0 | — |
| 650 | 4-({[(4-chlorophenyl)sulfonyl][(3R)-2-oxoazepan-3-yl]amino}methyl)-N-{1-[4-(methylsulfonyl)phenyl]ethyl}benzamide | 618.0 | — |
| 651 | 4-({[(4-chlorophenyl)sulfonyl][(3R)-2-oxoazepan-3-yl]amino}methyl)-N-[1-(4-fluorophenyl)ethyl]benzamide | 558.0 | — |
| 652 | 4-chloro-N-(4-cyanobenzyl)-N-[(3R)-2-oxoazepan-3-yl]benzenesulfonamide | 418.0 | — |
| 653 | 4-chloro-N-[4-(chloromethyl)benzyl]-N-[(3R)-2-oxoazepan-3-yl]benzenesulfonamide | 441.0 | — |
| 654 | 4-chloro-N-[(3R)-2-oxoazepan-3-yl]-N-{4-[(2-phenylpyrrolidin-1-yl)carbonyl]benzyl}benzenesulfonamide | 566.0 | — |
| 655 | 4-chloro-N-[4-(2,3-dihydro-1H-indol-1-ylcarbonyl)benzyl]-N-[(3R)-2-oxoazepan-3-yl]benzenesulfonamide | 538.0 | — |
| 656 | 4-chloro-N-{4-[(2-methylpyrrolidin-1-yl)carbonyl]benzyl}-N-[(3R)-2-oxoazepan-3-yl]benzenesulfonamide | 504.0 | — |
| 657 | 4-chloro-N-{4-[(2-ethylpyrrolidin-1-yl)carbonyl]benzyl}-N-[(3R)-2-oxoazepan-3-yl]benzenesulfonamide | 518.0 | — |

The following compounds can be prepared essentially according to the methods and procedures described above.

| Cmpnd. No. | Name | M + H | M + Na |
|---|---|---|---|
| 658 | 4-chloro-N-[(1-isopropyl-1H-1,2,3-benzotriazol-5-yl)methyl]-N-[(3R)-2-oxoazepan-3-yl]benzenesulfonamide | 476 | — |

-continued

| Cmpnd. No. | Name | M + H | M + Na |
|---|---|---|---|
| 659 | 4-chloro-N-(1,3-dihydro-2,1,3-benzothiadiazol-5-ylmethyl)-N-[(3R)-2-oxoazepan-3-yl]benzenesulfonamide | 451 | — |

The following compounds can be prepared essentially according to the methods and procedures described above.

| Cmpnd No. | Name | M + H | M + Na |
|---|---|---|---|
| 660 | 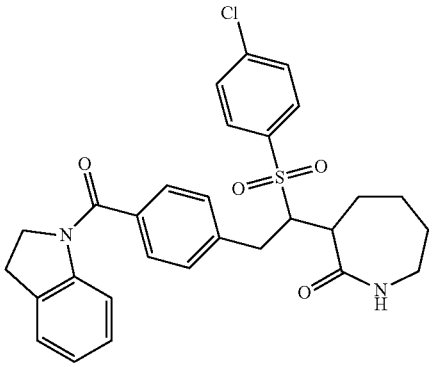  4-Chloro-N-[4-(2,3-dihydro-indole-1-carbonyl)-benzyl]-N-[(3R)-2-oxo-azepan-3-yl]-benzenesulfonamide | 538.0 | — |
| 661 | 4-Chloro-N-[4-(2-methyl-pyrrolidine-1-carbonyl)-benzyl]-N-[(3R)-2-oxo-azepan-3-yl]-benzenesulfonamide | 504.0 | — |
| 662 | 4-Chloro-N-[4-(2-ethyl-pyrrolidine-1-carbonyl)-benzyl]-N-[(3R)-2-oxo-azepan-3-yl]-benzenesulfonamide | 518.0 | — |
| 663 | 4-Chloro-N-[(3R)-2-oxo-azepan-3-yl]-N-[4-(1H-tetrazol-5-yl)-benzyl]-benzenesulfonamide | 461.0 | — |

| Cmpnd No. | Name | M + H | M + Na |
|---|---|---|---|
| 664 | 4-Chloro-N-[(3R)-2-oxo-azepan-3-yl]-N-[4-(3-pyridin-2-yl-[1,2,4]oxadiazol-5-yl)-benzyl]-benzenesulfonamide | 538.0 | — |
| 665 | 4-Chloro-N-[(3R)-2-oxo-azepan-3-yl]-N-[4-(3-pyridin-4-yl-[1,2,4]oxadiazol-5-yl)-benzyl]-benzenesulfonamide | 538.0 | — |
| 666 | 4-Chloro-N-[(3R)-2-oxo-azepan-3-yl]-N-{4-[3-(4-trifluoromethyl-phenyl)-[1,2,4]oxadiazol-5-yl]-benzyl}-benzenesulfonamide | 605.0 | — |
| 667 | 4-Chloro-N-[(3R)-2-oxo-azepan-3-yl]-N-[4-(3-p-tolyl-[1,2,4]oxadiazol-5-yl)-benzyl]-benzenesulfonamide | 551.0 | — |
| 668 | 4-Chloro-N-{4-[3-(4-fluoro-phenyl)-[1,2,4]oxadiazol-5-yl]-benzyl}-N-[(3R)-2-oxo-azepan-3-yl]-benzenesulfonamide | 555.0 | — |
| 669 | 4-Chloro-N-[(3R)-2-oxo-azepan-3-yl]-N-[4-(3-phenyl-[1,2,4]oxadiazol-5-yl)-benzyl]-benzenesulfonamide | 537.0 | — |
| 670 | 4-Chloro-N-{4-[5-(3-methoxy-phenyl)-[1,3,4]oxadiazol-2-yl]-benzyl}-N-[(3R)-2-oxo-azepan-3-yl]-benzenesulfonamide | 567.0 | — |
| 671 | 4-Chloro-N-{4-[5-(4-hydroxy-phenyl)-[1,3,4]oxadiazol-2-yl]-benzyl}-N-[(3R)-2-oxo-azepan-3-yl]-benzenesulfonamide | 553.0 | — |
| 672 | 4-Chloro-N-[(3R)-2-oxo-azepan-3-yl]-N-[4-(5-phenyl-[1,3,4]oxadiazol-2-yl)benzyl]-benzenesulfonamide | 537.0 | — |
| 673 | 4-Chloro-N-{4-[5-(4-methoxy-phenyl)-[1,3,4]oxadiazol-2-yl]-benzyl}-N-[(3R)-2-oxo-azepan-3-yl]-benzenesulfonamide | 567.0 | — |
| 674 | 4-Chloro-N-{4-[5-(2-methoxy-phenyl)-[1,3,4]oxadiazol-2-yl]-benzyl}-N-[(3R)-2-oxo-azepan-3-yl]-benzenesulfonamide | 567.0 | — |
| 675 | 4-Chloro-N-[(3R)-2-oxo-azepan-3-yl]-N-[4-(5-m-tolyl-[1,3,4]oxadiazol-2-yl)-benzyl]-benzenesulfonamide | 551.0 | — |
| 676 | N-[4-(5-Benzyl-[1,3,4]oxadiazol-2-yl)-benzyl]-4-chloro-N-[(3R)-2-oxo-azepan-3-yl]-benzenesulfonamide | 551.0 | — |
| 677 | 4-Chloro-N-[(3R)-2-oxo-azepan-3-yl]-N-[4-(5-pyridin-4-yl-[1,3,4]oxadiazol-2-yl)-benzyl]-benzenesulfonamide | 538.0 | — |
| 678 | 4-Chloro-N-[4-(5-furan-2-yl-[1,3,4]oxadiazol-2-yl)-benzyl]-N-[(3R)-2-oxo-azepan-3-yl]-benzenesulfonamide | 527.0 | — |
| 679 | 4-Chloro-N-{4-[5-(2,5-dichloro-phenyl)-[1,3,4]oxadiazol-2-yl]-benzyl}-N-(3R)-2-oxo-azepan-3-yl)-benzenesulfonamide | 606.0 | — |
| 680 | 4-Chloro-N-{4-[5-(4-chloro-phenyl)-[1,3,4]oxadiazol-2-yl]-benzyl}-N-[(3R)-2-oxo-azepan-3-yl]-benzenesulfonamide | 571.0 | — |
| 681 | 4-Chloro-N-[(3R)-2-oxo-azepan-3-yl]-N-[4-(5-pyridin-3-yl-[1,3,4]oxadiazol-2-yl)-benzyl]-benzenesulfonamide | 538.0 | — |
| 682 | 4-Chloro-N-[(3R)-2-oxo-azepan-3-yl]-N-[4-(5-propyl-[1,3,4]oxadiazol-2-yl)-benzyl]-benzenesulfonamide | 503.0 | — |

-continued

| Cmpnd No. | Name | M + H | M + Na |
|---|---|---|---|
| 683 | 4-Chloro-N-{4-[5-(3-methyl-3H-imidazol-4-yl)-[1,3,4]oxadiazol-2-yl]-benzyl}-N-[(3R)-2-oxo-azepan-3-yl]-benzenesulfonamide | 541.0 | — |
| 684 | 4-Chloro-N-[4-(5-methoxymethyl-[1,3,4]oxadiazol-2-yl)-benzyl]-N-[(3R)-2-oxo-azepan-3-yl]-benzenesulfonamide | 505.0 | — |
| 685 | N-[4-(5-Butyl-[1,3,4]oxadiazol-2-yl)-benzyl]-4-chloro-N-[(3R)-2-oxo-azepan-3-yl]-benzenesulfonamide | 517.0 | — |
| 686 | 4-Chloro-N-{4-[5-(5-methyl-thiophen-2-yl)-[1,3,4]oxadiazol-2-yl]-benzyl}-N-[(3R)-2-oxo-azepan-3-yl]-benzenesulfonamide | 557.0 | — |
| 687 | 4-Chloro-N-[4-(5-isopropyl-[1,3,4]oxadiazol-2-yl)-benzyl]-N-[(3R)-2-oxo-azepan-3-yl]-benzenesulfonamide | 503.0 | — |
| 688 | 4-Chloro-N-[(3R)-2-oxo-azepan-3-yl]-N-[4-(5-thiophen-3-yl-[1,3,4]oxadiazol-2-yl)-benzyl]-benzenesulfonamide | 543.0 | — |
| 689 | N-[4-(5-tert-Butyl-[1,3,4]oxadiazol-2-yl)-benzyl]-4-chloro-N-[(3R)-2-oxo-azepan-3-yl]-benzenesulfonamide | 517.0 | — |
| 690 | 4-Chloro-N-[4-(5-cyclohexyl-[1,3,4]oxadiazol-2-yl)-benzyl]-N-[(3R)-2-oxo-azepan-3-yl]-benzenesulfonamide | 543.0 | — |

Notch Signaling Assay for Selective Inhibitors of Gamma Secretase.

A convergence of evidence indicates that the gamma secretase complex, comprised of the presenilin subunits, mediates the intra-membrane cleavage of Amyloid precursor protein (APP), and the Notch family of proteins (De Strooper, B., P. Saftig, K. Craessaerts, H. Vanderstichele, G. Guhde, W. Annaert, K. Von Figura and F. Van Leuven (1998). "Deficiency of presenilin-1 inhibits the normal cleavage of amyloid precursor protein." Nature 391(6665): 387-90; De Strooper, B., W. Annaert, P. Cupers, P. Saftig, K. Craessaerts, J. S. Mumm, E. H. Schroeter, V. Schrijvers, M. S. Wolfe, W. J. Ray et al. (1999). "A presenilin-1-dependent gamma-secretase-like protease mediates release of Notch intracellular domain." Nature 398(6727): 518-22; Mumm, J. S., E. H. Schroeter, M. T. Saxena, A. Griesemer, X. Tian, D. J. Pan, W. J. Ray and R. Kopan (2000). "A ligand-induced extracellular cleavage regulates gamma-secretase-like proteolytic activation of Notch1." Mol Cell 5(2): 197-206; Zhang, Z., P. Nadeau, W. Song, D. Donoviel, M. Yuan, A. Bernstein and B. A. Yankner (2000). "Presenilins are required for gamma-secretase cleavage of beta-APP and transmembrane cleavage of Notch-1." Nat Cell Biol 2(7): 463-5). Cleavage of APP by gamma secretase leads to β-amyloid synthesis. Cleavage of Notch1 by gamma secretase results in release of the Notch intracellular domain (NICD), which translocates to the nucleus and activates gene expression (Jarriault, S., C. Brou, F. Logeat, E. H. Schroeter, R. Kopan and A. Israel (1995). "Signalling downstream of activated mammalian Notch." Nature 377(6547): 355-8; Kopan, R., E. H. Schroeter, H. Weintraub and J. S. Nye (1996). "Signal transduction by activated Notch: importance of proteolytic processing and its regulation by the extracellular domain." Proc Natl Acad Sci USA 93(4): 1683-8; Schroeter, E. H., J. A. Kisslinger and R. Kopan (1998). "Notch-1 signalling requires ligand-induced proteolytic release of intracellular domain." Nature 393(6683): 382-6). In particular, Notch signaling activates transcription of the mammalian homolog of the Drosophila transcription factor hairy-enhancer of split (Hes). Transcriptional activation of Hes1 is mediated by de-repression of CBF1/RBPJk upon binding by NICD in the nucleus. These facts have been exploited to develop a reporter gene assay for Notch Signaling Hsieh, J. J., T. Henkel, P. Salmon, E. Robey, M. G. Peterson and S. D. Hayward (1996). "Truncated mammalian Notch1 activates CBF1/RBPJk-repressed genes by a mechanism resembling that of Epstein-Barr virus EBNA2." Mol Cell Biol 16(3): 952-9; Lu, F. M. and S. E. Lux (1996). "Constitutively active human Notch1 binds to the transcription factor CBF1 and stimulates transcription through a promoter containing a CBF1-responsive element." Proc Natl Acad Sci USA 93(11): 5663-7).

Gamma secretase inhibitors have been observed to block NICD formation, and inhibit Notch signaling (De Strooper, B., W. Annaert, P. Cupers, P. Saftig, K. Craessaerts, J. S. Mumm, E. H. Schroeter, V. Schrijvers, M. S. Wolfe, W. J. Ray et al. (1999). "A presenilin-1-dependent gamma-secretase-like protease mediates release of Notch intracellular domain." Nature 398(6727): 518-22). Due to the importance of Notch signaling in cell fate determination, and tissue differentiation during both development and in the adult, inhibition of Notch signaling by gamma secretase inhibitors is postulated to be a limiting factor in their therapeutic utility. In order to identify selective gamma secretase inhibitors, testing herein employs a reporter gene based Notch signaling assay using a constitutively active rat Notch1 construct (ZEDN1) provided by Dr. Gerry Weinmaster, [University of California at Los Angeles (UCLA)] as described by Shawber, et al., Development 122 (12): 3765-73, (1996). "Notch signaling inhibits muscle cell differentiation through a CBF1-independent pathway." Development 122(12): 3765-73 in combination with the CBF1 repressible Luciferase reporter gene 4xwtCBF1Luc (Hsieh, J. J., et al., (1996). Mol Cell Biol 16(3): 952-9).

When 4xwtCBF1 Luciferase is co-transfected with NotchΔE (ZEDN1), γ-secretase cleavage of NotchΔE releases the Notch intracellular domain (NICD), which translocates to the nucleus and de-represses CBF1mediated transcriptional repression, leading to transcription of the Luciferase reporter gene. Luciferase activity is easily assayed in cell extracts using commercially available kits. The activity of the reporter gene is directly correlated with gamma secretase cleavage of NotchΔE, and as such, a reduction in Luciferase activity provides a convenient measure of inhibition of gamma secretase cleavage of NotchΔE. A comparison of the IC50 values of compounds for inhibition of Notch signaling versus inhibition of β-amyloid production in 293sw cells is employed to guide in the selection of compounds that have the desired property of potent inhibition of β-amyloid synthesis with minimal inhibition of Notch Signaling.

Compounds of the invention are active in the above assay. Representative compounds are: compounds 77, 157, 249, 269, 275, 537, and 593, which exhibit an $IC_{50}$ within the range of from about 0.1-25 nM; compounds 85, 136, 153, 163, 227, 486, 553, 636, and 663, which exhibit an $IC_{50}$ within the range of from about 25-100 nM; compounds 52, 66, 108, 145, 160, 505, 579, and 609, which exhibit an $IC_{50}$ within the range of from about 100-1000 nM; compounds 14, 89, 148, 206, 338, 613, and 672, which exhibit an $IC_{50}$ of >1000 nM.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:
1. A compound of the formula

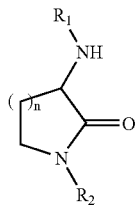

or a pharmaceutically acceptable salt thereof wherein
n is 1, 2, or 3;
$R_1$ is heteroaryl($C_1$-$C_6$)alkyl wherein the cyclic portion is substituted with 1, 2, 3, 4, or 5 groups that are independently halogen, $C_1$-$C_6$ alkyl, $C_1$-$C_6$ alkoxy, $C_1$-$C_4$ haloalkyl, $C_1$-$C_4$ haloalkoxy, aryl, arylalkyl, aryloxy, heteroaryl, —$SO_2$-aryl, —$S(O)_x$—$R_{25}$, —($C_1$-$C_4$ alkyl)-$S(O)_x$—$R_{25}$, CN, $C_1$-$C_6$ thioalkoxy, $C_1$-$C_6$ alkoxycarbonyl, —NR'R", —C(O)—NR'R", or heterocycloalkyl,
wherein the above aryl groups are optionally substituted with 1, 2, 3, or 4 groups that are independently halogen, $C_1$-$C_6$ alkyl, $C_1$-$C_6$ alkoxy, $C_1$-$C_4$ haloalkyl, or $C_1$-$C_4$ haloalkoxy;
wherein the above heteroaryl and heterocycloalkyl groups are optionally substituted with 1, 2, or 3 groups that are independently halogen, $CF_3$, ($C_1$-$C_4$) alkyl, $C_1$-$C_6$ thioalkoxy, OH, $C_1$-$C_4$ hydroxyalkyl, or $C_1$-$C_4$ alkoxy; or
$R_1$ is heterocycloalkyl ($C_1$-$C_6$ alkyl) wherein the heterocycloalkyl portion contains from 4-7 members and is optionally substituted with 1, 2, 3, 4, or 5 groups that are independently halogen, $C_1$-$C_6$ alkyl, $C_1$-$C_6$ alkoxy, $C_1$-$C_4$ haloalkyl, $C_1$-$C_4$ haloalkoxy, aryl, arylalkyl, aryloxy, heteroaryl, —$SO_2$-aryl, —$S(O)_x$—$R_{25}$, —($C_1$-$C_4$ alkyl)-$S(O)_x$—$R_{25}$, CN, $C_1$-$C_6$ thioalkoxy, $C_1$-$C_6$ alkoxycarbonyl, —NR'R", —C(O)—NR'R", heterocycloalkyl;
each x is independently 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), aryl, or heteroaryl; or
$R_{26}$, $R_{27}$ and the nitrogen to which they are attached form a heterocycloalkyl ring;
wherein R' at each occurrence is independently H, $C_1$-$C_6$ alkyl, aryl, aryl($C_1$-$C_4$)alkyl, $C_1$-$C_6$ alkanoyl, $C_3$-$C_6$ cycloalkyl, aryl($C_1$-$C_6$)alkanoyl, heterocycloalkyl, heteroaryl($C_1$-$C_4$)alkyl, —$SO_2$-alkyl, —$SO_2$-aryl, —$SO_2$-heteroaryl, heterocycloalkyl($C_1$-$C_6$)alkanoyl, or heteroaryl($C_1$-$C_6$)alkanoyl, wherein the alkyl portion of the alkyl and alkanoyl groups are optionally substituted with halogen or $C_1$-$C_6$ alkoxy,
wherein the aryl, and heteroaryl groups are optionally substituted with $C_1$-$C_6$ alkyl, $C_1$-$C_6$ alkoxy, halogen, $C_1$-$C_4$ haloalkyl, $C_1$-$C_4$ haloalkoxy;
wherein R" at each occurrence is independently H, or $C_1$-$C_6$ alkyl, wherein the alkyl group is optionally substituted with halogen; and
$R_2$ is H, $C_1$-$C_6$ alkyl, or phenyl($C_1$-$C_4$)alkyl.

2. A compound of the formula

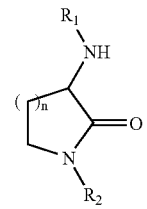

or a pharmaceutically acceptable salt thereof wherein
n is 1, 2, or 3;
$R_1$ is selected from the group consisting of thienyl($C_1$-$C_6$ alkyl), pyridyl($C_1$-$C_6$ alkyl), furanyl($C_1$-$C_6$ alkyl), pyrazolyl($C_1$-$C_6$ alkyl), pyrrolyl($C_1$-$C_6$ alkyl), thiazolyl($C_1$-$C_6$ alkyl), 1,2,3-thiadiazolyl($C_1$-$C_6$ alkyl), 1,2,4-thiadiazolyl($C_1$-$C_6$ alkyl), 1,3,4-oxadiazole ($C_1$-$C_6$ alkyl), 1,2,4-oxadiazole($C_1$-$C_6$ alkyl), indolyl ($C_1$-$C_6$ alkyl), triazolyl($C_1$-$C_6$ alkyl), isoxazolyl($C_1$-$C_6$ alkyl), benzothienyl($C_1$-$C_6$ alkyl), benzofuranyl ($C_1$-$C_6$ alkyl), quinolinyl($C_1$-$C_6$ alkyl), imidazo[2,1-b]thiazolyl($C_1$-$C_6$ alkyl), benzo[c][1,2,5]thiadiazolyl ($C_1$-$C_6$ alkyl), benzimidazolyl($C_1$-$C_6$ alkyl), benzoxazolyl($C_1$-$C_6$ alkyl), benzo[1,2,5]oxadiazolyl ($C_1$-$C_6$ alkyl), 1H-indazolyl($C_1$-$C_6$ alkyl), 1H-benzotriazolyl($C_1$-$C_6$ alkyl), furo[3,2-b]pyridinyl($C_1$-$C_6$ alkyl), 1H-pyrazolo[3,4-b]pyridinyl($C_1$-$C_6$ alkyl), 1H-pyrazolo[3,4-c]pyridinyl($C_1$-$C_6$ alkyl), quinoxalinyl($C_1$-$C_6$ alkyl), and isoquinolinyl($C_1$-$C_6$ alkyl), where
the heteroaryl portion of each is optionally substituted with 1, 2, 3, 4, or 5 groups that are independently halogen, $C_1$-$C_6$ alkyl, $C_1$-$C_6$ alkoxy, $C_1$-$C_4$ haloalkyl, $C_1$-$C_4$ haloalkoxy, aryl, arylalkyl, aryloxy, heteroaryl, —$SO_2$-aryl, —$S(O)_x$—$R_{25}$, —($C_1$-$C_4$ alkyl)-$S(O)_x$—$R_{25}$, CN, $C_1$-$C_6$ thioalkoxy, $C_1$-$C_6$ alkoxycarbonyl, —NR'R", —C(O)—NR'R", or heterocycloalkyl,
wherein the above aryl groups are optionally substituted with 1, 2, 3, or 4 groups that are independently halogen, $C_1$-$C_6$ alkyl, $C_1$-$C_6$ alkoxy, $C_1$-$C_4$ haloalkyl, or $C_1$-$C_4$ haloalkoxy, or CN;

wherein the above heteroaryl and heterocycloalkyl groups are optionally substituted with 1, 2, or 3 groups that are independently halogen, $CF_3$, ($C_1$-$C_4$)alkyl, $C_1$-$C_6$ thioalkoxy, OH, $C_1$-$C_4$ hydroxyalkyl, or $C_1$-$C_4$ alkoxy;

R' is H, $C_1$-$C_6$ alkyl, $C_3$-$C_8$ cycloalkyl, phenyl, phenyl($C_1$-$C_4$)alkyl, $C_1$-$C_6$ alkanoyl, phenyl($C_1$-$C_6$)alkanoyl, pyridyl($C_1$-$C_4$)alkyl, pyrimidyl($C_1$-$C_4$)alkyl, pyridazyl($C_1$-$C_4$)alkyl, pyrazinyl($C_1$-$C_4$)alkyl, thienyl($C_1$-$C_4$)alkyl, oxazolyl($C_1$-$C_4$)alkyl, thiazolyl($C_1$-$C_4$)alkyl, furanyl($C_1$-$C_4$)alkyl, piperidinyl($C_1$-$C_4$)alkyl, —$SO_2$-alkyl, —$SO_2$-phenyl, —$SO_2$-pyridyl, —$SO_2$-pyrimidyl, —$SO_2$-pyridazyl, —$SO_2$-pyrazinyl, —$SO_2$-thienyl, —$SO_2$-oxazolyl, —$SO_2$-thiazolyl, —$SO_2$-furanyl, pyridyl($C_1$-$C_6$)alkanoyl, pyrimidyl($C_1$-$C_6$)alkanoyl, pyridazyl($C_1$-$C_6$)alkanoyl, pyrazinyl($C_1$-$C_6$)alkanoyl, thienyl($C_1$-$C_6$)alkanoyl, oxazolyl($C_1$-$C_6$)alkanoyl, thiazolyl($C_1$-$C_6$)alkanoyl, or furanyl($C_1$-$C_6$)alkanoyl, wherein the alkyl portion of the alkyl and alkanoyl groups are optionally substituted with halogen or $C_1$-$C_6$ alkoxy, wherein the aryl, and heteroaryl groups are optionally substituted with alkyl, alkoxy, halogen, haloalkyl, haloalkoxy;

R" is H, or $C_1$-$C_6$ alkyl, wherein the alkyl group is optionally substituted with halogen;

each x is independently 0, 1, or 2;

$R_{25}$ is $C_1$-$C_6$ alkyl, OH, $NR_{26}R_{27}$;

$R_{26}$ and $R_{27}$ are independently H, $C_1$-$C_6$ alkyl, phenyl ($C_1$-$C_4$ alkyl), aryl, or heteroaryl; or $R_{26}$, $R_{27}$ and the nitrogen to which they are attached form a heterocycloalkyl ring; and $R_2$ is H, $C_1$-$C_6$ alkyl, or phenyl($C_1$-$C_4$)alkyl.

3. A compound of the formula

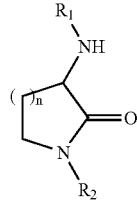

or a pharmaceutically acceptable salt thereof wherein n is 1, 2, or 3;

$R_1$ is heteroaryl($C_1$-$C_6$)alkyl wherein the cyclic portion is optionally substituted with 1, 2, 3, 4, or 5 groups that are independently halogen, $C_1$-$C_6$ alkyl, $C_1$-$C_6$ alkoxy, $C_1$-$C_4$ haloalkyl, $C_1$-$C_4$ haloalkoxy, aryl, arylalkyl, aryloxy, heteroaryl, —$SO_2$-aryl, —S(O)$_x$—$R_{25}$, —($C_1$-$C_4$ alkyl)-S(O)$_x$—$R_{25}$, CN, $C_1$-$C_6$ thioalkoxy, $C_1$-$C_6$ alkoxycarbonyl, —NR'R", —C(O)—NR'R", or heterocycloalkyl, wherein the above aryl groups are optionally substituted with 1, 2, 3, or 4 groups that are independently halogen, $C_1$-$C_6$ alkyl, $C_1$-$C_6$ alkoxy, $C_1$-$C_4$ haloalkyl, $C_4$ haloalkoxy, or CN;

wherein the above heteroaryl and heterocycloalkyl groups are optionally substituted with 1, 2, or 3 groups that are independently halogen, $CF_3$, ($C_1$-$C_4$) alkyl, $C_1$-$C_6$ thioalkoxy, OH, $C_1$-$C_4$ hydroxyalkyl, or $C_1$-$C_4$ alkoxy; or wherein R' at each occurrence is independently H, $C_1$-$C_6$ alkyl, aryl, aryl($C_1$-$C_4$)alkyl, $C_1$-$C_6$ alkanoyl, $C_3$-$C_6$ cycloalkyl, aryl($C_1$-$C_6$)alkanoyl, heterocycloalkyl, heteroaryl($C_1$-$C_4$)alkyl, —$SO_2$-alkyl, —$SO_2$-aryl, —$SO_2$-heteroaryl, heterocycloalkyl($C_1$-$C_6$)alkanoyl, or heteroaryl($C_1$-$C_6$)alkanoyl, wherein the alkyl portion of the alkyl and alkanoyl groups are optionally substituted with halogen or $C_1$-$C_6$ alkoxy, wherein the aryl, and heteroaryl groups are optionally substituted with $C_1$-$C_6$ alkyl, $C_1$-$C_6$ alkoxy, halogen, $C_1$-$C_4$ haloalkyl, $C_1$-$C_4$ haloalkoxy;

wherein R" at each occurrence is independently H, or $C_1$-$C_6$ alkyl, wherein the alkyl group is optionally substituted with halogen;

each x is independently 0, 1, or 2;

$R_{25}$ is $C_1$-$C_6$ alkyl, OH, $NR_{26}R_{27}$;

$R_{26}$ and $R_{27}$ are independently H, $C_1$-$C_6$ alkyl, phenyl ($C_1$-$C_4$ alkyl), aryl, or heteroaryl; or $R_{26}$, $R_{27}$ and the nitrogen to which they are attached form a heterocycloalkyl ring; and $R_2$ is H or $C_1$-$C_6$ alkyl.

4. A compound of the formula

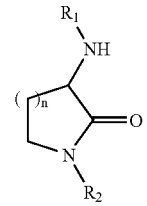

or a pharmaceutically acceptable salt thereof wherein n is 1, 2, or 3;

$R_1$ is heteroaryl($C_1$-$C_6$)alkyl wherein the cyclic portion is substituted with 1, 2, 3, 4, or 5 groups that are independently halogen, $C_1$-$C_6$ alkyl, $C_1$-$C_6$ alkoxy, $C_1$-$C_4$ haloalkyl, $C_1$-$C_4$ haloalkoxy, aryl, aryloxy, heteroaryl, —$SO_2$-aryl, —S(O)$_x$—$R_{25}$, —($C_1$-$C_4$ alkyl)-S(O)$_x$—$R_{25}$, CN, $C_1$-$C_6$ thioalkoxy, $C_1$-$C_6$ alkoxycarbonyl, —NR'R", —C(O)—NR'R", or heterocycloalkyl, wherein the above aryl groups are optionally substituted with 1, 2, 3, or 4 groups that are independently halogen, $C_1$-$C_6$ alkyl, $C_1$-$C_6$ alkoxy, $C_1$-$C_4$ haloalkyl, or $C_1$-$C_4$ haloalkoxy, or CN;

wherein the above heteroaryl and heterocycloalkyl groups are optionally substituted with 1, 2, or 3 groups that are independently halogen, $CF_3$, ($C_1$-$C_4$) alkyl, $C_1$-$C_6$ thioalkoxy, OH, $C_1$-$C_4$ hydroxyalkyl, or $C_1$-$C_4$ alkoxy; or wherein R' is H, $C_1$-$C_6$ alkyl, or $C_1$-$C_6$ alkanoyl, wherein the alkyl portion of the alkyl and alkanoyl groups are optionally substituted with halogen;

wherein R" is H, or $C_1$-$C_6$ alkyl, wherein the alkyl group is optionally substituted with halogen;

each x is independently 0, 1, or 2;

$R_{25}$ is $C_1$-$C_6$ alkyl, OH, $NR_{26}R_{27}$;

$R_{26}$ and $R_{27}$ are independently H, $C_1$-$C_6$ alkyl, phenyl ($C_1$-$C_4$ alkyl), aryl, or heteroaryl; or $R_{26}$, $R_{27}$ and the nitrogen to which they are attached form a heterocycloalkyl ring; and $R_2$ is H, $C_1$-$C_6$ alkyl, or phenyl($C_1$-$C_4$)alkyl.

5. A compound of the formula

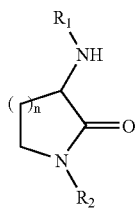

or a pharmaceutically acceptable salt thereof wherein
n is 1 or 2;
$R_1$ is heteroaryl($C_1$-$C_6$)alkyl wherein the cyclic portion is optionally substituted with 1, 2, 3, 4, or 5 groups that are independently halogen, $C_1$-$C_6$ alkyl, $C_1$-$C_6$ alkoxy, $C_1$-$C_4$ haloalkyl, $C_1$-$C_4$ haloalkoxy, aryl, arylalkyl, aryloxy, heteroaryl, —$SO_2$-aryl, —$S(O)_x$—$R_{25}$, —($C_1$-$C_4$ alkyl)-$S(O)_x$—$R_{25}$, CN, $C_1$-$C_6$ thioalkoxy, $C_1$-$C_6$ alkoxycarbonyl, —NR'R", —C(O)—NR'R", or heterocycloalkyl,
wherein the above aryl groups are optionally substituted with 1, 2, 3, or 4 groups that are independently halogen, $C_1$-$C_6$ alkyl, $C_1$-$C_6$ alkoxy, $C_1$-$C_4$ haloalkyl, or $C_1$-$C_4$ haloalkoxy;
wherein the above heteroaryl and heterocycloalkyl groups are optionally substituted with 1, 2, or 3 groups that are independently halogen, $CF_3$, ($C_1$-$C_4$)alkyl, $C_1$-$C_6$ thioalkoxy, OH, $C_1$-$C_4$ hydroxyalkyl, or $C_1$-$C_4$ alkoxy; or $R_1$ is heterocycloalkyl($C_1$-$C_6$ alkyl) wherein the heterocycloalkyl portion contains from 4-7 members and is optionally substituted with 1, 2, 3, 4, or 5 groups that are independently halogen, $C_1$-$C_6$ alkyl, $C_1$-$C_6$ alkoxy, $C_1$-$C_4$ haloalkyl, $C_1$-$C_4$ haloalkoxy, aryl, arylalkyl, aryloxy, heteroaryl, —$SO_2$-aryl, —$S(O)_x$—$R_{25}$, —($C_1$-$C_4$ alkyl)-$S(O)_x$—$R_{25}$, CN, $C_1$-$C_6$ thioalkoxy, $C_1$-$C_6$ alkoxycarbonyl, —NR'R", —C(O)—NR'R", heterocycloalkyl;
each x is independently 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), aryl, or heteroaryl; or
$R_{26}$, $R_{27}$ and the nitrogen to which they are attached form a heterocycloalkyl ring;
wherein R' at each occurrence is independently H, $C_1$-$C_6$ alkyl, aryl, aryl($C_1$-$C_4$)alkyl, $C_1$-$C_6$ alkanoyl, $C_3$-$C_6$ cycloalkyl, aryl($C_1$-$C_6$)alkanoyl, heterocycloalkyl, heteroaryl($C_1$-$C_4$)alkyl, —$SO_2$-alkyl, —$SO_2$-aryl, —$SO_2$-heteroaryl, heterocycloalkyl($C_1$-$C_6$)alkanoyl, or heteroaryl($C_1$-$C_6$)alkanoyl, wherein the alkyl portion of the alkyl and alkanoyl groups are optionally substituted with halogen or $C_1$-$C_6$ alkoxy,
wherein the aryl, and heteroaryl groups are optionally substituted with $C_1$-$C_6$ alkyl, $C_1$-$C_6$ alkoxy, halogen, $C_1$-$C_4$ haloalkyl, $C_1$-$C_4$ haloalkoxy;
wherein R" at each occurrence is independently H, or $C_1$-$C_6$ alkyl, wherein the alkyl group is optionally substituted with halogen; and
$R_2$ is H, $C_1$-$C_6$ alkyl, or phenyl($C_1$-$C_4$)alkyl.

6. A compound of the formula

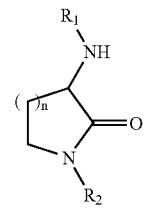

or a pharmaceutically acceptable salt thereof wherein
n is 1 or 3;
$R_1$ is heteroaryl($C_1$-$C_6$)alkyl wherein the cyclic portion is optionally substituted with 1, 2, 3, 4, or 5 groups that are independently halogen, $C_1$-$C_6$ alkyl, $C_1$-$C_6$ alkoxy, $C_1$-$C_4$ haloalkyl, $C_1$-$C_4$ haloalkoxy, aryl, aryloxy, heteroaryl, —$SO_2$-aryl, —$S(O)_x$—$R_{25}$, —($C_1$-$C_4$ alkyl)-$S(O)_x$—$R_{25}$, CN, $C_1$-$C_6$ thioalkoxy, $C_1$-$C_6$ alkoxycarbonyl, —NR'R", —C(O)—NR'R", or heterocycloalkyl,
wherein the above aryl groups are optionally substituted with 1, 2, 3, or 4 groups that are independently halogen, $C_1$-$C_6$ alkyl, $C_1$-$C_6$ alkoxy, $C_1$-$C_4$ haloalkyl, or $C_1$-$C_4$ haloalkoxy, or CN;
wherein the above heteroaryl and heterocycloalkyl groups are optionally substituted with 1, 2, or 3 groups that are independently halogen, $CF_3$, ($C_1$-$C_4$) alkyl, $C_1$-$C_6$ thioalkoxy, OH, $C_1$-$C_4$ hydroxyalkyl, or $C_1$-$C_4$ alkoxy; or
wherein R' is H, $C_1$-$C_6$ alkyl, or $C_1$-$C_6$ alkanoyl, wherein the alkyl portion of the alkyl and alkanoyl groups are optionally substituted with halogen;
wherein R" is H, or $C_1$-$C_6$ alkyl, wherein the alkyl group is optionally substituted with halogen;
each x is independently 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), aryl, or heteroaryl; or
$R_{26}$, $R_{27}$ and the nitrogen to which they are attached form a heterocycloalkyl ring; and
$R_2$ is H, $C_1$-$C_6$ alkyl, or phenyl($C_1$-$C_4$)alkyl.

* * * * *